US005476781A

United States Patent [19]
Moyer et al.

[11] Patent Number: 5,476,781
[45] Date of Patent: Dec. 19, 1995

[54] ENTOMOPOXVIRUS SPHEROIDIN GENE SEQUENCES

[75] Inventors: Richard W. Moyer; Richard L. Hall, both of Gainesville, Fla.

[73] Assignee: University of Florida Research Foundation, Inc., Gainesville, Fla.

[21] Appl. No.: 991,867

[22] Filed: Dec. 7, 1992

Related U.S. Application Data

[63] Continuation-in-part of Ser. No. 827,685, Jan. 30, 1992, abandoned, which is a continuation-in-part of Ser. No. 657,584, Feb. 19, 1991, abandoned.

[51] Int. Cl.$^6$ ............................ C12N 5/10; C12N 15/11; C12N 15/39; C12N 15/62
[52] U.S. Cl. ............................... 435/240.2; 536/23.72; 536/24.1; 435/320.1
[58] Field of Search ............................ 536/23.72, 24.1; 435/320.1, 240.1

[56] References Cited

U.S. PATENT DOCUMENTS 5,174,993  12/1992  Paoletti .............................. 424/199.1
5,338,679  8/1994  Yuen et al. ......................... 435/235.1

OTHER PUBLICATIONS

Yuen, L. et al.; Virology 175:427–433 (1990).
Langridge, W. H. R.; J. Invertebrate Pathol. 43:41–46 (1984).
Vialard, J. E. et al.; J. Virology 64:5804–5811 (1990).
Bilimoria, S. L. et al.; Virology 96:596–603 (1979).
Hull, R. et al.; *Virology Directory & Dictionary of Animal, Bacterial and Plant Viruses,* Stockton Press, New York, 1989, pp 70–71, 274–276.
Pearson, A. et al.; Virology 180:561–566 (1991).
Hunkapiller et al., Science 207:523–525 (1980).
Sambrook et al., *Molecular Cloning: A Laboratory Manual,* 2nd Ed., Cold Spring Harbor Laboratory Press, Cold Spring Harbor, N.Y., 1989, pp. 11.1–11.19.
Sato, Takeru (1989) "Establishment of Eight Cell Lines from Neonate Larvae of Torticids (Lepidoptera), and Their Several Characteristics Including Susceptibility to Insect Viruses" Invertebrate Cell Systems Applications, (J. Mitsuhashi ed.) vol. II, CRC Press, Inc., Boca Raton, Fla., pp. 187–198.
Langridge, W. H. R., R. F. Bozarth, and D. W. Roberts (1977) "The Base Composition of Entomopoxvirus DNA" Virology 76:616–620.
Langridge, W. H. R. (1983) "Detection of *Amsacta moorei* Entomopoxvirus and Vaccinia Virus Proteins in Cell Cultures Restrictive for Poxvirus Multiplication" Journal of Invertebrate Pathology 42:77–82.
Langridge, W. H. R., and D. W. Roberts (1982) "Structural Proteins of *Amsacta moorei, Euxoa auxilliaris,* and *Melanoplus sanguinipes* Entomopoxirus" Journal of Invertebrate Pathology 39:346–353.
Arif, Basil M., and Edouard Kurstak (1991) "The entomopoxviruses" Viruses of Invertebrates (E. Kurstak, ed.) Marcel Dekker, Inc., New York pp. 19–195.
Hall, R. L., and W. F. Hink (1990) "Physical mapping and field inversion gel electrophoresis of *Amsacta moorei* entomopoxvirus DNA" Arch. Virol. 110:77–90.
Hall, Richard L., and Richard W. Moyer "Identification, Cloning, and Sequencing of a Fragment of *Asmacta moorei* Entomopoxvirus DNA Containing the Spheroidin Gene and Three Vaccinia Virus–Related Open Reading Frames" Journal of Virology 65(12):6526≧6527. (1991).

(List continued on next page.)

Primary Examiner—Robert A. Wax
Assistant Examiner—Eric Grimes
Attorney, Agent, or Firm—Saliwanchik & Saliwanchik

[57] ABSTRACT

The subject invention pertains to novel Entomopoxvirus (EPV) spheroidin polynucleotide sequences free from association with other viral sequences with which they are naturally associated, recombinant polynucleotide vectors containing the sequences, recombinant viruses containing the sequences, and host cells infected with the recombinant viruses are provided herein, as well as methods for use thereof in the expression of heterologous proteins in both insect and mammalian host cells.

17 Claims, 28 Drawing Sheets

OTHER PUBLICATIONS

Goodwin, R. H., R. J. Miller, and C. D. Beaton (1991) "Entomopoxvirinae" Atlas of Invertebrate Viruses (J. R. Adams and J. R. Bonami, eds.) CRS Press, Inc., Boca Raton pp. 259–285.

Banville, Myriam, France Dumas, Silvana Trifiro, Basil Arif, and Christopher Richardson (1992) "The predicted amino acid sequence of the spheroidin protein from *amsacta moorei* entomopoxvirus: lack of homology between major occlusion body proteins of different poxviruses" Journal of General Virology 73:559–566.

Piccini, Antonia and Enzo Paoletti (1986) "The Use of Vaccinia Virus for the Construction of Recombinant Vaccines" Bioessays 5:248–252.

Panicali, D., S. W. Davis, R. L. Weinberg, and E. Paoletti (1983) "Construction of live vaccines by using genetically engineered poxviruses: Biological activity of recombinant vaccinia virus expressing influenza virus hemogglutinin" Proc. Natl. Acad. Sci. USA 80:5364–5468.

Mackett, M., G. L. Smith, and B. Moss (1985) "The Construction and Characterisation of Vaccinia Virus Recombinants Expressing Foreign Genes" DNA Cloning, vol. II, (D. M. Glover ed.) Oxford: IRL Press, pp. 191–192.

Paoletti, E., B. R. Lipinskas, C. Samsonoff, S. Mercer, and D. Panicali (1984) "Construction of live vaccines using genetically engineered proxviruses: Biological activity of vaccinia virus recombinants expressing the hepatitis B virus surface antigen and the herpes simplex virus glycoprotein D" Proc. Natl. Acad. Sci. USA 81:193–197.

Hukuhara, Tosihiko, Jinhua Xu, and Kazuhiko Yano (1990) "Replication of an Entomopoxvirus in Two Lepidopteran Cell Lines" Journal of Invertebrate Pathology 56:222–232.

Granados, R. R., and M. Naughton (1976) "Replication of *Amsacta Moorei* Entomopoxvirus and *Autographa californica* Nuclear Polyhedrosis Virus in Hemocyte Cell Lines from *Estigmene acrea*" Invertebrate Tissue Culture Applications in Medicine, Biology, and Agriculture (E. Kurstak and K. Maramorosch eds., ) Academic Press, New York, pp. 379–389.

Roberts and Granados (1968) "Notes: A Poxlike Virus from *Amsacta moorei* (Lepidoptera: Arctiidae)" J. Invertebra. Pathol. 12:141–143.

Fig. 2A

```
AGATCTGATG TTCTATATAT AGTACAAATT TGTATGATTA ATTGATATTT TAAAATTCAA                      60

GATA TTA AAT ATT AGA TTC TAA ACT ATT CTC ATT ATC AAT ATA ACT                          109
     Ile Asn Ser Glu Leu Ser Asn Lys Glu Asn Asp Ile Tyr Ser
      1                         5                        10

ATC ATA ATC ATT TAT TTT ACT ACA TAC ATT CAT AAT TCT ATT ACT ATT                       160
Asp Tyr Asp Asn Lys Ile Lys Ser Cys Val Asn Met Ile Arg Asn Ser Asn
 15                  20                  25                  30

TTT TTT ATA CAT ATC TAT TAA TTC CAT AAA CTT TTT ATT TTT TAT ATT AAA                   211
Lys Lys Tyr Met Asp Ile Leu Glu Met Phe Lys Lys Asn Lys Ile Asn Phe
             35                  40                  45

TAT TTC TAA TGT ATT TTT AAA TTC GTC AAT ACT ATT AAT ATC ATA TCT AGA                   262
Ile Glu Leu Thr Asn Lys Phe Glu Asp Ile Ser Asn Ile Asp Tyr Arg Ser
 50                  55                  60                  65

AAT AAA TGC ACC TCT ATA ACT ACT AGC CAA TAA CTT TAT GTT ATC AAA ACT                   313
Ile Phe Leu Ala Gly Tyr Ser Ser Ala Leu Asp Gly Ile Phe Ser
             70                  75                  80

CAT AGA ATA ATA TAA TTT TTT AAA TTC AAA TTT TAT AGA TTT TAT GTT GAA ATA              364
Met Ser Tyr Tyr Leu Lys Lys Phe Glu Phe Lys Ser Lys Ile Asn Phe Tyr
 85                  90                  95

AAC TAT ATA ATA TAA AAA TAT ATT AAA CAT ACC ACA ATC GGG ACT ATC                      415
Val Ile Tyr Tyr Leu Phe Ile Asn Phe Met Gly Cys Asp Pro Ser Asp
100                 105                 110                 115
```

Fig. 2B

```
ATA TTG TAA TTC AAA AGT ATT AAA ATA ATT TAC ATT TTT AAA TAT                466
Tyr Gln Leu Phe Glu Thr Asn Phe Tyr Tyr Asn Val Asn Lys Phe Ile
            120                 125                 130

ATC ATT TAA TTC TGA TAG TAC ATC AAT GTA TAA ATA ATT AGT                    517
Asp Asn Leu Tyr Glu Ser Leu Val Asp Ile Tyr Leu Tyr Ala Asn Thr
            135                 140                 145         150

ATT AGG AGT ACT ATT GTA GTG TTT ATG GCT TTT TAT AGT CAT ATC AGA TTC        568
Asn Pro Thr Ser Asn Tyr His Lys Ser Met Ala Phe Tyr Ser His Met Asp Ser Glu
                    155                 160                 165

AAT CAT ATA TTT TTT ATT TTG TTT ATT TAT AAG TTC TGG TAT ATA ACC ACT        619
Ile Phe Leu Tyr Lys Lys Asn Gln Lys Ile Leu Glu Pro Ile Tyr Gly Ser
            170                 175                 180

ACT ATT AAA AAA GTA TGC AGC TTT ATC TTT ATC AAA GTG TTT ATC TAT            670
Ser Asn Phe Phe Tyr Ala Ala Lys Lys Asp Phe Ile Lys Val Phe Ile Asp Ile
        185                 190                 195                 200

TAC GCA ACA AGT AAA ATG ATC ATT ATA AAT TAT AGG AAA CAT AAA AAA TCT        721
Val Cys Cys Thr Phe Lys Met Asp His Ile Ile Pro Tyr Asn Phe Met Phe Arg
            205                 210                 215

TTT TTT ATC ATT CAT TAA AAA TTT TAC TCT ATC TTC AAG TTT ATA GCA            772
Lys Lys Asp Asn Met Leu Phe Leu Phe Lys Val Arg Asp Glu Leu Lys Tyr Cys
            220                 225                 230                 235
```

Fig. 2C

```
TCT CAT AGA TGA AGC TAC TGT AGC AAT ATT TTT ATC AGT TTT TTC AAA TAA      823
Arg Met Ser Ser Ala Val Thr Ala Ile Asn Lys Asp Thr Lys Glu Phe Leu
        240                         245                 250

AAT CAA ATG AAA ATA ATC ATA ATC TCC CGA ACT TAA CCA TGT AGA TAA CAT AGT TGG ATA TAT    874
Ile Leu His Phe Tyr Asp Tyr Asp Ser Gly Ser Leu Trp Thr Thr Asn Ile Met Thr Leu Pro Tyr Ile
        255                         260                         265

ACA ATT ATA TAT ATC TCC CGA ACT TAA CCA TGT AGA TAA TTT ATC ATG TTT TCT    925
Cys Asn Tyr Ile Asp Gly Ser Leu Trp Thr Thr Asn Ile Met Thr Leu Pro Tyr Ile
270                         275                         280                         285

TGG GTA AGC TTT AGG ATT AAA TCC CAA AGG CGG TAT TCC TAT TTG    976
Pro Tyr Ala Lys Pro Asn Phe Gly Leu Pro Pro Ile Gly Gln
290                         295                         300

AGC ATC CAA ATC ATA AAT TGT GGC AAA TGT AGA AAA TCT TGT TTT    1027
Ala Asp Leu Asp Tyr Ile Thr Ala Phe Ser Phe Asp Arg Thr Lys
305                         310                         315                         320

GGA TAA TTC TGA TTT TAG AAA AGA CTT TCT CAT ATA TAC TAA TGG AAT GCC    1078
Ser Leu Glu Ser Lys Leu Phe Lys Arg Met Tyr Val Leu Pro Ile Gly
        325                         330                         335

TTT ATA TTT TTT AGA TGT AAT AAA AGT ATT TAT ATT AAT TTT ATC TTG    1129
Lys Tyr Lys Ser Thr Ile Phe Lys Ser Ile Asn Ile Asn Lys Asp Gln
        340                         345                 350
```

Fig. 2D

```
TAA ATA TTT TTT TAT AGT CCA AAA TAG AAA TTT TCT TTT AAT ATT ATT       1180
Leu Tyr Lys Lys Ile Thr Trp Phe Leu Phe Lys Arg Lys Ile Asn Asn
355                 360             365             370

TTC AAA ATT AAT ATT ATT AAT ATG ATT TGG ATC TAA AAC TAA TTC ATT ATA   1231
Glu Phe Asn Ile Asn Ile His Asn Pro Asp Leu Val Leu Glu Asn Tyr
            375             380             385

TAA TAT TTC CAA GTA TTT TAT AGG TAT AAA TGT TAC TTT ACC TCT TGT TTC   1282
Leu Ile Glu Leu Tyr Lys Ile Pro Ile Phe Thr Val Gly Arg Thr Glu
390             395             400             405

ATC ATC ATC ATC TAT TTT TTC TAA TAT AGC TAT ATT TGC ATT AGT ATT ATA   1333
Asp Asp Asp Asp Ile Lys Leu Glu Ile Ala Ile Asn Ala Thr Asn Tyr
410             415             420

TTT AAT AGG ATT TAT AAA ATA TAC TAC CAT ATT ATC TAT ACT AAA AAA TAA   1384
Lys Ile Pro Asn Ile Phe Tyr Val Met Asn Asp Ile Ser Phe Phe Leu
425             430             435

CAT AGA CAT AAA ATT AAT ACC AGA TTC TGG CAT TTT TAA ATT TTT ATT TGG   1435
Met Ser Met Phe Asn Ile Gly Ser Glu Pro Met Lys Leu Asn Lys Asn Pro
440             445             450             455

< G1L       G2R >
AAA TCT TCT AAT TTT ATT CAT TATTTATTTA ATAA ATG TTT CTA GTT TAT       1488
Phe Arg Arg Ile Lys Asn Asn Met                 Met Phe Leu Val Tyr
460                                             465
```

Fig. 2E

```
TTC AAT ACA TTT TTA ATA ATA ATT TTA TTA TTT GGT ATT ATA GGT ATT TAT    1539
Phe Asn Thr Phe Leu Ile Ile Ile Leu Leu Phe Gly Ile Ile Gly Ile Tyr
470                 475                 480                 485

ATA TTA ACA TTT GTG TTT AAT ATA GAT TTT AAT ATA TTA ATA AAA ATA        1590
Ile Leu Thr Phe Val Phe Asn Ile Asp Phe Asn Ile Leu Ile Asn Lys Ile
    490                 495                 500

TAT ATA TCA TAT AAC GCA ACT AAT ATA AAC AAT ATA ATA AAT TTA AAT        1641
Tyr Ile Ser Tyr Asn Ala Thr Asn Ile Asn Asn Ile Ile Asn Leu Asn
505                 510                 515                 520

TTA TAC GAT TAT TCA GAT ATT ATT TTG ACA AAT TTT AAC ATA AAT AAT        1692
Leu Tyr Asp Tyr Ser Asp Ile Ile Leu Thr Asn Phe Asn Ile Asn Asn
    525                 530                 535

AAT CTT TTA GTA ACA CAA GCT AAT TTA CAA GAT ATA CCA ATA TTT AAT        1743
Asn Leu Leu Val Thr Gln Ala Asn Leu Gln Asp Ile Pro Ile Phe Asn
540                 545                 550

GTA AAT ATT ATA TCT AAT CAA TAT AAT TTT TAT TCA GCG TCT AGT AAT        1794
Val Asn Ile Ile Ser Asn Gln Tyr Asn Phe Tyr Ser Ala Ser Ser Asn
555                 560                 565                 570

AAT GTA AAT ATA TTA GGA TTA AGA AAA ACA TTA AAT ATA AAT AGA AAT        1845
Asn Val Asn Ile Leu Gly Leu Arg Lys Thr Leu Asn Ile Asn Arg Asn
    575                 580                 585
```

Fig. 2F

```
CCA TTT TTA TTT AGA AAT ACA TCT CTA GCT ATA GTT TTC AAT AAT AAT  1896
Pro Phe Leu Phe Arg Asn Thr Ser Leu Ala Ile Val Phe Asn Asn Asn
590                 595                 600                 605

GAA ACT TTT CAC TGT TAT ATA AGT TCA AAT CAA AAT AGT GAT GTA TTA GAT  1947
Glu Thr Phe His Cys Tyr Ile Ser Ser Asn Gln Asn Ser Asp Val Leu Asp
          610                 615                 620

ATA GTA TCA CAT ATA GAA TTT ATG AAA TCT AGA TAT AAT TAT GTA ATT  1998
Ile Val Ser His Ile Glu Phe Met Lys Ser Arg Tyr Asn Lys Tyr Val Ile
625                 630                 635

ATA GGA GAA ATA CCC GTA AAT AAT AAT TCT ATT AAT ATA TTA AAT  2049
Ile Gly Glu Ile Pro Val Asn Asn Asn Ser Ile Ser Ile Asn Leu Asn
640                 645                 650                 655

AAT TTT GCT ATT ATA ACT AAT GTG AGA TTA ATA GAT AAA TAT AAC TCT ATA  2100
Asn Phe Ala Ile Ile Thr Asn Val Arg Leu Ile Asp Lys Tyr Asn Ser Ile
          660                 665                 670

ATA TCA TTT TTA AAT ATC AAC GTA GGA ACA CTT TTT GTC ATA AAT CCA TAA  2151
Ile Ser Phe Leu Asn Ile Asn Val Gly Thr Leu Phe Val Ile Asn Pro
675                 680                 685

TATTAGTAA TAATCACTAA CATATTTTTT ATTAAAATGA ATAAAATATA TATTGTTATT  2211

GTCAATATTT TATATCATTT TACAGTC TTA TTT TTT TTT GCT TTT AGG TAT  2265
                              Lys Lys Lys Lys Ser Lys Pro Ile
                              690                 695

AAT TTT ACC TTC TAA ACG TTT ATC TCC CCA AAC ATC TAC AGT AGA TGG TTT  2316
Ile Lys Gly Glu Leu Arg Lys Asp Val Trp Val Asp Val Thr Ser Pro Lys
700                 705                 710

ATT AGA TTC TGT GTT ATA CAC ATC TGC TGG ATT TGC GGC ATT TGT ATC CAA  2367
Asn Ser Glu Thr Asn Tyr Val Asp Ala Pro Asn Ala Ile Cys Ile Asp Leu
715                 720                 725                 730
```

Fig. 2G

```
ACC ATA ATA TCC AGG TCT ATA ATT ATC TTT AAA AAC TTG GGA TTG AGA TAC   2418
Gly Tyr Tyr Gly Pro Arg Ser Ile Ile Phe Lys Asn Val Gly Leu Arg Tyr
            735                 740                 745

TTC TTC AGT TTT TAA ATT ATT AAA ATA TCC AAG ATT ATT TTT TGA TGA       2469
Glu Glu Thr Phe Lys Leu Asn Asn Phe Tyr Gly Leu Asn Asn Lys Lys Ser Ser
        750                 755                 760             765

< G3L                                      G4R >
AGA CAT AATTGATATT ATAATACTTT ATAGAT ATG TCA ATA TTT ATC TAC TAT      2522
Ser Met                                  Met Ser Ile Phe Ile Tyr Tyr
                                                     770

ATT TTC AAC AAT AGA TTT TAT ATA TAT AAA AGA ATG AAT ACT GTA CAA ATT   2573
Ile Phe Asn Asn Arg Phe Tyr Ile Tyr Lys Arg Met Asn Thr Val Gln Ile
        775                 780                 785                 790

TTA GTT GTC ATA TTA ATA ACA GCA TCT TTT CTA GTT TTT CAA TTA           2624
Leu Val Val Ile Leu Thr Thr Ala Leu Ser Phe Leu Val Phe Gln Leu
        795                 800                 805

TGG TAT TAT GCC GAA AAT TAC GAA TAT ATA TTA AGA TAT AAT GAT ACA TAT   2675
Trp Tyr Tyr Ala Glu Asn Tyr Glu Tyr Ile Leu Arg Tyr Asn Asp Thr Tyr
        810                 815                 820                 825

TCA AAT TTA CAA TTT GCG AGA AGC GCA AAT ATA AAT TTT GAT GAT TTA ACT   2726
Ser Asn Leu Gln Phe Ala Arg Ser Ala Asn Ile Asn Phe Asp Asp Leu Thr
        830                 835                 840

GTT TTT GAT CCC AAC GAT AAT GTT TTT AAT GAA GAA AAA TGG CGC TGT       2777
Val Phe Asp Pro Asn Asp Asn Val Phe Asn Val Glu Glu Lys Trp Arg Cys
        845                 850                 855

GCT TCA ACT AAT AAT AAT ATA TTT TAT GCA GTT TCA ACT TTT GGA TTT TTA   2828
Ala Ser Thr Asn Asn Asn Ile Phe Tyr Ala Val Ser Thr Phe Gly Phe Leu
        860                 865                 870                 875
```

Fig. 2H

```
AGT ACA GAA AGT ACT GGT ATT AAT TTA ACA TAT ACA AAT TCT AGA GAT TGT    2879
Ser Thr Glu Ser Thr Gly Ile Asn Leu Thr Tyr Thr Asn Ser Arg Asp Cys
            880                     885                 890

ATT ATA GAT TTA TTT TCT AGA ATT ATA AAA ATA GTA TAT GAT CCT TGT ACT    2930
Ile Ile Asp Leu Phe Ser Arg Ile Ile Lys Ile Val Tyr Asp Pro Cys Thr
        895                     900                 905             910

GTC GAA ACA TCT AAC GAT TGT AGA TTA TTA AGA TTG ATG GCC AAT ACA        2981
Val Glu Thr Ser Asn Asp Cys Arg Leu Leu Arg Leu Met Ala Asn Thr
        915                     920                 925

TCA TAA ATACATTATA ATATTATTAT AATATCAATC ATAATTTTTA TATATATTTT         3037
Ser
                                          G5R >
ATCTAAAAGG ACTTTTTATT TTTTATATAT TAATAATAAT AA ATG AGT AAC GTA CCT     3094
                                               Met Ser Asn Val Pro
                                                930

TTA GCA ACC AAA ACA ATA AGA AAA TTA TCA AAT CGA AAT TAT GAA ATA AAG    3145
Leu Ala Thr Lys Thr Ile Arg Lys Leu Ser Asn Arg Asn Tyr Glu Ile Lys
        935                     940                 945             950

ATT TAT TTA AAA GAT GAA AAT ACT TGT TTC GAA CGT GTA GAT ATG GTA        3196
Ile Tyr Leu Lys Asp Glu Asn Thr Cys Phe Glu Arg Val Asp Met Val
        955                     960                 965

GTT CCA TTA TAT GAT GTG TGT AAT ACT TCT GGT GTT ACT TTA GAA TCA        3247
Val Pro Leu Tyr Asp Val Cys Asn Thr Ser Gly Val Thr Leu Glu Ser
    970                     975                 980

TGT AGT CCA AAT ATA GAA GTA ATT GAA TTA GAC AAT ACT CAT GTT AGA ATC    3298
Cys Ser Pro Asn Ile Glu Val Ile Glu Leu Asp Asn Thr His Val Arg Ile
985                     990                 995                 1000

AAA GTT CAC GGC GAT ACA TTA AAA GAA ATG TGT TTT GAA TTA TTG TTC CCG    3349
Lys Val His Gly Asp Thr Leu Lys Glu Met Cys Phe Glu Leu Leu Phe Pro
        1005                    1010                1015
```

Fig. 21

```
TGT AAT GTA AAC GAA GCC CAA GTA TGG AAA TAT GTA AGT CGA TTA TTG CTA   3400
Cys Asn Val Asn Glu Ala Gln Val Trp Lys Tyr Val Ser Arg Leu Leu Leu
        1020            1025            1030            1035

GAT AAT GTA TCA CAT AAT GAC GTA AAA TAT AAA TTA GCT AAT TTT AGA CTG   3451
Asp Asn Val Ser His Asn Asp Val Lys Tyr Lys Leu Ala Asn Phe Arg Leu
        1040            1045            1050

ACT CTT AAT GGA AAA CAT TTA AAA TTA AAA GAA ATC GAT CAA CCG CTA TTT   3502
Thr Leu Asn Gly Lys His Leu Lys Leu Lys Glu Ile Asp Gln Pro Leu Phe
        1055            1060            1065

ATT TAT TTT GTC GAT GAT TTG GGA AAT TAT GGA TTA GGT ATT ACT AAG GAA AAT   3553
Ile Tyr Phe Val Asp Asp Leu Gly Asn Tyr Gly Leu Ile Thr Lys Glu Asn
1070            1075            1080            1085

ATT CAA AAT AAT TTA CAA GTT AAC AAA TTA GAT GCA TCA TTT ATT ACT ATA   3604
Ile Gln Asn Asn Leu Gln Val Asn Lys Leu Asp Ala Ser Phe Ile Thr Ile
        1090            1095            1100

TTT CCA CAA TAT GCG TAT ATT TGT ATT TTA GGT AGA AAA GTA AAA ATT ACT TTA AAT GAA   3655
Phe Pro Gln Tyr Ala Tyr Ile Cys Leu Gly Arg Lys Val Tyr Leu Asn Glu
1105            1110            1115            1120

AAA GTA ACT TTT GAT GTA ACT ACA GAT GCA ACT AAT ATT ACT TTA GAT TTT   3706
Lys Val Thr Phe Asp Val Thr Thr Asp Ala Thr Asn Ile Thr Leu Asp Phe
        1125            1130            1135

AAT AAA TCT GTT AAT ATC GCA GTA TCA TTC CTT GAT ATA TAT TAC GAA GTT   3757
Asn Lys Ser Val Asn Ile Ala Val Ser Phe Leu Asp Ile Tyr Tyr Glu Val
        1140            1145            1150

AAT AAT GAA CAA AAA GAT TTA TTA AAA GAT TTA CTT AAG AGA TAC GGT   3808
Asn Asn Glu Gln Lys Asp Leu Leu Lys Asp Leu Leu Lys Arg Tyr Gly
1155            1160            1165            1170
```

Fig. 2J

```
GAA TTT GAA GTC TAT AAC GCA GAT ACT GGA TTA ATT TAT GCT AAA AAT CTA   3859
Glu Phe Glu Val Tyr Asn Ala Asp Thr Gly Leu Ile Tyr Ala Lys Asn Leu
        1175                        1180                1185

AGT ATT AAA AAT TAT GAT ACT GTG ATT CAA GTA GAA AGG TTG CCA GTT AAT   3910
Ser Ile Lys Asn Tyr Asp Thr Val Ile Gln Val Glu Arg Leu Pro Val Asn
        1190                        1195                1200      1205

TTG AAA GTT AGA GCA TAT ACT AAG GAT GAA AAT GGT CGC AAT CTA TGT TTG   3961
Leu Lys Val Arg Ala Tyr Thr Lys Asp Glu Asn Gly Arg Asn Leu Cys Leu
        1210                        1215                1220
                                                RM58
ATG AAA ATA ACA TCT AGT ACA GAA GTA GAC CCC GAG TAT GTA ACT AGT AAT   4012
Met Lys Ile Thr Ser Ser Thr Glu Val Asp Pro Glu Tyr Val Thr Ser Asn
        1225                        1230                1235

AAT GCT TTA TTG GGT ACG CTC AGA GTA TAT AAA AAG TTT GAT AAA TCT CAT   4063
Asn Ala Leu Leu Gly Thr Leu Arg Val Tyr Lys Lys Phe Asp Lys Ser His
1240                        1245                1250               1255

TTA AAA ATT GTA ATG CAT AAC AGA GGA AGT GGT AAT GTA TTT CCA TTA AGA   4114
Leu Lys Ile Val Met His Asn Arg Gly Ser Gly Asn Val Phe Pro Leu Arg
        1260                        1265                1270

TCA TTA TAT CTG GAA TTG TCT AAT GTA AAA GGA TAT CCA GTT AAA GCA TCT   4165
Ser Leu Tyr Leu Glu Leu Ser Asn Val Lys Gly Tyr Pro Val Lys Ala Ser
        1275                        1280                1285      1290

GAT ACT TCG AGA TTA GAT GTT GGT ATT TAC AAA TTA TTA AAT AAA ATT TAT GTA   4216
Asp Thr Ser Arg Leu Asp Val Gly Ile Tyr Lys Leu Leu Asn Lys Ile Tyr Val
        1295                        1300                1305

GAT AAC GAC GAA AAT ATT ATA TTG GAA GAA ATT GAA GCA GAA TAT AGA   4267
Asp Asn Asp Glu Asn Ile Ile Leu Glu Glu Ile Glu Ala Glu Tyr Arg
        1310                        1315                1320
```

Fig. 2K

```
TGC GGA AGA CAA GTA TTC CAC GAA GTA AAA CTT AAT AAA CAC CAA TGT    4318
Cys Gly Arg Gln Val Phe His Glu Val Lys Leu Asn Lys His Gln Cys
1325                    1330                1335                1340

AAA TAT ACT CCC AAA TGT CCA TTC CAA TTT GTT GTA AAC AGC CCA GAT ACT    4369
Lys Tyr Thr Pro Lys Cys Pro Phe Gln Phe Val Val Asn Ser Pro Asp Thr
        1345                1350                1355

ACG ATT CAC TTA TAT GGT ATT TCT AAT GTT TGT TTA AAA CCT AAA GTA CCC    4420
Thr Ile His Leu Tyr Gly Ile Ser Asn Val Cys Leu Lys Pro Lys Val Pro
    1360                1365                1370                1375

AAA AAT TTA AGA CTT TGG GGA TGG ATT TTA GAT ACT TGC GAT ACT TCT AGA TTT    4471
Lys Asn Leu Arg Leu Trp Gly Trp Ile Leu Asp Thr Cys Asp Thr Ser Arg Phe
        1380                1385                1390

ATT AAA CAT ATG GCT GAT GGA TCT GAT GGA TTA GAT CTT GAC GTT AGG CTT    4522
Ile Lys His Met Ala Asp Gly Ser Asp Gly Leu Asp Leu Asp Val Arg Leu
    1395                1400                1405

AAT GAT AAT GAT ATA TGT TTA AAA CAA GCC ATA AAA CAT TAT ACT AAT    4573
Asn Asp Asn Asp Ile Cys Leu Lys Gln Ala Ile Lys His Tyr Thr Asn
1410                1415                1420                1425

GTA ATT ATA TTA GAG TAC GCA AAT ACA TAT TYR CCA AAT TGC ACA TTA TTG    4624
Val Ile Ile Leu Glu Tyr Ala Asn Thr Tyr Pro Asn Cys Thr Leu Leu
        1430                1435                1440

GGT AAT AAT AGA TTT AAT AAT GTA TTT GAT ATG AAT GAT AAC AAA ACT ATA    4675
Gly Asn Asn Arg Phe Asn Asn Val Phe Asp Met Asn Asp Asn Lys Thr Ile
    1445                1450                1455                1460

TCT GAG TAT ACT AAC TTT ACA AAA AGT AGA CAA GAC CTT AAT AAC ATG TCA    4726
Ser Glu Tyr Thr Asn Phe Thr Lys Ser Arg Gln Asp Leu Asn Asn Met Ser
        1465                1470                1475
```

Fig. 2L

```
TGT ATA TTA GGA ATA AAC ATA TCC GTA AAT ATT AGT AGT TTG CCT  4777
Cys Ile Leu Gly Ile Asn Ile Ser Val Asn Ile Ser Ser Leu Pro
              1480                  1485                1490

GGT TGG GTA ACA CCT CAC GAA GCT AAA ATT CTA AGA TCT GGT AGA  4828
Gly Trp Val Thr Pro His Glu Ala Lys Ile Leu Arg Ser Gly Arg
1495                1500                1505                1510

GTT AGA GAA TTT TGT AAA TCA TTC TGT GAT CTT TCT AAT AAG AGA  4879
Val Arg Glu Phe Cys Lys Ser Phe Cys Asp Leu Ser Asn Lys Arg
              1515                1520                1525

GCT ATG GCT AGA GAT CTC GTA AGT TTA CTA TTT ATG TGT AAC TAT  4930
Ala Met Ala Arg Asp Leu Val Ser Leu Leu Phe Met Cys Asn Tyr
1530                1535                1540                1545

ATT GAA ATT AAC GAA GCA GTA ATT AAA GTA TGC GAA TAT CCT GGA  4981
Ile Glu Ile Asn Glu Ala Val Ile Lys Val Cys Glu Tyr Pro Gly
              1550                1555                1560

GCA AGA GCT ATT AAA GCT ATT AAT GAT TTA TTA ATT AAC GGA GTA  5032
Ala Arg Ala Ile Lys Val Ile Asn Asp Leu Leu Ile Asn Gly Val
1565                1570                1575

AAT CTA GCA GGA TAT TCA ATT TCC TTA CCT ATA CAT TAT GGA TCT  5083
Asn Leu Ala Gly Tyr Ser Ile Ser Leu Pro Ile His Tyr Gly Ser
1580                1585                1590                1595

AAG ACT CTA CCA AAT GAA AAG TAT GGT GGT GTT GAT AAG AAA TTT  5134
Lys Thr Leu Pro Asn Glu Lys Tyr Gly Gly Val Asp Lys Lys Phe
1600                1605                1610

CTA TTC TTA AAG AAT AAA CTA AAA GAT TTA ATG CGT GAT GCT GAT  5185
Leu Phe Leu Lys Asn Lys Leu Lys Asp Leu Met Arg Asp Ala Asp
1615                1620                1625                1630
```

Fig. 2M

```
CAA CCT CCA TTA TAT ATT TCT ACT TAC TTT AGA ACT TTA TTG GAT GCT CCA    5236
Gln Pro Pro Leu Tyr Ile Ser Thr Tyr Phe Arg Thr Leu Leu Asp Ala Pro
                1635                1640                1645

CCA ACT GAT AAT TAT GAA AAA TAT GAA AAA TAT TTG GTT GAT TCG CAA CAA    5287
Pro Thr Asp Asn Tyr Glu Lys Tyr Leu Val Asp Ser Val Gln Ser Gln
                1650                1655                1660

GAT GTT CTA CAG GGT CTG TTG AAT ACA TGT AAT ACT ATT GAT ACT AAT GCT    5338
Asp Val Leu Gln Gly Leu Leu Asn Thr Cys Asn Thr Ile Asp Thr Asn Ala
        1665                1670                1675                1680

AGA GTT GCA TCA AGT ATT GGA GTT ATT GGA TAT GTT TAT GAA CCA TGC GGA ACA TCA    5389
Arg Val Ala Ser Ser Val Ile Gly Val Tyr Glu Pro Cys Gly Thr Ser
        1685                1690                1695

GAA CAT AAA ATT GGT TCA GAA GCA TTG TGT AAA ATG GCT AAA GAA GCA TCT    5440
Glu His Lys Ile Gly Ser Glu Ala Leu Cys Lys Met Ala Lys Glu Ala Ser
        1700                1705                1710                1715

AGA TTA GGA AAT CTA GGT TTA GTA AAT CGT ATT AAT GAA AGT AAT TAC AAC    5491
Arg Leu Gly Asn Leu Gly Leu Val Asn Arg Ile Asn Glu Ser Asn Tyr Asn
        1720                1725                1730

AAA TGT AAT AAA TAT GGT TAT GGA TAC GTA GAA TAC GAA AAT AAC AAA CTA AAA    5542
Lys Cys Asn Lys Tyr Gly Tyr Arg Gly Val Tyr Glu Asn Asn Lys Leu Lys
                1735                1740                1745

ACA AAA TAT TAT AGA GAA ATA TTT GAT TGT AAT CCT GAT TGT AAT AAT AAT GAA    5593
Thr Lys Tyr Tyr Arg Glu Ile Phe Asp Cys Asn Pro Asn Asn Asn Glu
        1750                1755                1760                1765

TTA ATA TCC AGA TAT GGA TAT GGA TAT AGA ATA ATG GAT TTA CAT AAA ATT GGA GAA    5644
Leu Ile Ser Arg Tyr Gly Tyr Arg Ile Met Asp Leu His Lys Ile Gly Glu
        1770                1775                1780
```

Fig. 2N

```
ATT TTT GCA AAT TAC GAT GAA AGT GAA TCT CCT TGC GAA CGA AGA TGT CAT   5695
Ile Phe Ala Asn Tyr Asp Glu Ser Glu Ser Pro Cys Glu Arg Arg Cys His
1785                    1790                1795                1800

TAC TTG GAA GAT AGA GGT AGA GGT CTT TAT GGT CCT GAA TAT CAC CAC AGA   5746
Tyr Leu Glu Asp Arg Gly Arg Gly Leu Tyr Gly Pro Glu Tyr His His Arg
        1805                1810                1815

TAT CAA GAA TCA TGT ACG CCT AAT ACG TTT GGA AAT AAC ACA AAT TGT GTA   5797
Tyr Gln Glu Ser Cys Thr Pro Asn Thr Phe Gly Asn Asn Thr Asn Cys Val
1820                1825                1830

ACA AGA AAT GGT GAA CAA CAC GTA TAC GAA AAT AGT TGT GGA GAT AAT GCA   5848
Thr Arg Asn Gly Glu Gln His Val Tyr Glu Asn Ser Cys Gly Asp Asn Ala
1835                1840                1845                1850

ACA TGT GGA AGA ACA GGA TAT GGA AGA AGT AGG AGT GAT GAA TGG AAT       5899
Thr Cys Gly Arg Thr Gly Tyr Gly Arg Arg Ser Arg Asp Glu Trp Asn
        1855                1860                1865

GAC TAT AGA AAA CCC CAC GTT TAT GAC AAT TGT GCC GAT GCA AAT AGT TCA   5950
Asp Tyr Arg Lys Pro His Val Tyr Asp Asn Cys Ala Asp Ala Asn Ser Ser
        1870                1875                1880                1885

TCT TCA GAT AGC TGT TCA GAC AGT AGT AGT AGT GAA TCT GAA TCT GAT       6001
Ser Ser Asp Ser Cys Ser Asp Ser Ser Ser Ser Glu Ser Glu Ser Asp
            1890                1895                1900

TCA GAT GGA TGT GAC ACA GAT GCT AGT TTA GAT TCT GAT ATT GAA AAT       6052
Ser Asp Gly Cys Asp Thr Asp Ala Ser Leu Asp Ser Asp Ile Glu Asn
        1905                1910                1915

TGT TAT CAA AAT CCA TCA AAA TGT GAT GCA GGA TGC TAA ATGAAATTTA        6101
Cys Tyr Gln Asn Pro Ser Lys Cys Asp Ala Gly Cys
1920                1925                1930
```

Fig. 20

```
ATATTATATA ATATTAACTT ACAAGTTATA AAAATCATTA AAATGATTTT TTAAAATGAT    6161

ATTATCGATA GTTGTGATAA TGTGCTCTTT TATTTATTA ATTGCGATGA TTATAATATT    6221

ATCTTTTAGA TATATTTAAT ATTAATTAAT AATCGACTGA CAATAATATT TATTC CTA    6279

TTC ATA ATA ATC ATC ATC TGC TAT ATA TAT TAA TGT ATC ATT CTC TAT TAT AAA    6330
Glu Tyr Tyr Asp Asp Ala Ile Tyr Ile Leu Thr Asp Asn Glu Ile Ile Phe
            1935                   1940                   1945

TAT AGG TAT ATT GTC TTT ATC AAT CAT TAA TTT TGC TAC AGC TGT ATT ATC    6381
Ile Pro Ile Asn Asp Lys Asp Ile Met Leu Lys Ala Val Ala Thr Asn Asp
            1950                   1955                   1960      1965

TTT ATA TAC TAT ATT TGT GTC TTT GTT TAA TAA ACC TTT TAA TAT AGT GGC    6432
Lys Tyr Val Ile Asn Thr Asp Lys Asn Leu Leu Gly Lys Leu Thr Ala
            1970                   1975                   1980

TCT ATC ATA ATC TTT ACA ATA TGA TAT GGG ATA TAA TTT TAT ATT AAT AAT    6483
Arg Asp Tyr Asp Lys Cys Tyr Ser Ile Pro Tyr Leu Lys Ile Asn Ile Ile
            1985                   1990                   1995

AAC ATT AGA TAC GTT CAT TTC TTT CAT TCT AGT TTT ACG TAT TGT GTC AAA    6534
Val Asn Ser Val Asn Met Glu Lys Met Arg Thr Lys Arg Ile Thr Asp Phe
            2000                   2005                   2010      2015

AAT TAT TTC ATT TTC TGC TGG TTC TAT ATA TTT ATA TGT GTT ATG AAT AGA    6585
Ile Ile Glu Asn Glu Ala Pro Glu Ile Tyr Lys Tyr Thr Asn His Ile Ser
            2020                   2025                   2030

TTC GAT AGA TGA TTT TAA TAA ATC AAA TAT AAC ATT TAT TTT ACC TTG    6636
Glu Ile Ser Ser Lys Leu Leu Asp Phe Ile Val Asn Ile Lys Gly Gln
            2035                   2040                   2045   2050
```

Fig. 2P

```
TTT ATC TTT TAT AAT ATC TAA TAT TTC TTT ATC TAC AGA TTT TCT GTT GTT              6687
Lys Asp Lys Ile Ile Asp Leu Ile Glu Lys Asp Val Ser Lys Arg Asn Asn
                         2055              2060              2065

GGT ATA TGA TAT TAA AAA ATG AAC GTT AAC ATA TCT ATA TTC TTG TGG TAA              6738
Thr Tyr Ser Ile Leu Phe His Val Asn Val Tyr Arg Tyr Glu Gln Pro Leu
         2070              2075              2080

< G6L
ATC TTT ATG AGA ATT TAA TCT TAT AGA TCT                                          6768
Asp Lys His Ser Asn Leu Arg Ile Ser Arg
2085              2090         2094
```

Fig. 3A

```
GAATTCAAGT TAAATAT TTA TAA ACA ACA ATC ATA TTT TTT TAA AGA ATC TAA                    53
                    Leu Cys Asp Tyr Lys Leu Ser Asp Leu
                     1                       5                      10

TAA ATT TTT TAA CAT TTT ATT ATT TGA TAA TTG TTT ATT TAA TTC GTT                       104
Leu Asn Lys Leu Met Lys Asn Asn Ser Leu Gln Lys Asn Leu Glu Asn
                 15                      20                      25

ATT GAT ATT AAC AAT ATT TAT CAT TTT ACC TAT TTT TTT TCT ATC                           155
Asn Ile Asn Val Ile Asn Asn Ile Met Lys Gly Ile Lys Lys Arg Asp
         30                      35                      40                      45
                                            RM129
TAC TAA CGA AAT ATC AGA TTT TGC ACC TTC AAT ATC AGA ATA ATA ATT ATC                   206
Val Leu Ser Ile Asp Ser Lys Ala Gly Glu Ile Asp Ser Tyr Tyr Asn Asp
                 50                      55                      60

< ORF Q1
ATT ATT TTG CAT TTATGAATAA AAATA TTA ATA TGA ATT ATT ATA ACA TAA                      257
Asn Asn Gln Met                                    Tyr Ser Asn Asn Tyr Cys Leu
             65                                                           70

TCT ACA CAC AGG AAC ATA TAA ATC TTG TCC ACC TAT TTC AAT TAT TTG ATT                   308
Arg Cys Val Pro Val Tyr Leu Asp Gln Gly Gly Ile Glu Ile Ile Gln Asn
             75                      80                      85                      90

TTT ATT ATG TTT TTT AAT TGT AAA AGA AGC ATC TTT ATA ACA AAA TTG ACA                   359
Lys Asn His Lys Lys Ile Thr Phe Ser Ala Asp Lys Tyr Cys Phe Gln Cys
                 95                     100                     105

TAT AGC TTG TAA TTT TAT TTT TAC TTT AGG AAT TAA TTT TGA TAT                           410
Ile Ala Gln Leu Lys Lys Ile Lys Glu Val Lys Pro Ile Leu Lys Ser Ile
             110                     115                     120
```

Fig. 3B

```
                                            RM03
AGA ATT AAA TAT ATT TCT GTT AAA TTT ATT ACA ATT TAA TCC AGC AAC AAT AAC       461
Ser Asn Phe Ile Asn Arg Phe Asn Asp Cys Asn Leu Gly Ala Val Ile Val
125                 130                 135                 140

TTT TTT ATT ATT AGC CAT TTT ATC ACA AAA TTG TTC TAA ATC ATT TTC               512
Lys Lys Asn Asn Ala Met Lys Asp Cys Phe Gln Glu Leu Asp Asn Glu
        145                 150                 155

TTC AAA TTG ACA CTC ATC TAT GCC AAT ATC ATA ATT ATC TAC GAT                   563
Glu Phe Gln Cys Glu Gly Ile Gly Ile Ile Asp Tyr Asn Asp Val Ile
160                 165                 170                 175

ATT GAT TTC ATT AAT TAA ATT ATT TGT TTT AAT GTA TAA ATA TTC TTT ATT           614
Asn Ile Glu Asn Ile Leu Asn Asn Thr Lys Ile Tyr Leu Tyr Glu Lys Asn
        180                 185                 190

TAA TAT ATT TCC GTC ATG ATT TAT ATT TTT ATT TAT AAA TCT ATT ATC               665
Leu Ile Asn Gly Asp His Asn Ile Ile Asn Lys Ile Phe Arg Asn Asp
195                 200                 205

TAT ATT ATG AGT TAT AAT TAC ACA TTT TTG ATT AGA TAA ATA TCT ATT               716
Ile Asn His Thr Ile Ile Val Cys Lys Gln Asn Ser Leu Ile Tyr Arg Asn
210                 215                 220                 225
                                             RM04
AAT TTT TCG CAT CAA TTC TGT TGT TTT GCC AGA AAA CAT AGG ACC AAT TAT           767
Ile Lys Arg Met Leu Glu Thr Thr Lys Lys Gly Ser Phe Met Pro Gly Ile Ile
        230                 235                 240

< ORF Q2
TAA TTC TAT CGA CAT TTTTTTTTAT TATTGATAT ATTTTTTCAA AAAAAAATTA                822
Leu Glu Ile Ser Met
245

ORF Q3 >
ATCAATGAAA AAAAAATAAA ATTATCAAA ATG GAT TTA CTA AAT TCT GAT ATA ATT           878
                              Met Asp Leu Leu Asn Ser Asp Ile Ile
                                           250                 255
```

Fig. 3C

```
TTA ATA AAT ATT TTA AAA TAT TAT AAT TTA AAA ATA ATA AAC AGA          929
Leu Ile Asn Ile Leu Lys Tyr Tyr Asn Leu Lys Ile Ile Asn Arg
260             265             270

GAT AAT GTT ATT AAT ATT TTA AAA ATA TTA AAA GTT AAT TTA GAA GAA      980
Asp Asn Val Ile Asn Ile Leu Lys Ile Leu Lys Val Asn Leu Glu Glu
275             280             285             290

TTG CAT ATA TAT GAT AAT AAT ATT TTA AAT AAT ATT CCA GAA AAT         1031
Leu His Ile Tyr Asp Asn Asn Ile Leu Asn Asn Ile Pro Glu Asn
295             300             305

ATT AAA AGT TTA TAT ATT TCA AAT ATT ATT ATA TTA AAT TTT ATA         1082
Ile Lys Ser Leu Tyr Ile Ser Asn Ile Ile Ile Leu Asn Phe Ile
310             315             320             325

ACA AAA TTA AAA AAT ATA ACA TAT TTA GAT ATA TCT TAT AAC AAT AGC     1133
Thr Lys Leu Lys Asn Ile Thr Tyr Leu Asp Ile Ser Tyr Asn Asn Ser
330             335             340

AAT ATA AGT AAT ATT ATT ATA CTA CCA CAT TCT ATA GAA TTT TTA AAT     1184
Asn Ile Ser Asn Ile Ile Ile Leu Pro His Ser Ile Glu Phe Leu Asn
345             350             355

TCA TGT AAT ATA AAT GAC TAT TAT AAT TTT ATT AAT TTA GTA AAT TGT GAA 1235
Ser Cys Asn Ile Asn Asp Tyr Tyr Asn Phe Ile Asn Leu Val Asn Cys Glu
360             365             370             375

AAA TTA ATA TCT AAA AAT AAA TTT GGT AAC TTT AAT AAT GTT TTT CCT     1286
Lys Leu Ile Ser Lys Asn Lys Phe Gly Asn Phe Asn Asn Val Phe Pro
380             385             390

ATT AGT ATA GTT GAG TTA AAT ATG GAA TCA GAA ATA CAA ATA GAT TAT AAA 1337
Ile Ser Ile Val Glu Leu Asn Met Glu Ser Glu Ile Gln Ile Asp Tyr Lys
395             400             405             410
```

Fig. 3D

```
TTT ATA GAA AAA TTA ATT AAT TTA AAA AAA TTA GAT ATA TCT TTC AAT GTT    1388
Phe Ile Glu Lys Leu Ile Asn Leu Lys Lys Leu Asp Ile Ser Phe Asn Val
        415                 420                 425

AAA AAT AAT CAA CAT TTG ATA AAA TTT CCA AAA AGT ATA ACT CAT TTA        1439
Lys Asn Asn Gln His Leu Ile Lys Phe Pro Lys Ser Ile Thr His Leu
    430                 435                 440

TGT GAT TAT CAA TCA TAT AAA GAA AAT TAT TTA AAA AAT TTA TCA            1490
Cys Asp Tyr Gln Ser Tyr Lys Glu Asn Tyr Leu Lys Asn Leu Ser
445                 450                 455                 460

AAT ATA ATT GAA TAT GAA TTC                                            1511
Asn Ile Ile Glu Tyr Glu Phe
            465
```

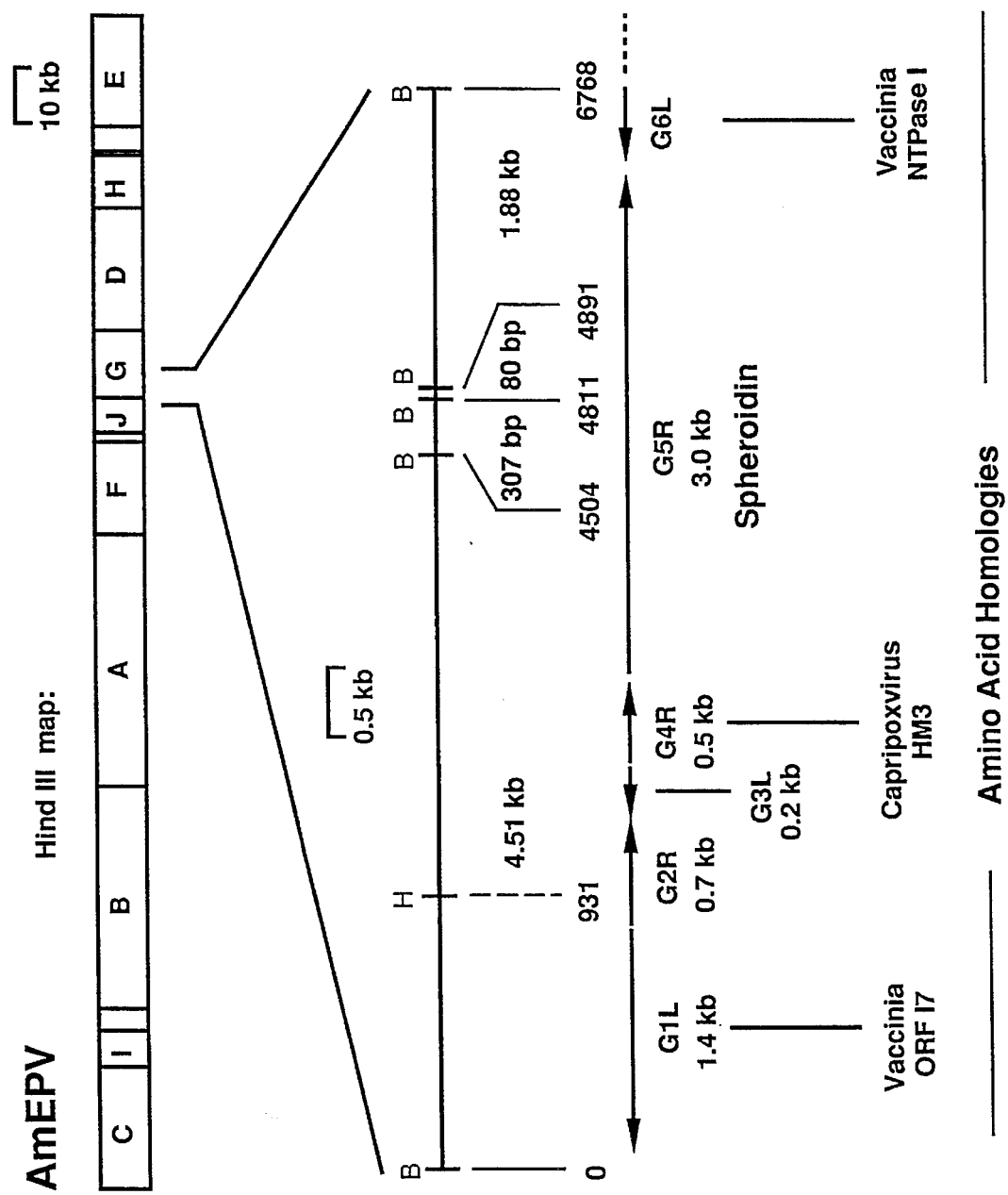

Fig. 5

AmEPV Spheroidin, 3009 bp 250 bp

Fig. 6A

```
        4044          .           .           .           .           .
AmEPV   AAAAGTTTGATAAATCTCATTTAAAAATTGTAATGCATAACAGAGGAAGT
        ||||||||||||||| ||||||||||||| |||||||| |||||||||
CbEPV  1 AAAAGTTTGATAAATCACATTTAAAAATTGTTATGCATAATAGAGGAAGT
        ||||||||||||||||||||||||||||| |||||||| |||||||||||
CfEPV  1 AAAAGTTTGATAAATCACATTTAAAAATCGTTATGCACAATAGAGGAAGC

4094          .           .           .           .           .
AmEPV   GGTAATGTATTTCCATTAAGATCATTATATCTGGAATTGTCTAATGTAAA
        |||||||||| ||  | |||||| ||||| |||||| |  || || ||
CbEPV 51 GGTAATGTATTCCCTATTAGATCACTATATTTGGAATTATTGAACGTCAA
        ||||||||||||||||||||||||||||||||||||||||||||||||||
CfEPV 51 GGTAATGTATTCCCTATTAGATCACTATATTTGGAATTATTGAACGTCAA

4144          .           .           .           .           .
AmEPV   AGGATATCCAGTTAAAGCATCTGATACTTCGAGATTAGATGTTGGTATTT
        ||| ||||| || ||||||||  |||| ||||| |||||||||||| |||
CbEPV 101 AGGTTATCCTGTAAAAGCATCCGATACGTCTAGGTTAGATGTTGGTGTTT
        |||||||||||| ||||||||||||||||||||||||||||| |||||||
CfEPV 101 AGGTTATCCTGTTAAAGCATCCGATACGTCTAGGTTAGACGTTGGTGT

4194          .           .           .           .           .
AmEPV   ACAAATTAAATAAAATTTATGTAGATAACGACGAAAATAAAATTATATTG
        | ||| ||||||||| ||| | ||||| || |||||||||| || || ||
CbEPV 151 ATAAACTAAATAAAATATATATTGATAATGATGAAAATAAAATAATTTTA
        ||||||||||||||||||||||||||||||||||||||||||||||||||
CfEPV 151 ATAAACTAAATAAAATATATATTGATAATGATGAAAATAAAATAATTTTA

4244          .           .     . 4278
AmEPV   GAAGAAATTGAAGCAGAATATAGATGCGGAAGACA
        |||||||||||| | || ||||||||| |||||| |
CbEPV 201 GAAGAAATTGAAACCGATTATAGATGTGGAAGAGA 235
        ||||||||| ||||||||||||||||||||||||||
CfEPV 201 GAAGAAATCGAAACCGATTATAGATGTGGAAGAGA 235
```

Fig. 6B

```
         323        .         .         .         .         .
AmEPV    KFDKSHLKIVMHNRGSGNVFPLRSLYLELSNVKGYPVKASDTSRLDVGIY
         ||||||||||||||||||||||:||||||| |||||||||||||||||||:|
CbEPV  1 KFDKSHLKIVMHNRGSGNVFPIRSLYLELLNVKGYPVKASDTSRLDVGVY
         ||||||||||||||||||||||||||||||||||||||||||||||||||
CfEPV  1 KFDKSHLKIVMHNRGSGNVFPIRSLYLELLNVKGYPVKASDTSRLDVGVY

373        .         399
AmEPV    KLNKIYVDNDENKIILEEIEAEYRCGR
         ||||||:|||||||||||.:|||||
CbEPV    KLNKIYIDNDENKIILEEIETDYRCGR  77
         |||||||||||||||||||||||||||
CfEPV    KLNKIYIDNDENKIILEEIETDYRCGR  77
```

Fig. 6C

```
              211       221
AmEPV         KFKYLFLKNK
              ||||||||||
CbEPV       1 KFKYLFLKNK 10

682       691
AmEPV         KSVNIAVSFLD
              |||||||||||
CbEPV       1 KSVNIAVSFLD 11

726       736
AmEPV         KYLVDSSVQSQ
              |||||||||||
CbEPV       1 KYLVDSSVQSQ 11
```

Fig. 7A

```
          G  I  I  Q  K  L  E  S  E  N  W  P  M  D  L  I
6769  TCCTATTATTTGTTTTAATTCTGATTCATTCCACGGCATATCTAATATAA

I  I  D  N  I  C  K  F  S  I  G  E  S  G  A  Y  S
6819  TTATATCATTAATACATTTGAATGATATGCCTTCAGATCCAGCGTAAGAA

F  I  C  V  K  V  K  K  G  N  N  N  E  Y  N  N  Y
6869  AATATGCAAACTTTTACTTTTTTACCATTATTATTTTCATAATTATTATA

E  N  L  E  N  D  R  T  K  L  T  K  S  S  Y  E
6919  TTCGTTTAATTCATTATCTCTAGTTTTTAAAGTTTTGCTAGAATATTCAA

I  Y  S  I  N  F  C  N  F  Y  C  K  L  S  S  I  G
6969  TATAAGAAATATTAAAACAATTAAAATAACATTTTAAACTTGATATTCCT

E  F  N  V  L  P  E  F  I  L  V  K  G  R  S  N  L
7019  TCAAAATTAACTAAAGGTTCAAATATTAATACTTTTCCTCTCGAATTTAA

I  I  K  C  T  E  I  Y  K  C  S  Y  Q  Y  L  I
7069  AATTATTTTACAAGTTTCTATATATTTACACGAATATTGATATAATATAT

N  Y  N  N  I  D  T  I  P  L  N  T  K  I  K  I  N
7119  TATAATTATTTATATCAGTGATTGGTAAATTAGTTTTTATTTTTATATTA

D  N  K  F  S  E  I  F  S  E  S  F  N  I  N  K  T
7169  TCATTTTTAAAACTTTCAATAAAAGATTCAGAGAAATTAATATTTTTTGT

F  E  S  F  E  A  L  K  R  K  I  M  D  N  Y  E
7219  AAACTCGGAAAATTCAGCAAGTTTTCTTTTAATCATATCATTATATTCTA

I  N  D  L  D  G  K  I  K  L  D  Y  A  F  S  S
7269  TATTATCTAAATCTCCTTTTATTTTAAGATCATAAAAAGCAAATGAAGAT

I  L  R  R  M  T  K  L  G  G  L  E  T  K  Y  D  Y
7319  ATTAATCTTCTCATAGTTTTTAAACCACCTAATTCAGTTTTATAATCATA

K  E  A  M  N  Y  L  K  S  Q  E  D  S  M  I  I
7369  TTTTTCTGCCATATTATATAATTTAGATTGCTCATCTGACATAATTATAT

N  H  Y  F  I  N  K  K  A  Y  G  D  I  Y  N  T  E
7419  TATGATAAAATATATTTTTTTTGCATATCCATCTATATAATTTGTTTCT

T  L  S  D  A  E  I  L  R  K  Y  S  C  I  A  L  L
7469  GTTAAACTATCTGCTTCTATTAATCTTTTATAAGAACATATAGCTAATAA

T  E  R  L  E  K  F  N  I  L  K  G  N  N  I  Y
7519  TGTTTCTCTTAATTCCTTAAAATTAATTAACTTTCCATTATTTATATATT

E  E  K  I  N  M  V  N  P  R  L  L  G  I  L  N  N
7569  CTTCTTTTATATTCATAACATTTGGTCTAAGTAAACCTATTAAATTATTA
```

Fig. 7B

```
         F  E  S  I  N  N  T  V  P  T  A  S  M  C  L  I  K
7619  AATTCAGAAATATTATTAGTTACTGGAGTAGCGGACATACATAATATTTT

N  N  E  F  N  A  L  K  I  L  K  K  Y  I  P  T
7669  ATTATTTTCGAAATTTGCTAATTTTATTAATTTTTTATAAATAGGAGTAA

F  N  R  E  N  N  D  K  K  V  T  R  S  I  L  K  H
7719  AATTTCTTTCGTTATTATCTTTTTTAACAGTTCTTGATATTAATTTATGA

V  E  D  I  I  L  L  R  S  K  K  N  L  S  S  E
7769  ACTTCGTCTATTATTATTAGTAATCTACTTTTTTTATTAAGAGAACTTTC

I  S  R  Y  I  N  N  F  K  D  L  S  S  S  D
7819  TATAGATCTATATATATTATTAAATTTATCTAAACTAGATGACGAATCAT

Y  Y  I  F  K  I  N  S  T  D  S  I  Y  S  R  I  T
7869  AATATATAAATTTTATATTACTGGTATCTGATATATATGATCTTATAGTA

N  L  W  P  D  I  Y  L  S  K  K  I  F  I  L  I  I
7919  TTTAACCAAGGATCTATGTATAATGATTTTTTAATAAATATTAAAATTAT

W  R  P  F  L  E  K  I  Y  K  I  I  Y  V  A  T
7969  CCATCTTGGAAATAATTCTTTTATATATTTATAATATACACAGCAGTTA

L  T  K  G  M  G  T  D  W  F  L  L  M  S  N  L  N
8019  ATGTTTTCCCATACCAGTATCCCAAAATAATAACATACTATTCAAATTT

K  L  G  I  F  I  R  S  V  F  Y  Q  Y  D  Q  L  T
8069  TTTAATCCTATGAATATTCTACTTACAAAATATTGATAATCTTGTAATGT

I  E  T  N  T  I  N  N  M  I  K  N  P  L  H  Q
8119  AATTTCAGTATTTGTAATATTATTCATAATTTTATTAGGCAAATGTTGTG

T  K  D  L  A  Y  N  I  H  K  G  V  I  S  D  L  A
8169  TTTTATCAAGTGCATAATTTATATGTTTACCAACAATAGAATCTAATGCA

< AmEPV NPH I
        F  M
8219  AACATTTAGTTATATAAAAAATAATATTTATATTAACTTAAGATGTTTCA

8269  TTAATTTTATGTCTGTGATGTGGAGTTAAAACCCAAGATATTGATATATC

8319  TATATCATTAATTCTTCTTTTGAATCTATGTCTATCAATCGCAAATTTAT

8369  CCCAGTATAATTTTCGAGTTTGTTTTGCAGCATATAACCAAACATACATA

8319  ATGTGGAGTTTTGGTGGTTCGGATGAAAAGCGTACTTTT    8457
```

ENTOMOPOXVIRUS SPHEROIDIN GENE SEQUENCES

This invention was made with Government support under Grant No. R01 AI15722-12 awarded by the National Institutes of Health and NIH Training Grant T32 AI-07110. The Government has certain rights in this invention.

CROSS-REFERENCE TO A RELATED APPLICATION

This is a continuation-in-part of PCT application WO/92/14818, which is a continuation-in-part of U.S. application Ser. No. 07/827,685, filed Jan. 30, 1992, now abandoned, which is a continuation-in-part of U.S. application Ser. No. 07/657,584, filed Feb. 19, 1991, now abandoned.

FIELD OF THE INVENTION

This invention relates generally to the field of recombinantly-produced proteins and specifically to novel, recombinant Entomopoxvirus genes, proteins, protein regulatory sequences and their uses in expressing heterologous genes in transformed hosts.

BACKGROUND OF THE INVENTION

Poxviruses are taxonomically classified into the family Chordopoxvirinae, whose members infect vertebrate hosts, e.g., the Orthopoxvirus vaccinia, or into the family Entomopoxvirinae. Very little is known about members of the Entomopoxvirinae family other than the insect host range of individual members. One species of Entomopoxvirus (EPV) is the *Amsacta moorei* Entomopoxvirus (AmEPV), which was first isolated from larvae of the red hairy caterpillar *Amsacta moorei* (Roberts and Granados [1968] *J. Invertebr. Pathol.* 12:141–143). AmEPV is the type species of genus B of EPVs and is one of three known EPVs which will replicate in cultured insect cells (R. R. Granados et al. [1976] "Replication of *Amsacta moorei* Entomopoxvirus and *Autographa californica* Nuclear Polyhedrosis Virus in Hemocyte Cell Lines from *Estigmene acrea*," in *Invertebrate Tissue Culture Applications in Medicine, Biology, and Agriculture,* E. Kurstak and K. Maramorosch (ed.), Academic Press, New York, pp. 379–389; T. Hukuhara et al. [1990] *J. Invertebr. Pathol.* 56:222–232; and Sato, T. [1989] "Establishment of Eight Cell Lines from Neonate Larvae of Torticids (Lepidoptera), and Their Several Characteristics Including Susceptibility to Insect Viruses," in *Invertebrate Cell Systems Applications,* J. Mitsuhashi (ed.), Vol. II, CRC Press, Inc., Boca Raton, Fla., pp. 187–198).

AmEPV is one of the few insect poxviruses which can replicate in insect cell culture; AmEPV is unable to replicate in vertebrate cell lines. The AmEPV double-stranded DNA genome is about 225 kb and is unusually A+T rich (18.5% G+C) (W. Langridge, H. R., et al. [1977] *Virology* 76:616–620). Recently, a series of restriction maps for AmEPV were published (Hall, R. L., et al. [1990] *Arch. Virol.* 110:77–90). No DNA homology to vaccinia has been detected (Langridge, W. H. [1983] *J. Invertebr. Pathol.* 42:77–82; Langridge, W. H. [1984] *J. Invertebr. Pathol.* 43:41–46).

The viral replication cycle of AmEPV resembles that of other poxviruses except for the appearance of occluded virus late in infection. For AmEPV, once a cell is infected, both occluded and extracellular virus particles are generated. The mature occlusion body particle, which is responsible for environmentally protecting the virion during infection, consists of virus embedded within a crystalline matrix consisting primarily of a single protein, spheroidin. Spheroidin, the major structural protein of AmEPV, has been reported to be 110 kDa in molecular weight and to consist of a high percentage of charged and sulfur-containing amino acids (Langridge and Roberts [1982] *J. Invertebr. Pathol.* 39:346–353).

Another insect virus is the baculovirus. Like baculoviruses, a characteristic feature of entomopoxviruses is the amalgamation of virions within environmentally stable occlusion bodies. It is this occluded form of the virus that is primarily responsible for dissemination to other insects. While the major protein (polyhedrin) of baculovirus occlusions is quite similar between viruses, it has been reported that the major occlusion body protein (spheroidin) of two group B entomopoxviruses, *Amsacta moorei* (AmEPV) and *Choristoneura biennis* (CbEPV) is quite different both in terms of amino acid sequence and coding capacity of the corresponding spheroidin genes (115 and 47 kDa for AmEPV and CbEPV, respectively).

The entomopoxviruses and the role of occlusion bodies have recently been reviewed by Arif and Kurstak (Arif, B. M., E. Kurstak, E. [1991] "The entomopoxviruses," In *Viruses of Invertebrates* (E. Kurstak, Ed.), pp. 179–195, Marcel Dekker, Inc., New York) and Goodwin et al. (Goodwin, R. H., R. J. Milner, C. D. Beaton [1991] "Entomopoxvirinae," In *Atlas of Invertebrate Viruses* (J. R. Adams and J. R. Bonami, Eds.), pp. 259–285, CRC Press, Inc., Boca Raton ). The gene which encodes the AmEPV spheroidin, a 115 kDa protein, has been identified and sequenced (Hall, R. L., R. W. Moyer [1991] *J. Virol.* 65, 6516–6527; Banville, M., F. Dumas, F., S. Trifiro, B. Arif, C. Richardson [1992] *J. Gen. Virol.* 73, 559–566). The AmEPV gene was also mapped and found to be located at the 3' end of a nucleoside triphosphate phosphohydrolase gene (NPH I or NTPase I, Hall and Moyer [1991], supra). The spheroidin gene of *Choristoneura biennis* entomopoxvirus (CbEPV) has been reported to be derived from a gene capable of encoding a 47 kDa protein (Yuen, L., J. Dionne, B. Arif, C. Richardson [1990] *Virology* 175:427–433.). A comparison of the sequence of the two spheroidins shows no relationship between the two encoded proteins.

We have investigated the spheroidin genes of *Choristoneura biennis, Choristoneura fumiferana,* and *Amsacta moorei* viruses. Our results indicate, in contrast to published results, that the initial Choristoneura EPV spheroidin assignment is likely incorrect and that the Choristoneura spheroidin is instead a highly conserved homolog of the AmEPV spheroidin.

The use of viruses and virus proteins in eukaryotic host-vector systems has been the subject of a considerable amount of investigation and speculation. Many existing viral vector systems suffer from significant disadvantages and limitations which diminish their utility. For example, a number of eukaryotic viral vectors are either tumorigenic or oncogenic in mammalian systems, creating the potential for serious health and safety problems associated with resultant gene products and accidental infections. Further, in some eukaryotic host-viral vector systems, the gene product itself exhibits antiviral activity, thereby decreasing the yield of that protein.

In the case of simple viruses, the amount of exogenous DNA which can be packaged into a simple virus is limited. This limitation becomes a particularly acute problem when the genes used are eukaryotic. Because eukaryotic genes usually contain intervening sequences, they are too large to fit into simple viruses. Further, because they have many restriction sites, it is more difficult to insert exogenous DNA into complex viruses at specific locations.

Vaccinia virus has recently been developed as a eukaryotic cloning and expression vector (Mackett, M., et al. [1985] *DNA Cloning*, Vol. II, ed. D. M. Glover, Oxford: IRL Press, pp. 191–212; Panicali, D., et al. [1982] *Proc. Natl. Acad. Sci. USA*, 88:5364–5368). Numerous viral antigens have been expressed using vaccinia virus vectors (Paoletti, E., et al. [1984] *Proc. Natl. Acad. Sci. USA* 81:193–197; Piccine, A., et al. [1986] *BioEssays* 5:248–252) including, among others, HBsAg, rabies G protein and the gp120/gp41 of human immunodeficiency virus (HIV). Regulatory sequences from the spruce budworm EPV have been used previously with vaccinia (Yuen, L., et al. [1990] *Virology* 175:427–433).

Additionally, studies with vaccinia virus have demonstrated that poxviruses have several advantageous features as vaccine vectors. These include the ability of poxvirus-based vaccines to stimulate both cell-mediated and humoral immunity, minimal cost to mass produce vaccine and the stability of the lyophilized vaccine without refrigeration, ease of administration under non-sterile condition, and the ability to insert at least 25,000 base pairs of foreign DNA into an infectious recombinant, thereby permitting the simultaneous expression of many antigens from one recombinant.

There exists a need in the art for additional viral compositions and methods for use in expressing heterologous genes in selected host cells, and in performing other research and production techniques associated therewith.

BRIEF SUMMARY OF THE INVENTION

This invention pertains to novel vectors useful for producing proteins via the expression of a heterologous gene in a novel expression system. More particularly, this invention relates to methods for incorporating a selected heterologous gene (also referred to as exogenous DNA) into a poxvirus genome to produce a recombinant expression vector capable of expression of the selected gene in a host cell.

The expression systems described herein utilize novel structural and/or regulatory DNA elements from Entomopoxvirus genomes. For example, according to the subject invention, the entomopoxvirus spheroidin gene and/or the thymidine kinase gene can be used as the location for the insertion of exogenous DNA. These Entomopoxvirus genes have been discovered to be attractive sites for insertion of heterologous genes because it is possible to transfer the strongly expressed spheroidin gene, or the thymidine kinase gene, as an expression cassette, not only in insect cells, but for use in vertebrate poxviruses such as vaccinia and swinepox virus.

Another aspect of the subject invention pertains to the use of the entomopoxvirus spheroidin or thymidine kinase gene regulatory sequences in other virus vector systems to enhance the performance of those systems. Thus, the subject invention further pertains to the use of regulatory elements from entomopoxvirus to construct novel chimeric vaccines and expression systems which are functional across genera of mammalian poxviruses.

As one aspect, the invention provides novel Entomopoxvirus polynucleotide sequences, free from other viral sequences with which the Entomopoxvirus sequences are associated in nature. Specifically, the subject invention provides nucleotide sequences of Entomopoxvirus spheroidin and thymidine kinase genes, including flanking sequences and regulatory sequences. In particular embodiments, the spheroidin DNA sequence is that which occurs in the *Choristoneura biennis*, *Choristoneura fumiferana*, or *Amsacta moorei* Entomopoxviruses. Also specifically exemplified is the *Amsacta moorei* Entomopoxvirus thymidine kinase nucleotide sequence. As explained more fully herein, fragments and variants of the exemplified sequences are within the scope of the subject invention. Fragments and variants can be any sequence having substantial homology with the exemplified sequences so long as the fragment or variant retains the utility of the exemplified sequence. One specific type of variant pertains to spheroidin or tk genes from Entomopoxviruses other than those specifically exemplified herein. As described herein, for example, the current inventors have discovered that the spheroidin genes are highly conserved among different species of Entomopoxvirus. Specifically exemplified herein are three different Entomopoxviruse spheroidin genes having a high degree of homology. Other such spheroidin variants or tk variants from other Entomopoxviruses could be readily located and used by the ordinarily skilled artisan having the benefit of the subject application.

As another aspect, the present invention provides recombinant polynucleotide sequences comprising a sequence encoding an Entomopoxvirus spheroidin protein and/or its regulatory sequences, or a variant or fragment of the spheroidin sequence, linked to a second polynucleotide sequence encoding a heterologous gene. One embodiment of such a polynucleotide sequence provides a spheroidin promoter sequence operably linked to a heterologous gene to direct the expression of the heterologous gene in a selected host cell. Another embodiment provides a sequence encoding a spheroidin protein linked to the heterologous gene in a manner permitting expression of a fusion protein. Still another embodiment provides the heterologous gene inserted into a site in a spheroidin gene so that the heterologous gene is flanked on both termini by spheroidin sequences.

Yet a further aspect of the invention provides a recombinant polynucleotide sequence encoding an Entomopoxvirus tk gene and/or its regulatory sequences, or a variant or fragment thereof, linked to a second polynucleotide sequence encoding a heterologous gene. One embodiment of this polynucleotide sequence provides the tk promoter sequence operably linked to the heterologous gene to direct the expression of the heterologous gene in a selected host cell. Another embodiment provides the sequence encoding the tk protein linked to the heterologous gene in a manner permitting expression of a fusion protein. Still another embodiment provides the heterologous gene inserted into a site in the tk gene so that the heterologous gene is flanked on both termini by tk sequences.

Another aspect of the invention pertains to Entomopoxvirus spheroidin polypeptides, fragments thereof, or analogs thereof, optionally fused to a heterologous protein or peptide. Also provided is an Entomopoxvirus tk polypeptide, fragments thereof, or analogs thereof, optionally linked to a heterologous protein or peptide.

Yet another aspect of the invention is provided by recombinant polynucleotide molecules which comprise one or more of the polynucleotide sequences described above. This molecule may be an expression vector or shuttle vector. The molecule may also contain viral sequences originating from a virus other than the Entomopoxvirus which contributed a spheroidin or tk polynucleotide sequence, e.g., vaccinia.

In another aspect, the present invention provides a recombinant virus comprising a polynucleotide sequence as described above. Also provided are host cells infected with one or more of the described recombinant viruses.

The present invention also provides a method for producing a selected polypeptide comprising culturing a selected host cell infected with a recombinant virus, as described above, and recovering said polypeptide from the culture medium.

As a final aspect, the invention provides a method for screening recombinant host cells for insertion of heterologous genes comprising infecting the cells with a recombinant virus containing a polynucleotide molecule comprising the selected heterologous gene sequence linked to an incomplete spheroidin or tk polynucleotide sequence or inserted into and interrupting the coding sequences thereof so that the heterologous gene is flanked at each termini by an Entomopoxvirus spheroidin or tk polynucleotide sequence. The absence of occlusion bodies formed by the expression of a spheroidin protein in the spheroidin-containing cell indicates the integration of the heterologous gene. Alternatively, the absence of the thymidine kinase function, i.e., resistance to methotrexate or a nucleotide analogue of methotrexate, formed by the integration of the inactive thymidine kinase sequence indicates the insertion of the heterologous gene.

Other aspects and advantages of the present invention are described further in the following detailed description of embodiments of the present invention.

BRIEF DESCRIPTION OF THE SEQUENCES

SEQ ID NO. 1 is the DNA sequence of the *Amsacta moorei* Entomopoxvirus spheroidin gene and flanking sequences.

SEQ ID NO. 2 is the amino acid sequence encoded by the G1L ORF.

SEQ ID NO. 3 is the amino acid sequence encoded by the G2R ORF.

SEQ ID NO. 4 is the amino acid sequence encoded by the G3L ORF.

SEQ ID NO. 5 is the amino acid sequence encoded by the G4R ORF.

SEQ ID NO. 6 is the deduced amino acid sequence of the spheroidin protein.

SEQ ID NO. 7 is the amino acid sequence encoded by the G6L ORF.

SEQ ID NO. 8 is the DNA sequence of the *Amsacta moorei* Entomopoxvirus thymidine kinase (tk) gene and flanking sequences.

SEQ ID NO. 9 is a small peptide of 66 amino acids potentially encoded by ORF Q1.

SEQ ID NO. 10 is the amino acid sequence encoded by the Q3 ORF.

SEQ ID NO. 11 is the deduced amino acid sequence of the tk protein.

SEQ ID NO. 12 is the synthetic oligonucleotide designated RM58.

SEQ ID NO. 13 is the synthetic oligonucleotide designated RM82.

SEQ ID NO. 14 is the synthetic oligonucleotide designated RM83.

SEQ ID NO. 15 is the synthetic oligonucleotide designated RM92.

SEQ ID NO. 16 is the synthetic oligonucleotide designated RM118.

SEQ ID NO. 17 is the synthetic oligonucleotide designated RM165.

SEQ ID NO. 18 is the synthetic oligonucleotide designated RM03.

SEQ ID NO. 19 is the synthetic oligonucleotide designated RM04.

SEQ ID NO. 20 is the synthetic oligonucleotide designated RM129.

SEQ ID NO. 21 is the spheroidin gene coding sequence spanning nucleotides #3080 through #6091 of SEQ ID NO. 1.

SEQ ID NO. 22 is a fragment of the spheroidin gene spanning nucleotides #2781 through 3191 of SEQ ID NO. 1 which is likely to contain the promoter sequence.

SEQ ID NO. 23 is the G2R ORF.

SEQ ID NO. 24 is the G4R ORF.

SEQ ID NO. 25 is the G1L ORF.

SEQ ID NO. 26 is the G3L ORF.

SEQ ID NO. 27 is the G6L ORF.

SEQ ID NO. 28 is the tk gene coding sequence spanning nucleotides #234 through #782 of SEQ ID NO. 8.

SEQ ID NO. 29 is a fragment of the tk gene spanning nucleotides #783 through #851 of SEQ ID NO. 8.

SEQ ID NO. 30 is a fragment spanning nucleotides #750 through #890 of SEQ ID NO. 8 which is likely to contain the promoter sequence.

SEQ ID NO. 31 is the Q1 ORF.

SEQ ID NO. 32 is the Q3 OFR.

SEQ ID NO. 33 is a fragment included within the sequence spanning nucleotides #2274 through #6182 of SEQ ID NO. 1 containing the entire spheroidin open reading frame and some flanking sequences.

SEQ ID NO. 34 is a polypeptide cleavage product according to the subject invention.

SEQ ID NO. 35 is a polypeptide cleavage product according to the subject invention.

SEQ ID NO. 36 is a polypeptide cleavage product according to the subject invention.

SEQ ID NO. 37 is the peptide sequence encoded by the RM58 probe.

SEQ ID NO. 38 is a nucleotide fragment spanning nucleotides #4883 through #4957 of SEQ ID NO. 1.

SEQ ID NO. 39 is a nucleotide fragment spanning nucleotides #3962 through #4012 of SEQ ID NO. 1.

SEQ ID NO. 40 is a nucleotide fragment spanning nucleotides #4628 through #4651 of SEQ ID NO. 1.

SEQ ID NO. 41 is the AmEPV NPHI nucleotide sequence shown in FIG. 7.

SEQ ID NO. 42 is the AmEPV NPHI amino acid sequence from FIG. 7. This sequence is in the order opposite that shown in the Figure.

SEQ ID NO. 43 is the CbEPV nucleotide sequence shown in part A of FIG. 6.

SEQ ID NO. 44 is the CbEPV amino acid sequence shown in part B of FIG. 6.

SEQ ID NO. 45 is the CfEPV nucleotide sequence shown in part A of FIG. 6.

SEQ ID NO. 46 is the CfEPV amino acid sequence shown in part B of FIG. 6.

SEQ ID NO. 47 is the CbEPV amino acid sequence corresponding to amino acids 211 to 221 of AmEPV.

SEQ ID NO. 48 is the CbEPV amino acid sequence corresponding to amino acids 682 to 691 of AmEPV.

SEQ ID NO. 49 is the CbEPV amino acid sequence corresponding to amino acids 726–736 of AmEPV.

SEQ ID NO. 50 is the sequence of RM206.
SEQ ID NO. 51 is the sequence of RM212.
SEQ ID NO. 52 is the sequence of RM58.
SEQ ID NO. 53 is the sequence of RM75.
SEQ ID NO. 54 is the sequence of RM76.
SEQ ID NO. 55 is the sequence of RM78.
SEQ ID NO. 56 is the sequence of RM79.
SEQ ID NO. 57 is the sequence of RM82.
SEQ ID NO. 58 is the sequence of RM83.
SEQ ID NO. 59 is the sequence of RM87.
SEQ ID NO. 60 is the sequence of RM91.
SEQ ID NO. 61 is the sequence of RM92.
SEQ ID NO. 62 is the sequence of RM93.
SEQ ID NO. 63 is the sequence of RM95.
SEQ ID NO. 64 is the sequence of RM118.
SEQ ID NO. 65 is the sequence of RM169.
SEQ ID NO. 66 is the sequence of RM170.

BRIEF DESCRIPTION OF THE DRAWINGS

FIG. 2 provides the AmEPV DNA sequence of the *Amsacta moorei* Entomopoxvirus spheroidin gene and flanking sequences (SEQ ID NO. 1), the deduced amino acid sequences of the spheroidin protein (SEQ ID NO. 6), and five additional open reading frames (ORFs). The complete sequence of the G6 ORF is not shown in this figure but is provided in SEQ ID NO. 1.

FIG. 3 provides the DNA sequence of the *Amsacta moorei* Entomopoxvirus thymidine kinase (tk) gene and flanking sequences (SEQ ID NO. 8), the deduced amino acid sequences of the tk protein (SEQ ID NO. 11), and two additional ORFs.

FIG. 4 is a schematic map of an AmEPV fragment illustrating the orientation of the spheroidin ORF on the physical map and indicating homologies.

FIG. 5 shows the location of the AmEPV spheroidin specific oligonucleotide primers used in PCR to identify an AmEPV spheroidin-like gene in Choristoneura EPV DNAs. The arrowheads over the numbers in the diagram represent oligonucleotide primers. The arrowhead base shows the approximate starting point of the primer, and the 5' to 3' direction is shown by the direction of the arrowhead. Primers from the upper line were paired with various primers from the lower line as shown in Table 2 for PCR reactions. The sequences of the primers are shown in Table 2.

FIG. 6 shows sequences of corresponding regions of the spheroidin-like gene of CbEPV and CfEPV and the spheroidin of AmEPV. Panel A shows the AmEPV spheroidin sequence and PCR product sequences derived from CbEPV and CfEPV DNA using RM58 as the sequencing primer for the 1 kb PCR products resulting from the AmEPV spheroidin specific primer pair RM58-RM118 (Table 2) and either CbEPV or CfEPV DNA. The alignment of the Choristoneura EPV sequences with bases 4044–4278 of AmEPV spheroidin is shown. The predicted amino acid sequences from the sequences shown in Panel A are shown in Panel B. Identity is shown by vertical lines and two degrees of conserved changes are indicated by periods and colons. Panel C shows CbEPV spheroidin amino acid sequences derived from protein microsequencing of 3 lys-c endoprotease fragments. Corresponding AmEPV spheroidin sequence and amino acid position numbers are shown.

FIG. 7 shows the sequence of the 5' end of the AmEPV NPH I gene including the deduced amino acids. The base numbers represent the extension of the sequence shown in FIG. 2, which includes the partial AmEPV NPH I (NTPase I) gene. The sequence in FIG. 1 ends at base 6768. The base numbers correspond to those in FIG. 8.

DETAILED DESCRIPTION OF THE INVENTION

Figure 1:
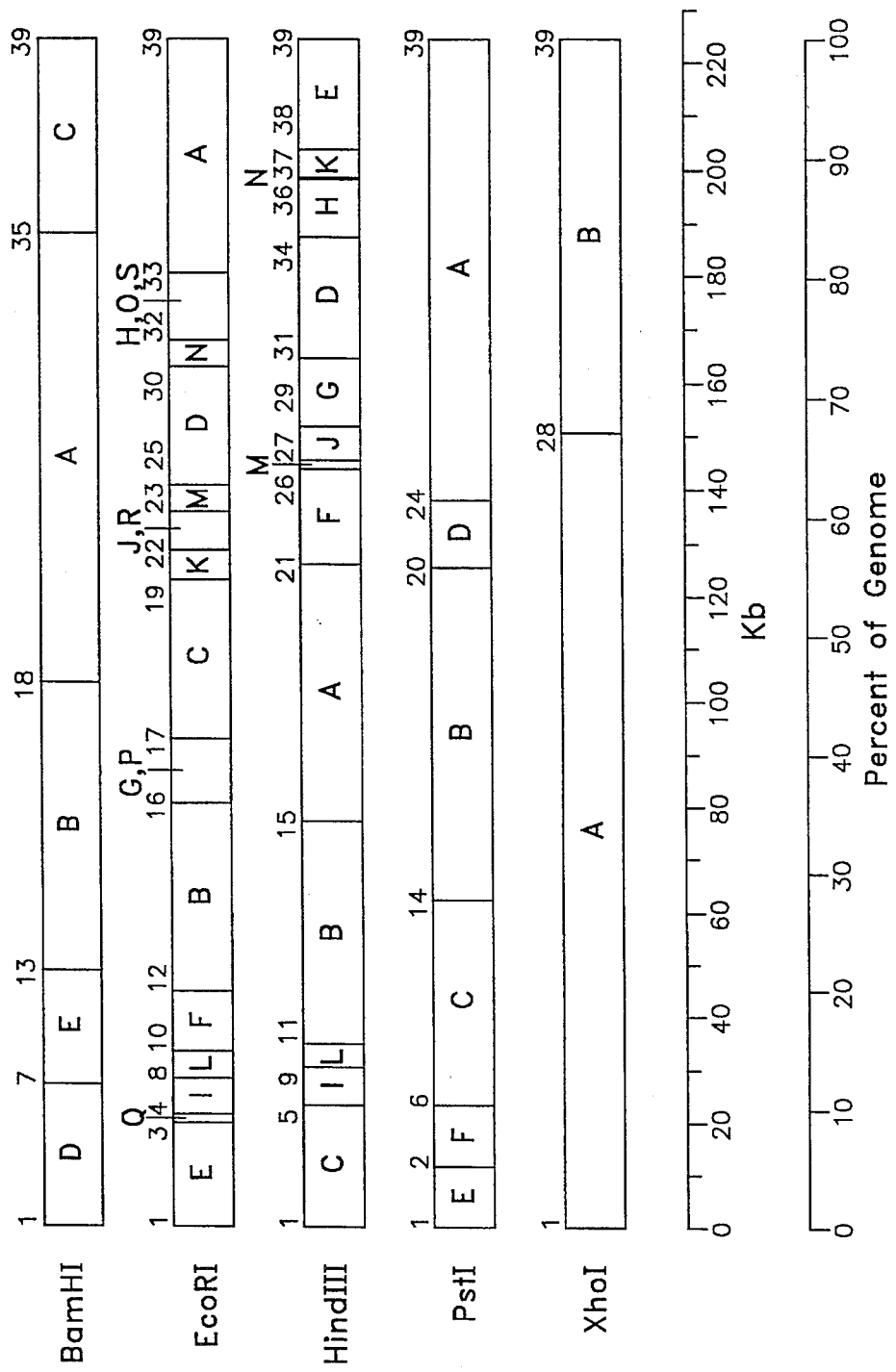
FIG. 1 is a physical map of AmEPV illustrating restriction fragments thereof and showing the spheroidin gene just to the fight of site #29 in the HindIII-G fragment.

The present invention provides novel Entomopoxvirus (EPV) polynucleotide sequences free from association with other viral sequences with which they naturally associated. Recombinant polynucleotide vectors comprising the sequences, recombinant viruses comprising the sequences, and host cells infected with the recombinant viruses are also disclosed herein. These compositions are useful in methods of the invention for the expression of heterologous genes and production of selected proteins in both insect and mammalian host cells.

Novel polynucleotide sequences of the invention encode EPV spheroidin genes and/or flanking sequences, including sequences which provide regulatory signals for the expression of the gene. The invention also provides novel polynucleotide sequences encoding an EPV thymidine kinase (tk) gene and/or its flanking sequences. The polynucleotide sequences of this invention may be either RNA or DNA sequences. More preferably, the polynucleotide sequences of this invention are DNA sequences.

Specifically disclosed by the present invention are spheroidin polynucleotide sequences obtainable from the *Amsacta moorei* Entomopoxvirus (AmEPV), *Choristoneura biennis* Entomopoxvirus (CbEPV), and *Choristoneura fumiferana* Entomopoxvirus (CfEPV). Also specifically exemplified is a tk polynucleotide sequence obtained from AmEPV. While these species are exemplified for practice of the methods and compositions of this invention, utilizing the techniques described herein, substantially homologous sequences may be obtained by one of ordinary skill in the art from other Entomopoxvirus species.

The AmEPV spheroidin DNA sequence, including flanking and regulatory sequences, is reported in FIG. 2 as spanning nucleotides # 1 through 6768 (SEQ ID NO. 1). Within this sequence, the spheroidin gene coding sequence spans nucleotides #3080 through #6091 (SEQ ID NO. 21). A fragment which is likely to contain the promoter sequences spans nucleotides #2781 through #3199 (SEQ ID NO. 22). Other regions of that sequence have also been identified as putative coding regions for other structural or regulatory genes associated with spheroidin. These other fragments of interest include the following sequences: the G2R ORF, which is nucleotides #1472 through #2151 (SEQ ID NO. 23) encoding the amino acid sequence shown in SEQ ID NO. 3; the G4 ORF, which is nucleotides #2502 through #2987 (SEQ ID NO. 24) encoding the amino acid sequence shown in SEQ ID NO. 5; and the following sequences transcribed left to right on FIG. 2: the G1L ORF, which is nucleotides #65 through #1459 (SEQ ID NO. 25) encoding the amino acid sequence shown in SEQ ID NO. 2; the G3L ORF, which is nucleotides #2239 through #2475 (SEQ ID NO. 26) encoding the amino acid sequence shown in SEQ ID NO. 4; and the G6 ORF, which includes nucleotides #6277 through #6768 (SEQ ID NO. 27) encoding the amino acid sequence shown in SEQ ID NO. 7. These ORFs are identified in FIG. 2. It should be noted that the full length of the G6 ORF extends beyond nucleotide #6768, is shown in SEQ ID NO. 1 and FIG. 7, and is discussed more fully below.

The AmEPV ORF G4R (SEQ ID NO. 24) which encodes G4R (SEQ ID NO. 5) is immediately upstream of the spheroidin gene has significant homology to the capripoxvirus HM3 ORF. A homolog of the HM3 ORF is found in vaccinia virus just upstream of a truncated version of the cowpox virus ATI gene. Therefore, the microenvironments in this region are similar in the two viruses. Two other ORFs relate to counterparts in vaccinia virus. These ORFs include the 17 ORF of the vaccinia virus HindIII-I fragment (17) (Schmitt, J. F. C., et al. [1988] *J. Virol.* 62:1889–1897) which relates to the AmEPV G1L ORF (SEQ ID NO. 25) and the NTPase I (NPH I) ORF of the HindIII-D fragment which relates to the AmEPV G6L ORF (SEQ ID NO. 27) (Broyles, S. S., et al. [1987] *J. Virol.* 61:1738–1742; and Rodriguez, J. F., et al. [1986] *Proc. Natl. Acad. Sci. USA* 83:9566–9570). The genomic location of the AmEPV ORFs compared with that of the vaccinia virus ORFs suggests that the arrangement of essential "core genes," which are centrally located and colinear in many, if not all, of the vertebrate poxviruses on a more macroscopic scale, is quite different in the insect virus.

As set out in detail in the accompanying examples below, the spheroidin gene of AmEPV was identified through direct microsequencing of the protein, and the results were used for the design of oligonucleotide probes. Transcription of the spheroidin gene is inhibited by cycloheximide, suggesting it is a late gene. Consistent with this prediction are the observations that spheroidin transcripts were initiated within a TAAATG motif (See FIG. 2, nucleotide #3077–3082) and that there is a 5' poly(A) sequence, both characteristic of late transcripts.

The isolation and sequencing of the CbEPV and CfEPV spheroidin genes are also described in detail below.

The AmEPV thymidine kinase (tk) DNA sequence, including flanking and regulatory sequences, is reported in FIG. 3, as spanning nucleotides #1 through #1511 (SEQ ID NO. 8). Within this sequence, the tk gene coding sequence spans nucleotides #234 through #782 (SEQ ID NO. 28) (transcribed right to left on FIG. 3). Another fragment of interest may include nucleotides #783 through #851 (SEQ ID NO. 29) of that sequence or fragments thereof. A fragment likely to contain the promoter regions spans nucleotides #750 through #890 (SEQ ID NO. 30). Other regions of that sequence have also been identified as putative coding regions for other structural or regulatory genes associated with tk. These other fragments of interest include the following sequences (transcribed left to right on FIG. 3: ORF Q1, which is nucleotides #18 through #218 (SEQ ID NO. 31) encoding the amino acid sequence shown in SEQ ID NO. 10); and ORF Q3, which is nucleotides #852 through #1511 (SEQ ID NO. 32) encoding the amino acid sequence shown in SEQ ID NO. 10.

The location of the AmEPV tk gene maps in the EcoRI-Q fragment near the left end of the physical map of the AmEPV genome (FIG. 1) (see also, Hall, R. L., et al. [1990] *Arch. Virol.* 110:77–90, incorporated herein by reference). Because of the orientation of the gene within the AmEPV genome, transcription of the gene is likely to occur toward the terminus. There are believed to be similar tk genes, or variations thereof, in other systems, including mammalian systems. As set out in detail in the examples below, the tk gene of AmEPV was identified through direct microsequencing of the protein, and the results were used for the design of oligonucleotide probes.

The term "polynucleotide sequences" when used with reference to the invention can include the entire EPV spheroidin or tk genes with regulatory sequences flanking the coding sequences. The illustrated AmEPV sequences are also encompassed by that term. Also included in the definition are fragments of the coding sequences with flanking regulatory sequences. The definition also encompasses the regulatory sequences only, e.g., the promoter sequences, transcription sites, termination sequences, and other regulatory sequences.

Sequences of the invention may also include all or portions of the spheroidin or tk genes linked in frame to a heterologous gene sequence. Additionally, polynucleotide sequences of the invention may include sequences of the spheroidin or tk genes into which have been inserted a foreign or heterologous gene sequence, so that the EPV sequences flank the heterologous gene sequence.

Polynucleotide sequences of this invention also include sequences which are capable of hybridizing to the sequences of FIGS. 2 and 3, under stringent conditions. Also sequences capable of hybridizing to the sequences of FIGS. 2 and 3 under non-stringent conditions may fall within this definition providing that the biological or regulatory characteristics of the sequences of FIGS. 2 and 3, respectively, are retained. Examples of stringent and non-stringent conditions of hybridization are conventional (see, e.g., Sambrook et al. [1989] *Molecular Cloning. A Laboratory Manual,* 2d edition, Cold Spring Harbor Laboratory, Cold Spring Harbor, N.Y.).

Similarly, polynucleotide sequences of this invention also include variants, including allelic variations (naturally-occurring base changes in the EPV species population which may or may not result in an amino acid change) of DNA sequences encoding the spheroidin or tk protein sequences or other ORFs or regulatory sequences illustrated in FIGS. 2 and 3. Similarly, DNA sequences which encode spheroidin or tk proteins of the invention but which differ in codon sequence due to the degeneracies of the genetic code or variations in the DNA sequences which are caused by point mutations or by induced modifications to, for example, enhance a biological property or the usefulness of a desired polynucleotide sequence encoded thereby are also encompassed in the invention.

Utilizing the sequence data in FIGS. 2 or 3, as well as the denoted characteristics of spheroidin or thymidine kinase, it is within the skill of the art to obtain other DNA sequences encoding these polypeptides. For example, the structural gene may be manipulated by varying individual nucleotides, while retaining the same amino acid(s), or varying the nucleotides, so as to modify the amino acids, without loss of utility. Nucleotides may be substituted, inserted, or deleted by known techniques, including, for example, in vitro mutagenesis and primer repair.

The structural gene may be truncated at its 3'-terminus and/or its 5'-terminus. It may also be desirable to ligate a portion of the polypeptide sequence to a heterologous coding sequence, and thus to create a fusion peptide.

The polynucleotide sequences of the present invention may be prepared by a variety of techniques well known to those skilled in the art. The sequences may be prepared synthetically or can be derived from viral RNA or from available cDNA-containing plasmids by chemical and genetic engineering techniques or combinations thereof which are standard in the art.

The Entomopoxvirus proteins—spheroidin, thymidine kinase and their respective regulatory sequences, as described herein—may be encoded by polynucleotide sequences that differ in sequence from the sequences of FIGS. 2 and 3 due to, for example, natural allelic or species variations. Thus, the terms spheroidin or tk polypeptides also refer to any of the naturally occurring sequences and various analogs, e.g., processed or truncated sequences or fragments, including the mature spheroidin or tk polypeptides and mutant or modified polypeptides or fragments that retain the same utility and preferably have homology to FIG. 2 or 3, respectively, of at least 75%, more preferably 90%, and most preferably 95%.

Another aspect of the present invention is provided by the proteins encoded by the EPV spheroidin and tk polynucleotide sequences. Putative amino acid sequences of the two EPV proteins as well as additional putative proteins encoded by the ORFs of these sequences which are identified in FIGS. 2 and 3, respectively. EPV spheroidin has no significant amino acid homology to any previously reported protein, including the polyhedrin protein of baculovirus. We have found that both spheroidin and tk are nonessential proteins, which makes them desirable as sites for insertion of exogenous DNA.

Comparison of the AmEPV tk amino acid sequence with other tk genes reveals that the AmEPV tk gene is not highly related to any of the vertebrate poxvirus tk genes (43.4 to 45.7%). The relatedness of the vertebrate tk proteins to AmEPV is still lower (39.3 to 41.0%), while African Swine Fever (ASF) showed the least homology of all the tk proteins tested (31.4%). Although ASF has many similarities to poxviruses, and both ASF and AmEPV infect invertebrate hosts, the tk genes indicate little commonality and/or indication of common origin stemming from invertebrate hosts.

The spheroidin and thymidine kinase polypeptide sequences may include isolated naturally-occurring spheroidin or tk amino acid sequences identified herein or deliberately modified sequences which maintain the biological or regulatory functions, or other utility, of the AmEPV polypeptides, respectively identified in FIGS. 2 and 3. Therefore, provided that the utilities of these polypeptides are retained in whole or part despite such modifications, this invention encompasses the use of all amino acid sequences disclosed herein as well as variants thereof retaining spheroidin or tk utility. Similarly, proteins or functions encoded by the other spheroidin or tk ORFs may include sequences containing amino acid modifications but which retain their regulatory or other biological functions, or other utility.

Examples of such modifications include polypeptides with amino acid variations from the natural amino acid sequence of Entomopoxvirus spheroidin or thymidine kinase; in particular, conservative amino acid replacements. Conservative replacements are those that take place within a family of amino acids that are related in their side chains.

Genetically encoded amino acids are generally divided into four families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cystine, serine, threonine, tyrosine. Phenylalanine, tryptophan, and tyrosine are sometimes classified jointly as aromatic amino acids. For example, it is reasonable to expect that an isolated replacement of a leucine with an isoleucine or valine, an aspartate with a glutamate, a threonine with a serine, or a similar conservative replacement of an amino acid with a structurally related amino acid will not have a major effect on biological activity, especially if the replacement does not involve an amino acid at an active site of the polypeptides.

As used herein, the term "polypeptide" refers to a polymer of amino acids and does not refer to a specific length of the product; thus, peptides, oligopeptides, and proteins are included within the definition of polypeptide. The phrase "polypeptide and variants thereof" includes post-expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

The proteins or polypeptides of the present invention may be expressed in host cells and purified from the cells or media by conventional means (Sambrook et al., supra).

This invention also relates to novel viral recombinant polynucleotide molecules or vectors, which permit the expression of heterologous genes in a selected host cell. Such a polynucleotide vector of the invention comprises the polynucleotide sequence encoding all or a portion of the spheroidin or tk gene, the RNA polymerase from a selected poxvirus, and the polynucleotide sequence encoding a desired heterologous gene. Preferably, the sequence includes the regulatory region, and most preferably, the promoter region, of either the EPV spheroidin or tk gene. In addition, the source of the polymerase is not limited to EPV; rather, any poxvirus RNA polymerase may be utilized.

Therefore, the viral vectors may contain other viral elements contributed by another poxvirus, either vertebrate or invertebrate, with the only EPV sequences being provided by the presence of the EPV spheroidin or tk gene sequences, or fragments thereof. Numerous conventional expression viral vectors and expression systems are known in the art. Particularly desirable vectors systems are those of vertebrate or invertebrate poxviruses. The Entomopoxvirus spheroidin and tk gene regulatory sequences may be used in other virus vector systems which contain a poxvirus RNA polymerase to enhance the performance of those systems, e.g., in vaccinia vectors. Methods for the construction of expression systems, in general, and the components thereof, including expression vectors and transformed host cells, are within the art. See, generally, methods described in standard texts, such as Sambrook et al., supra. The present invention is therefore not limited to any particular viral expression system or vector into which a polynucleotide sequence of this invention may be inserted, provided that the vector or system contains a poxvirus RNA polymerase.

The vectors of the invention provide a helper independent vector system, that is, the presence or absence of a functional spheroidin or tk gene in a poxvirus contributing elements to the vector, e.g., contributing the RNA polymerase, does not affect the usefulness of the resulting recombinant viral vector. Because both spheroidin and tk are non-essential genes, the viral vectors of this invention do not require the presence of any other viral proteins, which in helper-dependent systems are contributed by additional viruses to coinfect the selected host cell.

Selected host cells which, upon infection by the viral vectors will permit expression of the heterologous gene, include insect and mammalian cells. Specifically, if the viral vector comprises the EPV spheroidin or tk gene sequences of the invention inserted into any member of the family Entomopoxvirinae, e.g., EPVs of any species, the host cell will be limited to cells of insects normally infected by EPVs. If the viral vector comprises the EPV spheroidin or tk gene sequences of the invention inserted into a vertebrate poxvirus, such as vaccinia or swinepox, the host cells may be selected from among the mammalian species normally infected by the wild-type vertebrate poxvirus. Most desirably, such mammalian cells may include human cells, rodent cells and primate cells, all known and available to one of skill in the art.

According to one aspect of the subject invention, therefore, vectors of the present invention may utilize a fragment of the polynucleotide sequence of EPV spheroidin, particularly the promoter and ancillary regulatory sequences which are responsible for the naturally high levels of expression of the gene. Desirably, spheroidin sequences may be found within the sequence of FIG. 2 (SEQ ID NO. 1), more particularly within the region of nucleotides # 2781 through 3199 (SEQ ID NO. 22). Smaller fragments within that region may also provide useful regulatory sequences. The desired spheroidin promoter sequence can be utilized to produce large quantities of a desired protein by placing it in operative association with a selected heterologous gene in viral expression vectors capable of functioning in either a vertebrate or invertebrate host cell.

As used herein, the term "operative association" defines the relationship between a regulatory sequence and a selected protein gene, such that the regulatory sequence is capable of directing the expression of the protein in the appropriate host cell. One of skill in the art is capable of operatively associating such sequences by resort to conventional techniques, Where the spheroidin polynucleotide sequence in the vector contains all or a portion of the spheroidin coding sequence in association with, or linked to, the heterologous gene, the resulting protein expressed in the host cell may be a fusion protein consisting of all or a portion of the spheroidin protein and the heterologous protein. Where the spheroidin polynucleotide sequence in the vector does not contain sufficient coding sequence for the expression of a spheroidin protein or peptide fragment, the heterologous protein may be produced alone.

In an analogous manner, the promoter and regulatory sequences of tk (FIG. 3 SEQ ID NO. 8) may be employed in the construction of an expression vector to drive expression of a heterologous protein, or a fusion protein, in a selected known expression system. These tk regulatory sequences are desirably obtained from the sequence of FIG. 3 (SEQ ID NO. 8), particularly in the fragment occurring between nucleotide #750 through 890 (SEQ ID NO. 30). Smaller fragments within that region may also provide useful regulatory sequences.

An advantage of the use of the novel EPV spheroidin or tk promoter sequences of this invention is that these regulatory sequences are capable of operating in a vertebrate poxvirus (e.g., vaccinia)-mammalian cell expression vector system. For example, the strong spheroidin promoter can be incorporated into the vaccinia virus system through homologous recombination. Unlike the promoter for the baculovirus polyhedrin gene, the promoter for the EPV spheroidin gene can be utilized directly in the vaccinia or swinepox virus expression vector.

To construct a vector according to the present invention, the spheroidin or tk polynucleotide sequence may be isolated and purified from a selected Entomopoxvirus, e.g., AmEPV, and digested with appropriate restriction endonuclease enzymes to produce a fragment comprising all or part of the spheroidin or tk gene. Alternatively such a fragment may be chemically synthesized.

Still alternatively, the desired AmEPV sequences may be obtained from bacterial cultures containing the plasmids pRH512, pMEGtk-1 or pRH7. The construction of the plasmid pRH512 is described in the examples below. This plasmid contains the 4.51 kb BglII fragment AmEPV DNA sequence inserted into a BamHI site in the conventional vector pUC9. The plasmid pRH7 was constructed by digesting AmEPV genomic DNA, obtained as described in Example 1, with Bsp1286I, and the resulting fragments with HaeII. T4 DNA polymerase is employed to blunt end the AmEPV DNA and the fragment containing the spheroidin gene is ligated to the large fragment of a SmaI digested pUC9 fragment. This fragment contains the entire spheroidin open reading frame and some flanking sequence, included within the nucleotide sequence spanning #2274–6182 (SEQ ID NO. 33) of FIG. 2. The construction of plasmid pMEGtk-1 comprising the regulatory sequences of the tk gene as well as the structural gene is described below in the Example 8. It was constructed by inserting the EcoRI-Q fragment of AmEPV into the conventional vector pUC18.

Bacterial cultures containing plasmids pRH512, pMEG tk-1, and pRH7 have been deposited in the American Type Culture Collection, 12301 Parklawn Drive, Rockville, Md., USA. The deposited cultures are as follows:

| Culture | Accession No. | Deposit Date |
| --- | --- | --- |
| E. coli SURE strain (Stratagene) pMEG-tk1 | ATCC 68532 | February 26, 1991 |
| E. coli SURE strain (Stratagene) pRH512 | ATCC 68533 | February, 26 1991 |
| E. coli SURE strain (Stratagene) pRH7 | ATCC 68902 | January 28, 1992 |

The plasmids can be obtained from the deposited bacterial cultures by use of standard procedures, for example, using cleared lysate-isopycnic density gradient procedures, and the like.

These ATCC deposits were made under conditions that assure that access to the cultures will be available during the pendency of this patent application to one determined by the Commissioner of Patents and Trademark to be entitled thereto under 37 CFR 1.14 and 35 USC 122. The deposits will be available as required by foreign patent laws in countries wherein counterparts of the subject application, or its progeny, are filed. However, it should be understood that the availability of a deposit does not constitute a license to practice the subject invention in derogation of patent rights granted by government action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least 30 (thirty) years after the date of deposit or for the enforceable life of any patent which may issue disclosing the cultures. The depositor acknowledges the duty to replace the deposit(s) should the depository be unable to furnish a sample when requested, due to the condition of a deposit. All restrictions on the availability to the public of the subject culture deposits will be irrevocably removed upon the granting of a patent disclosing them.

The molecular biology procedures referred to herein in describing construction of the vectors of this invention are standard, well-known procedures. The various methods employed in the preparation of the plasmid vectors and transformation or infection of host organisms are well-known in the art. These procedures are all described in, for example, Sambrook et al., cited above. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

Because the AmEPV genome has no known unique restriction sites into which selected genes may be effectively introduced in a site-specific manner so as to be under the control of the spheroidin or tk promoter sequences, such restriction sites must be introduced into desired sites in the selected EPV polynucleotide sequence. For example, the unique BstB1 site located at nucleotide #3172 downstream from the start of the spheroidin gene is the closest site to genetically engineer a usable insertion sequence for cloning. Therefore, restriction sites closer to the initiating Met of the spheroidin gene must be deliberately inserted.

Methods for the insertion of restriction sites are known to those of skill in the art and include, the use of an intermediate shuttle vector, e.g., by cloning the EPV sequence into the site of an appropriate cloning vehicle. It will be recognized by those skilled in the art that any suitable cloning vehicle may be utilized provided that the spheroidin or tk gene and flanking viral DNA may be functionally incorporated.

A spheroidin shuttle vector may be constructed to include elements of the spheroidin structural gene, a cloning site located or introduced in the gene to enable the selected heterologous gene to be properly inserted into the viral genome adjacent to, and under the control of, the spheroidin promoter, and flanking viral DNA linked to either side of the spheroidin gene to facilitate insertion of the spheroidin-foreign gene-flanking sequence into another expression vector. The presence of flanking viral DNA also facilitates recombination with the wild type Entomopoxvirus, allowing the transfer of a selected gene into a replicating viral genome.

The shuttle vectors may thereafter be modified for insertion of a selected gene by deleting some or all of the sequences encoding for spheroidin or tk synthesis near the respective transcriptional start sites. Examples of such sites in spheroidin are nucleotides #3077 and 3080 and in tk includes nucleotide #809. Conventional procedures are available to delete spheroidin or tk coding sequences.

As an alternative to or in addition to the restriction site, a variety of synthetic or natural oligonucleotide linker sequences may be inserted at the site of the deletion. A polynucleotide linker sequence, which may be either a natural or synthetic oligonucleotide, may be inserted at the site of the deletion to allow the coupling of DNA segments at that site. One such linker sequence may provide an appropriate space between the two linked sequences, e.g., between the promoter sequence and the gene to be expressed. Alternatively, this linker sequence may encode, if desired, a polypeptide which is selectively cleavable or digestible by conventional chemical or enzymatic methods. For example, the selected cleavage site may be an enzymatic cleavage site, including sites for cleavage by a proteolytic enzyme, such as enterokinase, factor Xa, trypsin, collegenase and thrombin. Alternatively, the cleavage site in the linker may be a site capable of being cleaved upon exposure to a selected chemical, e.g. cyanogen bromide or hydroxylamine. The cleavage site, if inserted into a linker useful in the sequences of this invention, does not limit this invention. Any desired cleavage site, of which many are known in the art, may be used for this purpose. In another alternative, the linker sequence may encode one or a series of restriction sites.

It will be recognized by those skilled in the art who have the benefit of this disclosure that linker sequences bearing an appropriate restriction site need not be inserted in place of all or a portion of the spheroidin structural sequence, and that it would be possible to insert a linker in locations in the Entomopoxvirus genome such that both the sequence coding for the selected polypeptide and the spheroidin structural sequence would be expressed. For instance, the sequence coding for the selected polypeptide could be inserted into the tk gene in place of all or a portion of the tk structural sequence and under the transcriptional control of the tk promoter.

Polymerase chain reaction (PCR) techniques can also be used to introduce convenient restriction sites into the EPV DNA, as well as to amplify specific regions of the EPV DNA. These techniques are well known to those skilled in this art. See, for example, *PCR Protocols: A Guide to Methods and Applications,* M. A. Innis, D. H. Gelfand, J. J. Sninsky, and T. J. White, (1990).

By use of these techniques, a variety of alternative modified shuttle vectors into which a selected gene or portion thereof may be incorporated may be suitably utilized in the present invention.

As one embodiment of the invention, therefore, the polynucleotide sequence, described above, may be used as a shuttle vector to transfer a selected heterologous gene to a selected virus. In this embodiment, the polynucleotide sequence encoding the EPV spheroidin gene or EPV tk gene, or a fragment thereof, is linked to a heterologous gene. The polynucleotide sequence further contains a flanking region on either side of the spheroidin-heterologous gene or tk-heterologous gene to enable ready transfer into a selected virus. This resulting construct is termed a cassette. Such a flanking region may be derived from EPV, or alternatively, may be complementary to the target virus. For example, if it is desirable to insert a selected heterologous gene into a vaccinia virus to create a recombinant virus, one would utilize flanking regions complementary to the targeted vaccinia virus. Similarly if the heterologous gene is inserted within the EPV spheroidin or tk gene, so that the selected EPV regulatory sequence and heterologous gene are flanked by the EPV gene's own sequences, this cassette may be used for transfer into a wild type EPV having homologous sequences to the flanking sequences.

The insertion or linkage of the foreign gene into the tk or spheroidin sequences of the present invention or the linkage of flanking sequences foreign to the spheroidin or tk genes may be accomplished as described above. The vectors of the subject invention may use cDNA clones of foreign genes, because poxvirus genes contain no introns, presumably as a consequence of a totally cytoplasmic site of infection.

In accordance with standard cloning techniques, any selected gene may be inserted into the vector at an available restriction site to produce a recombinant shuttle vector. Virtually any gene of interest could be inserted into the vectors described herein in order to obtain high expression of the desired protein. The, spheroidin gene product may be useful as a particulate biological carrier for foreign gene antigens. Thus, a foreign gene fused to the spheroidin gene may be useful as a method to produce a foreign protein attached to an effective vaccine carrier. Restriction sites in the fragment may thereafter be removed so as to produce a preferred spheroidin or tk shuttle vector, having one or more cleavage or cloning sites located in the 3' direction downstream from the spheroidin promoter sequence. Thus, the present invention is not limited by the selection of the heterologous gene.

Alternatively, a vector of this invention may comprise a heterologous gene which is inserted into all or a portion of the EPV spheroidin or tk protein encoding sequence to interrupt the protein's natural processing. However, when the vector is transferred to another virus which contains a wild-type spheroidin or tk gene, expression of the inserted heterologous gene is obtained. Thus, the Entomopoxvirus spheroidin gene (FIG. 2; SEQ ID NO. 1) and/or the tk gene (FIG. 3; SEQ ID NO. 8) can be used as the location for the insertion of exogenous (heterologous) DNA in any of the above-mentioned expression systems. A shuttle vector so constructed may be useful as a marker for research and production techniques for identifying the presence of successfully integrated heterologous genes into the selected expression system.

The tk gene is a particularly desirable site for insertion of a selected heterologous gene. Unlike spheroidin, tk is produced early in infection and in lesser quantities. Additionally, many poxviruses possess tk genes which may be sufficiently homologous to the EPV tk to provide easy recombination. For example, in vaccinia virus expression systems for mammalian cells, the vaccinia tk gene is a common insertion site. Therefore, the use of this gene is particularly desirable for construction of a shuttle vector to shuttle selected genes directly between vector systems. More specifically, a foreign gene may be desirably inserted into the EPV tk gene sequence between nucleotide #460 and #560 (See FIG. 3).

Insertion of cassettes containing foreign genes into wild-type poxviruses can be accomplished by homologous recombination. The homologous recombination techniques used to insert the genes of interest into the viruses of the invention are well known to those skilled in the art. The shuttle vectors, when co-infected into host cells with a wild-type virus, transfer the cassette containing the selected gene into the virus by homologous recombination, thereby creating recombinant virus vectors.

Expression of a selected gene is accomplished by infecting susceptible host insect cells with the recombinant viral vector of this invention in an appropriate medium for growth. An EPV expression vector is propagated in insect cells or insects through replication and assembly of infectious virus particles. These infectious vectors can be used to produce the selected gene in suitable insect cells, thus facilitating the efficient expression of the selected DNA sequence in the infected cell. If the EPV spheroidin gene (or tk gene)-heterologous gene fragment is inserted into a vertebrate poxvirus by the same methods as described above, the recombinant virus may be used to infect mammalian cells and produce the heterologous protein in the mammalian cells.

For example, a gene inserted into the tk site of a vaccinia virus system could be transferred directly to the tk locus of an Entomopoxvirus vector of the subject invention or vice versa. This shuttling could be accomplished, for example, using homologous recombination. Similarly insertion of a selected gene into the spheroidin gene or tk gene in a viral vector permits the gene to be shuttled into other viruses having homologous spheroidin or tk sequences, respectively.

The following description illustrates an exemplary vector of this invention, employing the gene coding for human β-intefferon (IFN-β) synthesis as the heterologous gene. A DNA fragment containing the IFN-β gene is prepared conventionally with restriction enzyme digested or blunt ended termini and cloned into a suitable site in the AmEPV spheroidin gene, into which a restriction site has been engineered by the methods described above.

The insertion of the IFN-β gene produces a hybrid or fused spheroidin-IFN-β gene capable of producing a fused polypeptide product if only a portion of the spheroidin gene was deleted as described above. If the entire spheroidin structural sequence was deleted, only interferon will be produced. Further, the hybrid gene may comprise the spheroidin promoter, the IFN-β protein coding sequences, and sequences encoding a portion of the polypeptide sequence of the spheroidin protein, provided all such coding sequences are not deleted from the particular shuttle vector utilized.

The resulting shuttle vector contains the AmEPV spheroidin gene sequence coupled to the IFN-β gene. The hybrid spheroidin-IFN-β gene of the recombinant shuttle vector is thereafter transferred into the genome of an appropriate Entomopoxvirus, such as the preferred Entomopoxvirus AmEPV, to produce a recombinant viral expression vector capable of expressing the gene encoding for β-interferon in a host insect cell. Transfer of the hybrid gene to a wild-type virus is accomplished by processes which are well known to those skilled in the art. For example, appropriate insect cells may be infected with the wild type Entomopoxvirus. These infected cells are then transfected with the shuttle vector of the subject invention. These procedures are described, for example, in *DNA Cloning: A Practical Approach*, Vol. II, Edited by D. M. Glover, Chapter 7, 1985. A person skilled in the art could choose appropriate insect cells to be used according to the subject invention. By way of example, salt marsh caterpillars and cultured gypsy moth cells can be used.

During replication of the AmEPV DNA after transfection, the hybrid gene is transferred to the wild-type AmEPV by homologous recombination between the recombinant shuttle vector and AmEPV DNA. Accordingly, a mixture is produced comprising wild-type, nonrecombinant EPVs and recombinant EPVs capable of expressing the IFN-β gene.

While transfection is the preferred process for transfer of the hybrid gene into the EPV genome, it will be understood by those skilled in the art that other procedures may be suitably utilized so as to effect the insertion of the gene into the EPV genome and that recombination may be accomplished between the recombinant shuttle vector and other strains of EPV (or other poxviruses) so long as there is sufficient homology between the sequence of the hybrid gene and the corresponding sequence of the other strain to allow recombination to occur.

The preferred recombinant AmEPV expression vector, comprising a hybrid. spheroidin-IFN-β gene incorporated into the AmEPV genome, can thereafter be selected from the mixture of nonrecombinant and recombinant Entomopoxviruses. The preferred, but by no means only, method of selection is by screening for plaques formed by host insect cells infected with viruses that do not produce viral occlusions. Selection may be performed in this manner because recombinant EPV viruses which contain the spheroidin protein coding sequences interrupted by the heterologous gene are defective in the production of viral occlusions due to the insertional inactivation of the spheroidin gene.

Also, the selection procedure may involve the use of the β-galactosidase gene to facilitate color selection. This procedure involves the incorporation of the E. coli β-galactosidase gene into the shuttle vector and is well known to those skilled in the art. This technique may be of particular value if the exogenous DNA is inserted into the tk gene so that the spheroidin gene is still expressed. It will be recognized by those skilled in the art that alternative selection procedures may also be utilized in accordance with the present invention.

Accordingly, the DNA from a recombinant virus is thereafter purified and may be analyzed with appropriate restriction enzymes, or PCR technology, to confirm that the recombinant AmEPV vector has an insertion of the selected gene in the proper location.

The vectors and methods provided by the present invention are characterized by several advantages over known vectors and vector systems. Advantageously, such EPV viral vectors of the present invention are not oncogenic or tumorigenic in mammals. Also, the regulatory signals governing Amsacta moorei Entomopoxvirus (AmEPV) gene expressions are similar to those of vaccinia. Therefore, it is possible to transfer the strongly expressed spheroidin gene, or the thymidine kinase gene, as an expression cassette, not only in insect cells, but for use in vertebrate poxviruses such as vaccinia and swinepox virus.

Based on reported data with vaccinia, herpes and baculovirus vector systems, which suggest that up to 30 kb can be transferred without disrupting the vector viability, the normal limitation on the amount of exogenous DNA which can be packaged into a virus is not anticipated to be encountered when using the novel EPV vectors and methods of the subject invention.

Another advantage is that for the novel vectors of the subject invention, the transcription and translation of foreign proteins is totally cytoplasmic. Still another advantage lies in the expression power of the EPV spheroidin regulatory sequences, which when in operative association with a heterologous gene in a vector of this invention, can be used to produce high levels of heterologous protein expression in the selected host cell.

The EPV vectors of this invention and methods for employing them to express selected heterologous proteins in insect or mammalian cells, as described above, are characterized by the advantage of replication in insect cells, which avoids the use of mammalian viruses, thereby decreasing the possibility of contamination of the product with mammalian virus. The expression system of this invention is also a helper independent virus expression vector system. These two characteristics are shared by known baculovirus expression systems. However, as shown in Table 1, the EPV expression vector system (EEVS) using the vectors of this invention has some important distinguishing features compared to the baculovirus expression systems (BEVS).

TABLE 1

| Differences between EEVS and BEVS | | |
|---|---|---|
| | EEVS | BEVS |
| Site of replication: | cytoplasm | nucleus |
| Virus family: | Poxviridae | Baculoviridae |
| Sites for insertion of foreign genes: | spheroidin & thymidine kinase (tk) | polyhedrin & p10 |
| Shuttle possibilities between vertebrate and insect systems: | (Orthopoxviruses) (Leporipoxviruses) (Suipoxviruses) (Avipoxviruses) | No mammalian counterparts. Baculovirus is not known to contain a tk gene. Polyhedrin is not found in mammalian systems. |

The present invention also provides a method for screening recombinant host cells for insertion of heterologous genes by use of the recombinant viral polynucleotide molecules of this invention. The viral molecules containing the selected heterologous gene sequence linked to the polynucleotide sequence encoding less than all of the Entomopoxvirus spheroidin protein. The heterologous gene may be linked to the spheroidin or tk regulatory sequences in the absence of the complete coding sequences, or it may be inserted into the spheroidin or tk gene coding sequences, thus disrupting the coding sequence. The cell infected with the recombinant vector is cultured under conditions suitable for expression of the heterologous protein, either unfused or as a fusion protein with a portion of the spheroidin sequence. The absence of occlusion bodies which would ordinarily be formed by the expression of the intact spheroidin protein indicates the integration of the heterologous gene.

If the viral vector similarly contained either incomplete or interrupted EPV tk encoding sequence, the absence of thymidine kinase function (e.g., resistance to methotrexate or an analogue thereof) formed by the integration of the inactive thymidine kinase sequence indicates the insertion of the heterologous gene.

Alternatively, if a parent virus is deleted of part of its tk or spheroidin gene, and is thereafter mixed with a viral vector containing intact tk or spheroidin fused to the foreign gene, recombinants would express the methotrexate resistance or produce occlusion bodies, respectively, thus indicating integration of the active tk or spheroidin genes and the foreign gene.

The above-described selection procedures provide effective and convenient means for selection of recombinant Entomopoxvirus expression vectors.

Another embodiment of the present invention involves using novel EPV expression systems of the subject invention for insect control. Control of insect pests can be accomplished by employing the vectors and methods of the invention as described above. For example, a gene coding for an selected insect toxin may be inserted into the viral expression vector under the control of the spheroidin or tk regulatory sequences or within either of the two genes for purposes of recombination into a selected virus having homologous flanking regions.

Genes which code for insect toxins are well known to those skilled in the art. An exemplary toxin gene isolated from Bacillus thuringiensis (B.t.) can be used according to the subject invention. B.t. genes are described, for example, in U.S. Pat. Nos. 4,775,131 and 4,865,981. Other known insect toxins may also be employed in this method.

The resulting EPV vector containing the toxin gene is applied to the target pest or its surroundings. Advantageously, the viral vector will infect the target pest, and large quantities of the toxin will be produced, thus resulting in the control of the pest. Particularly large quantities of the toxin protein can be produced if the regulatory sequences of the Entomopoxvirus spheroidin gene are used to express the toxin.

Alternatively, the spheroidin gene can be left intact and the toxin gene inserted into a different Entomopoxvirus gene such as the tk gene. In this construct, the toxin will be produced by the system and then effectively coated or encapsulated by the natural viral production of spheroidin. This system thus produces a toxin which will advantageously persist in the environment to prolong the availability to the target pest.

In addition to the novel Entomopoxvirus expression vectors and methods for their use described herein, the subject invention pertains to the use of novel regulatory elements from Entomopoxvirus to construct novel chimeric vaccinia and swinepox vaccines and expression systems which are functional across genera of mammalian poxviruses. The polynucleotide sequences of the invention can also be used with viral vaccines, e.g., known vaccinia virus vaccines, to enhance the effectiveness of these vaccines. Such vaccines have been described for use in controlling rabies and other infectious diseases in mammals. Specifically, it is anticipated that the introduction of the EPV spheroidin promoter sequences into known viral vectors which are used to express selected proteins in a mammalian host in vivo may enable the powerful spheroidin promoter to increase expression of the protein in the viral vaccine. This aspect of the invention provides a significant improvement over other expression systems, including the baculovirus expression system (BEVS).

The following examples illustrate the compositions and procedures, including the best mode, for practicing the invention. These examples, should not be construed as limiting. All percentages are by weight and all solvent mixture proportions are by volume unless otherwise noted. The restriction enzymes disclosed herein can be purchased from Bethesda Research Laboratories, Gaithersburg, Md., or New England Biolabs, Beverly, Mass. The enzymes are used according to the instructions provided by the supplier. Klenow fragment of DNA polymerase, T4 polynucleotide kinase, and T4 DNA ligase were obtained from New England Biolabs and Promega.

Example 1

Preparation of AmEPV DNA

The replication of AmEPV has been described previously (Goodwin, R. H., et al. [1990] *J. Invertebr. Pathol.* 56:190–205). The gypsy moth (*Lymantria dispar*) cell line IPLB-LD-652 (Insect Pathology Laboratory, Agricultural Research Service, U.S. Department of Agriculture, Beltsville, Md.) is maintained at 26° to 28° C. in EX-CELL 400 (JRH Biosciences, Lenexa, Kans.) supplemented with 10% fetal bovine serum, 100 U of penicillin, and 100 µg of streptomycin per ml. Other insect cell lines are well known to those skilled in the art and can be used according to the subject invention.

The AmEPV inoculum for cell culturing was from an AmEPV-infected, freeze-dried *E. acrea* larva stored at −70° C. (Hall, R. L., et al. [1990] *Arch. Virol.* 110:77–90). The larva was crushed and macerated in 5 ml of EX-CELL 400 (with penicillin and streptomycin but without fetal bovine serum) to which 0.003 g of cysteine-HCl had been added to prevent melanization. The debris was pelleted at 200×g for 5 minutes, and the supernatant was passed through a 0.45-µm-pore-size filter.

The gypsy moth cells were infected with AmEPV by addition of the inoculum to a preconfluent monolayer of cells (about 0.1 to 1 PFU per cell), with occasional agitation of the dish during the first day. Infected cells were harvested 5 to 6 days postinfection.

AmEPV DNA was prepared from the infected cells by one of two methods. The first method involved in situ digestion of infected cells embedded within agarose plugs, after which the released cellular and viral DNAs were separated by pulsed-field electrophoresis (Bio-Rad CHEF-II-DR system). IPLB-LD-652 cells were infected with first-cell-culture-passage AmEPV. Infected cells were harvested 6 days postinfection by centrifugation at 200 ×g for 5 minutes, rinsed, and resuspended in modified Hank's phosphate-buffered saline (PBS), which contained 15 g of glucose per liter, but no $Ca^{2+}$ or $Mg^{2+}$.

For embedding of the infected cells in agarose plugs, 1% SeaPlaque GTG agarose (prepared in modified Hank's PBS and equilibrated at 37° C.) was mixed 1:1 with infected cells to yield $5\times10^6$ cells per ml in 0.5% agarose. Digestion to release DNA was done by gentle shaking of the inserts in 1% Sarkosyl-0.5M EDTA-1 mg of proteinase K per ml at 50° C. for 2 days (Smith, C. L., et al. [1987] *Methods Enzymol.* 151:461–489). The CHEF-II-DR parameters for DNA separation were 180 V, a pulse ratio of 1, 50 initial and 90 second final pulse times, and a run time of 20 to 25 hours at 4° C. The separating gel was 1% SeaKem GTG agarose in 0.5x TBE buffer (Sambrook et al., supra). Viral DNA bands were visualized by ethidium bromide staining and electroeluted (Allington, W. B., et al. [1978] *Anal. Biochem.* 85:188–196). The recovered DNA was used for plasmid cloning following ethanol precipitation.

The second method of viral DNA preparation used the extracellular virus found in the infected-cell-culture supernatant. The supernatant from 10-day-postinfection cell cultures was clarified by centrifugation at 200×g for 5 minutes. Virus was collected from the supernatant by centrifugation at 12,000×g. Viral pellets were resuspended in 6 ml of 1x TE. DNase I and RNase A (10 and 20 µg/ml final concentrations, respectively) were added, and the mixture was incubated at 37° C. for 30 minutes. The mixture was heated to 50° C. for 15 minutes. SDS and proteinase K (1% and 200 µg/ml, respectively) were then added. The sample was incubated to 50° C. overnight and extracted three times with buffer-saturated phenol and once with SEVAG (Sambrook et al., supra). The DNA was ethanol precipitated and resuspended in 1x TE (pH 8).

For routine virus quantitation, 1 ml of an appropriate virus dilution (prepared in unsupplemented EX-CELL 400) was added to a preconfluent monolayer of cells in a 60 mm culture dish, with intermittent agitation over a 5 hour adsorption period at 26° to 28° C. The virus inoculum was removed, and 5 ml of a 0.75% SeaPlaque agarose (FMC BioProducts, Rockland, Me.) overlay prepared with 2x EX-CELL 400 and equilibrated at 37° C. was added to the monolayer. Plaques were visualized after 5 days of incubation at 26° C. by inspection with a stereomicroscope.

The DNA prepared according to either method was then cut with a variety of restriction endonuclease enzymes, e.g., BamHI, EcoRI, HindIII, PstI and XhoI, generating the various fragments which appear on the physical map of FIG. 1. Hereafter, reference to each restriction fragment will refer to the enzyme and the applicable letter, e.g., BamHI-A through BamHI-E, EcoRI-A through EcoRI-S, etc.

Example 2

Production of Spheroidin Polypeptide

To localize the spheroidin gene, a purified preparation of occlusion bodies (OBs) from infected caterpillars was solubilized and subjected to sodium dodecyl sulfate-polyacrylamide gel electrophoresis (SDS-PAGE) (Laemmli, J. K. [1970] Nature (London) 227:680–685) with a 4% acrylamide stacking gel and a 7.5% separating gel. The acrylamide used to prepare spheroidin for protein microsequencing was deionized with AG501X8 resin (Bio-Rad, Richmond, Calif.). The gels were polymerized overnight at 4° C. For sample preparation, 2x Laemmli sample buffer consisting of 125 mM Tris-HCl (pH 6.8), 4% SDS (w/v), 10% β-mercaptoethanol (v/v), and 20% glycerol (v/v) was used.

OB suspension samples were diluted 1:1 with 2x Laemmli sample buffer and boiled for 5 minutes. Several lanes of an OB protein preparation were separated electrophoretically. The spheroidin protein (113 kDa) was the predominant protein of the purified OBs. Spheroidin within SDS-polyacrylamide gels was tested for glycosylation by periodic acid-Schiff staining (Zacharius, R. M., et al. [1969] Anal. Biochem. 30:149–152).

Following electrophoretic separation, several lanes in the unstained gel were transferred to an Immobilon polyvinylidene difluoride (PVDF) membrane with a Bio-Rad TransBlot apparatus at 90 V for 2 hours in a buffer consisting of 10 mM morpholinepropanesulfonic acid (pH 6.0) and 20% methanol. Spheroidin was visualized on the PVDF membrane by Coomassie blue staining.

The region of the PVDF membrane containing spheroidin was excised from the membrane, and direct protein microsequencing was done with an Applied Biosystems gas-phase sequencer. Microsequencing of the intact protein was unsuccessful, presumably because the N terminus of the protein was blocked.

Cyanogen bromide cleavage was performed on samples of spheroidin eluted from the PVDF membrane to generate internal peptide fragments for sequencing. Major polypeptides of 15, 9, 8, and 6.2 kDa were produced.

Example 3

Sequencing, Hybridizations

All DNA sequencing was done by the dideoxy chain termination method (Sanger, F., et al. [1977] Proc. Natl. Acad. Sci. USA 74:5463–5467) with [$\alpha$-$^{35}$S]dATP and Sequenase (US Biochemical, Cleveland, Ohio). Standard sequencing reactions with Sequenase were carried out in accordance with the instructions of the supplier, US Biochemical.

A reliable amino acid sequence was obtained from the 9, 8, and 6.2 kDa polypeptides produced as described in Example 2. The 8 and 9 kDa polypeptides represented overlapping partial CNBr cleavage products which together yielded the longest continuous amino acid sequence: Met-Ala-(Asn or Arg)-Asp-Leu-Val-Ser-Leu-Leu-Phe-Met-(Asn or Arg)-(?)-Tyr-Val-(Asn? )-Ile-Glu-Ile-Asn-Glu-Ala-Val-(?)(Glu?) (SEQ ID NO. 34). The amino acid sequence obtained from the 6.2 kDa fragment was Met-Lys-Ile-Thr-Ser-Ser-Thr-Glu-Val-Asp-pro-Glu-Tyr-Val-(ThrorIle)-Ser-(Asn?) (SEQ ID NO. 35). A partial sequence for the 15 kDa fragment was also obtained: (Asn?)-Ala-Leu-Phe-(Phe?)(Asn?)-Val-Phe (SEQ ID NO. 36). The question marks in the above sequences indicated undetermined or unconfirmed amino acids. All sequences were ultimately located within the spheroidin gene sequence.

Example 4

Plasmid pRH512

A BglII AmEPV DNA library was prepared by digesting the genomic AmEPV DNA with BglII according to manufacturer's instructions. Plasmid pUC9 (GIBCO; Bethesda Research Labs) was BamHI-digested and phosphatase-treated. The genomic BglII cut AmEPV was shotgun cloned into the BamHI site of pUC9. Escherichia coli SURE (Stratagene, La Jolla, Calif.) was transformed by electroporation with a Bio-Rad Gene Pulser following the instructions provided by the manufacturer with the shotgun ligation, containing a variety of recombinant plasmids. Mini-preparations of plasmids were made by a conventional alkaline lysis procedure (Sambrook et al., supra). These plasmids were cut with EcoRI-SalI to release the insert and run on a gel. The resulting plasmid DNA was southern blotted to a nylon membrane, producing a number of clones.

Among the fragments produced from the restriction enzyme digestions of the genomic DNA was a 4.4 BglII fragment and an EcoRI-D fragment. In order to locate a desirable clone from among those produced above, the sequence derived from the 6.2 kDa CNBr fragment was used to design a degenerate oligonucleotide for use as a hybridization probe to locate the spheroidin gene in a clone. The nucleotide sequence of this probe called RM58 (SEQ ID NO. 12) was GAAGT7GATCC7GAATATGT where 5 represents A or G, 6 represents C or T, and 7 represents A, G, C, or T. The peptide sequence of the probe was: Glu-Val-Asp-Pro-Glu-Tyr (SEQ ID NO. 37).

The DNA probe was radiolabeled either with [$\alpha$-$^{32}$P] dCTP by the random oligonucleotide extension method (Feinberg, A. P., et al. [ 1983] Anal Biochem. 132:6–13) or with [$\gamma$-$^{32}$P]ATP and T4 polynucleotide kinase (Sambrook et al., supra). These same procedures were used for all other oligonucleotide probes described below. Both types of probes were purified by passage through spun columns of Sephadex G-50.

Southern transfer was done with Hybond-N (Amersham); the transferred DNA was fixed to the membrane by UV cross-linking. Southern hybridization was performed both with transferred DNA including the restriction fragments described above, as well as the BglII library of AmEPV DNA cloned into BamHI-digested plasmid pUC9 as described above. Hybridization with the oligonucleotide probe was done at 37° or 45° C. with BLOTTO (Sambrook et al., supra) and was followed by two washes at room temperature with 0.3M NaCl -0.06M Tris (pH 8)-2 mM EDTA for 5 minutes.

The RM58 probe (SEQ ID NO. 12) hybridized to the 4.4 kb BglII fragment and the EcoRI-D fragment of AmEPV DNA (See FIG. 1). A plasmid produced by the shotgun cloning, recombinant pRH512 (a BglII 4.56 kb fragment inserted into the BamHI site of pUC9 which contains about 1.5 kb of the 5' end of the spheroidin gene) was also identified by this hybridization with the RM58 oligonucleotide (SEQ ID NO. 12).

The 4.51 kb pRH512 BglII insert was isolated, radiolabeled as described above, and hybridized back to various AmEPV genomic digests as follows. The DNA—DNA hybridization was done at 65° C. with BLOTTO (Sambrook et al., supra) and was followed by two washes at room temperature with 0.3M NaCl -0.06M Tris (pH 8)-2 mM EDTA for 5 minutes, two washes for 15 minutes each at 65° C. but with 0.4% SDS added, and two washes at room temperature with 0.03M NaCl-0.06M Tris (pH 8)-0.2 mM EDTA. Hybridization was observed to the BamHI-A, EcoRI-D, HindIII-G and -J, PstI-A, and XhoI-B fragments of AmEPV DNA. The results of these hybridizations indicated that the 4.51 kb fragment in pRH512 was substantially identical to the 4.4 kb fragment produced by BglII digestion of genomic DNA.

The 4.51 kb BglII insert of pRH512 was thereafter sequenced by two procedures. One is the double-stranded plasmid sequencing method (Hattori, M., et al. [1986]*Anal. Biochem.* 152:232–238) performed with "miniprep" (Sambrook et al., supra) DNA and 1 pmol of universal, reverse, or custom-designed oligonucleotide primer in each sequencing reaction. Nested exonuclease II deletions (Henikoff, S. [1987]*Methods Enzymol.* 155:156–165) were used to sequence plasmid pRH512 according to this method. Deletions were made from the universal primer end. For making these deletions, the DNA was cut with EcoRI, filled in with α-thiophosphate dNTPs (Putney, S. D., et al. [1981]*Proc. Natl. Acad. Sci. USA* 78:7350–7354) by use of the Klenow fragment of *E. coli* DNA polymerase, cut with SmaI, and treated with exonuclease III. Samples were removed every 30 seconds, re-ligated, and used to transform *E. coli* SURE cells by electroporation. Sequencing reactions were carried out with the universal primer.

When a primer complementary to that sequence was prepared and used to sequence back through the RM58 binding site (bases 3983 to 4002), the generated sequence, when translated, yielded the amino acid sequence generated from microsequencing the 6.2 kDa CNBr polypeptide fragment.

A second sequencing method was performed using a combination of M12 shotgun sequencing with standard and universal and reverse M13 primers into M13 phage to permit single-stranded sequencing as follows. Plasmid pRH512 was sonicated to produce random fragments, repaired with bacteriophage T4 DNA polymerase, and these fragments were shotgun cloned into SmaI-cut M13mp19 (GIBCO). Plaque lifts were screened with a radiolabeled probe prepared from the 4.5 kb insert found in pRH512 to identify appropriate clones for shotgun single stranded sequencing (see, e.g., Sambrook et al., supra). Sequencing of the BglII insert of pRH512 isolated it to nucleotides #0 to 4505, thus extending the sequence 5' and 3' to the spheroidin gene (FIG. 2).

Example 5

Obtaining Additional AmEPV Sequence

A DraI AmEPV DNA library was prepared by digesting genomic DNA with DraI. These DraI fragments were shotgun cloned into SmaI-digested, phosphatase-treated vector M13mp19. Preparations of M13 virus and DNA were made by standard procedures (Sambrook et al., supra). Ligation and heat shock transformation procedures were performed conventionally (Sambrook et al., supra), resulting in the shotgun cloned fragments being transformed into the bacterial strain, *E. coli* UT481 (University of Tennessee) or the SURE strain.

Standard PCR (Innis et al., supra) with 400 ng of genomic AmEPV DNA as a template was used to prepare a probe to identify a 586 bp DraI clone from nitrocellulose filter replicas (plaque lifts) (Micron Separations, Inc.) of the M13 shotgun library of DraI-cut AmEPV fragments. This was done to isolate a clone spanning a central unsequenced region of the spheroidin gene. The standard PCR primers used for this reaction were RM92 (SEQ ID NO. 15) (GCCTGGTTGGGTAACACCTC) and RM118 (SEQ ID NO. 16) (CTGCTAGATTATCTACTCCG). This sequencing revealed that there was a single HindIII site at base 931 and that the 3' end of the spheroidin open reading frame (ORF) was truncated (FIG. 2).

The technique of inverse polymerase chain reaction (PCR) (Innis, M. A., et al., [1990] *PCR protocol, a guide to methods and applications,* Academic Press, Inc. San Diego, Calif.) was used with ClaI-digested AmEPV DNA fragments which were ligated into a circle, to prepare a probe to identify clones containing a flanking sequence or to verify the absence of an intervening sequence between adjacent clones. The primers used in inverse PCR were RM82 and RM83, which were taken from the pRH512 sequence. The sequence of RM82 (SE0 ID NO. 13) was TTTCAAATTAACTGGCAACC and that of RM83 (SEQ ID NO. 14) was GGGATGGATTTTAGATTGCG.

The specific PCR reaction conditions for 34 cycles were as follows: 30 seconds at 94° C. for denaturation, 30 seconds at 37° C. for annealing, and 1.5 minutes at 72° C. for extension. Finally, the samples were incubated at 72° C. to 8.5 minutes to complete extensions. The concentration of each primer was 1 μM.

The resulting 2.2 kb inverse PCR product was digested with ClaI, and a 1.7 kb fragment was gel purified. The 1.7 kb PCR fragment was sequenced with RM83 as a primer. Additional PCR primers were made to the new sequence as it was identified. The sequencing process employed Sequenase, 5 pmol of each primer, and 10 to 50 ng of template. Prior to being sequenced, the PCR products were chloroform extracted and purified on spun columns (Sambrook et al., supra) of Sephacryl S-400. The DNA sequence was assembled and aligned, and consensus sequence was produced (Staden, R. [1982] *Nucleic Acids Res.* 10:4731–4751). Both strands were completely sequenced; the PCR product sequence was verified by conventional sequence.

The relevant ClaI sites of the 1.7 kb PCR fragment are at positions 3485 and 6165. This fragment was radiolabeled and used as a probe to locate additional clones, i.e., pRH827 (307 bp), pRH85 (1.88 kb), and pRH87 (1.88 kb) from the BglII fragment library. Plasmids pRH85 and pRH87 were sequenced using the same nested exonuclease II deletions and sequencing procedure, as described above for pRH512. Sequencing of the inverse PCR products with custom-designed primers confirmed that plasmids pRH85 and pRH87 represented the same 1.88 kb BglII DNA insert in opposite orientations, but also revealed a missing 80 bp between pRH827 and pRH85. This 80 bp DNA fragment was identified in the DraI fragment, as extending from bases 4543 to 5128 cloned into M13.

The orientation of the spheroidin ORF on the physical map is shown in FIG. 1. It is interesting to note that the 1.7 kb inverse PCR fragment only hybridized to the AmEPV HindIII-G fragment. The amino acid sequence derived from the 8 and 9 kDa overlapping CnBr-generated polypeptides is found from nucleotide positions 4883 to 4957 (SEQ ID NO. 38). That derived from the 6.2 kDa polypeptide is found from nucleotides 3962 to 4012 (SEQ D NO. 39), and that derived from the 15 kDa polypeptide is found from nucleotides 4628 to 465 1 (SEQ ID NO. 40). Therefore, all sequences obtained from protein microsequencing were ultimately found to lie within the spheroidin ORF.

Example 6

Spheroidin Gene Transcription

The start site for spheroidin gene transcription was determined. A primer complementary to the spheroidin gene sequence beginning 65 bp downstream of the predicted initiating methionine was prepared and used for a series of primer extensions.

A. Preparation of RNA and primer extension reactions.

Six 150 mm dishes of subconfluent cells were prepared. The culture media were aspirated, and 2 ml of viral inoculum was added to each dish. The virus concentration was about 0.1 to 1 PFU per cell. The dishes were occasionally agitated during a 3 hour adsorption period. At the end of this period, the cells were rinsed with 5 ml of modified PBS. The media were replaced, and the infected cells were incubated for 72 hours at 27° C. Total RNA from the infected cells was isolated by the guanidinium thiocyanate-cesium chloride procedure (Chirgwin, J. M., et al. [1979] *Biochemistry* 18:5294–5299).

Primer extension reactions were carried out with primer RM165 (SEQ ID NO. 17), a 35-base oligonucleotide (GTTCGAAACAAGTATTTTCATCTTTTAAATAAATC) beginning and ending 100 and 65 bp downstream, respectively, of the initiating methionine codon found in the TAAATG motif. The primer was end labeled with [γ-$^{32}$P] ATP and T4 polynucleotide kinase and purified on a "spun column" (Sambrook et al., supra). For annealing, 40 µg of total infected-cell RNA and $10^6$ cpm of radiolabeled primer were coprecipitated with ethanol. The pellet was resuspended in 25 µl of hybridization buffer (80% formamide, 40 mM piperazine-N,N'-bis(2-ethanesulfonic acid) (pH 6.4), 400 mM NaCl, 1 mM EDTA (pH 8.0)], denatured at 72° C. for 15 minutes, and incubated at 30° C. for 18 hours.

For primer extension, the RNA-primer hybrids were ethanol precipitated, resuspended, and used for five individual reactions. Each reaction contained 8 µg of total infected-cell RNA, 50 mM Tris-HCl, (pH 8.3), 50 mM KCl, 10 mM dithiothreitol, 10 mM MgCl$_2$, 4 U of avian myeloblastosis virus reverse transcriptase (Life Sciences), 8 U of RNasin (Promega), 0.25 mM each deoxynucleoside triphosphate (dNTP), and the appropriate dideoxynucleoside triphosphate (ddNTP), except for a control reaction, which contained no ddNTP. The dNTP/ddNTP ratios were 4:1, 5:1, 5:1, and 2:1, for the C, T, A, and G reactions, respectively. The reactions were carried out at 42° C. for 30 minutes.

One microliter of chase buffer (4 µl of 5 mM dNTP mixture and 1 µl of 20-U/µl reverse transcriptase) was added to each reaction mixture, which was then incubated for an additional 30 minutes at 42° C. Reaction products were separated on a sequencing gel (8% acrylamide containing 7M urea) and visualized by autoradiography. Complementarity was observed until the AAA of the upstream TAAATG motif, indicating that transcription of the gene initiates within the TAAATG element of the proposed late promoter element. Immediately upstream is a 5' tract of noncoded poly(A) on the transcripts. The average length of the poly(A) is greater than 6 bp.

Example 7

Analysis of Spheroidin Sequence

The spheroidin ORF (G5R) was initially identified by sequencing back through the RM58 oligonucleotide primer binding region as described above. Examination of the AmEPV spheroidin gene sequence (ORF G5R) revealed a potential ORF of 3.0 kb capable of encoding 1,003 amino acids or a protein of about 115 kDa. The ORF consists of 29% G+C, in contrast to the 18.5% reported for the entire AmEPV genome (Langridge, W. H. R., R. F. Bozarth, D. W. Roberts [1977] *Virology* 76:616–620). Inspection of the 92 bases upstream of the initiating ATG revealed only 7 G or C residues. Also detected was the presence of known vertebrate poxvirus regulatory sequences within the 92 bp 5' of the spheroidin ORF. Included are three TTTT TNT early gene termination signals and TAAATG, which presumably represents a late transcription start signal used to initiate transcription and translation of the spheroidin gene. Several adjacent translation termination codons are also present within the 92 bp upstream of the spheroidin ORF.

Analysis of the sequence upstream of the spheroidin gene revealed four additional potential ORFs, G1L (SEQ ID NO. 25), G2R (SEQ ID NO. 23), G3L (SEQ ID NO. 26), and G4R (SEQ ID NO. 24), discussed above. The putative amino acid sequences of these ORFs are reported in FIG. 2 (SEQ ID NO. 2, 3, 4 and 5, respectively). No significant homologies were found for the small potential polypeptides encoded by ORF G2R (SEQ ID NO. 23) or G3L (SEQ ID NO. 26). ORF G1L (SEQ ID NO. 25), however, exhibited a significant degree of homology to ORF 17 found within the HindIII-I fragment of vaccinia virus, whose function is unknown. ORF G4R (SEQ ID NO. 24) showed homology to ORF HM3 of capripoxvirus. In vaccinia virus, the ORF HM3 homolog was found very near the site of an incomplete ATI gene. The partial G6L ORF (SEQ ID NO. 27) to the right of the spheroidin gene exhibited good homology to vaccinia virus NTPase I. Much better homology (78.4% identity over 162 amino acids) was found between the partial G6L ORF (SEQ ID NO. 27) and NPH I of CbEPV (Yuen, L., et al. [1991] *Virol.* 182:403–406).

Example 8

Isolation and Sequencing of the AmEPV EcoRI-Q Fragment Containing the tk Gene Sequencing of the EcoRI-Q fragment of genomic AmEPV of Example 1 was performed using techniques described above for spheroidin. The sequencing showed 1511 bp containing two complete and one partial ORF. Analysis of the DNA sequence of ORF Q2 (SEQ ID NO. 28) indicates the sites where the identifying degenerate oligonucleotides (RM03 SEQ ID NO. 18 and RM04 SEQ ID NO. 19) might hybridize. Two oligonucleotides, RM03 and RM04, based on different but strongly conserved regions of the tk genes of several poxviruses and vertebrates (Upton, C., et al. [1986] *J. Virol.* 60:920–927; Boyle, D. B., et al. [1987] *Virology* 156:355–365) were prepared by the methods referred to above. RM03 was the 32-fold degenerate oligonucleotide (SEQ ID NO. 18) GA(T/C)GA(G/A)GG(G/A)GG (G/A)CA(G/A)TT(C/T)TT corresponding to the amino acid residues in the vaccinia tk protein from the aspartic acid at position 82 to the phenylalanine at position 87. RM04 (SEQ ID NO. 19) was (GGNCCCATGTT(C/T)TCNGG with 32-fold degeneracy and corresponded to the region from the glycine at position 11 to the glycine at position 16 in vaccinia. These probes were radiolabeled as described above for the RH58 probe.

The AmEPV thymidine kinase (tk) gene was identified by hybridization with the degenerate oligonucleotide probes RM03 and RM04 to a Southern blot of the EcoRI-digested EPV DNA. The EcoRI band of interest (EcoRI-Q) was isolated, purified, and ligated into a pUC18 vector (GIBCO), previously digested with EcoRI and treated with calf intestinal alkaline phosphatase. Recombinant clones were identified by the size of the insert and by hybridization to the radioactive labeled oligonucleotide probes.

One such clone was called pMEGtk-1. The recombinant clones containing the EcoRI-Q fragment oriented in both directions relative to the pUC18 vector sequences were used for sequencing. Sequential nested deletions were generated by the method of Henikoff, cited above, as described for pRH512. These clones were used for sequencing the entire EcoRI-Q fragment.

Subsequently, these oligonucleotides and another, RM129 is a non-degenerate oligonucleotide GGTGCAAAATCT-GATATTTC (SEQ ID NO. 20) prepared from the ORF Q1, were employed as sequencing primers to confirm their positioning as indicated in ORF Q2 (SEQ ID NO. 28). ORF Q2 potentially encodes for a protein of 182 amino acids (21.2 kDa) (SE0 ID NO. 10). ORF 03 potentially encodes a polypeptide of at least 68 amino acids but is incomplete and is transcribed in the opposite direction from ORF Q2. ORF Q1 (SEQ ID NO. 31) potentially encodes a small peptide of 66 amino acids (7.75 kDa) (SEQ ID NO. 9).

Further analysis of the EcoRI-Q fragment reveals several other points. First, the A+T content is very high (80%). For ORF Q2, the 100 nucleotides upstream of the start codon for translation are 90% A+T. Some potential poxvirus transcription signals were found between ORFs Q1 and Q2. The five bases immediately preceding the start codon for ORF Q1 are TAAATG which comprise a consensus late poxvirus promoter. A potential poxvirus early transcription termination signal sequence (TTTTTAT) is located 2 nt past the translation stop codon of Q2.

The deduced amino acid sequence for the tk encoded by the ORF Q2 of the EcoRI-Q fragment can be compared to the tk genes for the poxviruses swine pox (Schnitzlein, W. M., et al. [1991] *Virol.* 181:727–732; Feller, J. A., et al. [1991] *Virol.* 183:578–585); fowlpox (Boyle et al., supra; Binns, M. M., et al. [1988] *J. Gen. Virol.* 69:1275–1283); vaccinia (Weir, J. P., et al. [1983] *J. Virol.* 46:530–537; Hruby, D. E., et al. [1983] *Proc. Natl. Acad. Sci. USA* 80:3411–3415); variola and monkeypox (Esposito, J. J., et al. [1984] *Virol.* 135:561–567); capripoxvirus (Gershon, P. D., et al. [1989] *J. Gen. Virol.* 70:525–533); Shope fibroma virus (Upton et al., supra); the cellular thymidine kinases of humans (Bradshaw, H. D., et al. [1984] *Mol. Cell. Biol.* 4:2316–2320; Flemington, E., et al. [1987] *Gene* 52:267–277); the tk of mouse (Lin, P. F., et al. [1985] *Mol Cell. Biol.* 5:3149–3156); the tk of chicken (Kwoh, T. J., et al. [1984] *Nucl. Acids Res.* 12:3959–3971); ASF (Blasco, R., et al. [1990] *Virol.* 178:301–304; Martin Hernandez, A. M., et al. [1991] *J. Virol.* 65:1046–1052).

Example 9

Expression of the AmEPV tk Gene in a Vaccinia Virus

The AmEPV tk gene was tested functionally by cloning the gene into a vaccinia virus strain tk⁻ mutant, as follows.

The EcoRI-Q fragment of AmEPV, described above, was inserted in both possible orientations into shuttle plasmid pHGN3.1 (Bloom, D. D., et al. [1991] *J. Virol.* 65:1530–1542) which had been isolated from bacterial cells by the alkaline lysis method. This EcoRI-Q DNA fragment contains the AmEPV tk open reading frame (ORF). The cloning was performed conventionally. The resulting plasmid was designated pHGN3.1/EcoRI-Q.

The plasmid was transfected by Lipofectin (GIBCO) as described specifically below into mammalian cells infected with vaccinia virus. The cells were either rat tk⁻, human 143 tk⁻, or CV-1 cell lines onto which the vaccinia virus VSC8 was propagated. These cells were maintained in Eagle's Minimal Essential Medium with Earle's salts (Massung et al. [1991] *Virol.* 180:347–354, incorporated by reference herein).

The VSC8 vaccinia strain (Dr. Bernard Moss) contains the β-galactosidase gene driven by the vaccinia $P_{11}$ promoter ($P_{11}$-Lac Z cassette) inserted into the vital tk gene. While VSC8 contains an inactive tk gene due to the insertion of the β-galactosidase, portions of the vaccinia tk sequence remain. VSC8 is thus tk⁻ and, upon staining with X-Gal (5-bromo-4-chloro-3-indoyl-β-D-galactopyranoside), will form blue plaques (β-galactosidase positive).

Cells were grog to 80% confluence ($4 \times 10^6$ per 60 mm dish). Lipofectin solution (20 μg of Lipofectin in 50 μl of $dH_2O$) was added to 10 μg plasmid DNA (pHGN3.1/AmEPV EcoRI-Q) in 50 μl of $dH_2O$ and incubated for 15 minutes at room temperature. After a 2 hour period of viral adsorption (m.o.i. of 2, 37° C.), the monolayers were washed three times with serum-free OptiMEM. Three milliliters of serum-free OptiMEM was then added to each 60 mm dish. The Lipofectin/DNA mixture was slowly added dropwise with gentle swirling and incubated an additional 12 to 18 hours at 37° C. Fetal bovine serum was then added (10% final) and the infected cells were harvested at 48 hours postinfection.

Recombinant viruses, containing the EcoRI-Q fragment inserted into the hemagglutinin (HA) gene of vaccinia, were identified by hybridization of AmEPV EcoRI-Q fragments, radioactively labeled by procedures described above, to replicas of nitrocellulose "lifts" of virus plaques from the infected monolayer. Potential recombinants were isolated from replica filters and plaque-purified several times before testing.

The tk of AmEPV exhibits some degree of homology with the tk of vaccinia. To confirm that insertion of the AmEPV tk gene was within the HA gene of vaccinia rather than within residual tk sequences remaining in VSC8, the recombinants were examined by a series of Southern hybridizations to HindIII digests of the various viruses. When DNA from wild-type virus was hybridized to a vaccinia virus tk probe, hybridization was observed exclusively within the ≈5 kb HindIII-J fragment of vaccinia.

When either VSC8 or either of the AmEPV tk containing recombinants was examined using the vaccinia tk probe, hybridization occurred instead to an ≈8 kb fragment consistent with insertion of the ≈3.1 kb β-galactosidase cassette into the TK gene of the HindIII-J fragment. Hybridization of the HindIII digests of the same three viruses to radiolabeled AmEPV EcoRI-Q DNA resulted in hybridization to a large-molecular-weight DNA fragment in the recombinant containing the AmEPV TK gene, which we have shown corresponds to the HindIII-A fragment. These results suggest that insertion of the AmEPV TK gene into vaccinia occurred within the HA gene contained within the large (>23 kb) HindIII-A fragment of the virus as expected. Identical results were observed for VSC8::TKII. It is also interesting to note the lack of hybridization of the vaccinia virus (VV) and AmEPV TK probes to the heterologous poxvirus TK gene under these conditions, even though there is significant sequence homology between the vaccinia and the AmEPV TK genes.

Plaque-purified vaccinia recombinants were tested for growth on human 143 TK⁻cells in the presence of methotrexate. Under these conditions, only $TK^+$ virus will grow and produce plaques. Both recombinants (VSC8::AmEPV TKI and VSC8::AmEPV TKII) representing the two orientations of the AmEPV EcoRI-Q fragment gave plaques in the presence of methotrexate. All plaques from both recombinant viruses which grew in the presence of methotrexate also stained blue upon staining with X-Gal, suggesting that the $TK^+$ phenotype of these recombinants is most likely due to a functional TK gene contained within the AmEPV EcoRI-Q fragment. Since functionality is independent of the orientation of the AmEPV EcoRI-Q fragment, it is plausible that an AmEPV TK gene promotor contained within the EcoRI-Q fragment may function in vaccinia.

Example 10

Orientation of the TK Gene Within the AmEPV Genome

In order to determine the orientation of the Q1, Q2, Q3 ORFs within the EcoRI-Q fragment relative to the genome, a DNA primer-mediated extension reaction was performed. The EcoRI-Q fragment is contained within the PstI-F fragment. An oligonucleotide identical in sequence to bases 182–163 (RM129, SEQ ID NO. 12) was prepared and hybridized to a heat-denatured PstI digest of genomic AmEPV DNA. The partial hybrid was then extended with the Klenow fragment of *E. coli* DNA polymerase in the presence of radiolabeled substrates. Extension will terminate at the end of the PstI-F fragment.

The radiolabeled product was then hybridized to an EcoRI digest of AmEPV DNA. If orientation of the gene is such that the tk ORF reads toward the end of the genome, hybridization would be expected to the EcoRI-E fragment; whereas if the gene is read toward the center of the genome, hybridization would be expected to the EcoRI-I fragment.

The results indicate hybridization not only to the EcoRI-E fragment, but also to the EcoRI-A fragment. These results infer that the orientation of the tk gene is with reading toward the left end of the genome. Hybridization of the run-off extension product also to the EcoRI-A fragment is consistent with the presence of an inverted terminal repetition, common in poxviruses, with identical sequences residing in both the EcoRI-A and the EcoRI-E fragments.

The optimal growth temperature for AmEPV in the laboratory is 28° C., whereas that of the vertebrate poxviruses is 37° C. As described herein, when the AmEPV DNA fragment containing the entire tk gene was cloned into the $tk^-$ strain of vaccinia virus, the recombinant virus was capable of growing at 37° C. in the presence of methotrexate (Sigma), indicative of a $tk^+$ phenotype. This example demonstrates that the Entomopoxvirus tk gene can be successfully transferred into mammalian expression systems, and that AmEPV tk is functionally active over a considerable temperature range.

Example 11

Isolation and Sequencing of CbEPV and CfEPV Spheroidin Genes

Viruses and cell culture. Choristoneura EPVs, CbEPV and CfEPV, occlusion bodies (OBs) were obtained from Dr. Basil M. Arif, Forest Pest Management Institute, Sault Ste. Marie, Ontario, Canada, and can be obtained from other sources as well. The AmEPV OBs were the same as those used previously (Hall and Moyer, 1991). The gypsy moth cell line, IPLB-LD-652, used for AmEPV replication was maintained in EX-CELL 401 (JRH Biosciences, Lenexa, Kan.) supplemented with 10% fetal bovine serum. Wild type cowpox virus, Brighton red strain, was produced in CV-1 cells cultured in Eagle's MEM with Earle's salts.

SDS-PAGE, occlusion body solubilization, and total cell protein preparation. Sodium dodecyl sulfate-polyacrylamide gel electrophoresis (SDS-PAGE) of proteins was with a 4% acrylamide stacking gel and a 7.5% separating gel. For sample preparation, 2X Laemmli sample buffer consisting of 125 mM Tris-HCl (pH 6.8), 4% SDS (wt/vol), 10% β-mercaptoethanol (vol/vol), 20% glycerol (vol/vol), and 0.05% bromphenol blue (wt/vol) was used. Quantitation of OBs was achieved by counting a diluted suspension in a hemocytometer. The OB suspension (varying from $8\times10^6$ to $1\times10^8$ OBs/ml) usually prepared in 1X TE (10 mM Tris-HCl, 1 mM EDTA, pH 8.0), was diluted 1:1 with the 2X Laemmli sample buffer and immediately boiled for 5 or 10 min. For studies designed to assay for spheroidin degradation, the OBs plus sample buffer were left at room temperature for various time periods before boiling. After electrophoretic separation, the proteins were visualized by Coomassie blue staining.

The preparation of total uninfected or infected cell protein for SDS-PAGE utilized a 2X lysis buffer consisting of 160 mM Tris-HCl (pH 9), 4% SDS (wt/vol), 4% β-mercaptoethanol (vol/vol), 10% glycerol (vol/vol), 5M urea, 20 mM EDTA (pH 8), and 0.01% bromphenol blue (wt/vol). Cells were scraped from a 150 mm diameter culture dish using a rubber policeman and centrifuged at 1000×g for 5 min at 4° C. Cells were washed in appropriate cold phosphate buffered saline (PBS) and recentrifuged. Insect cells were harvested in Hank's PBS which contained 15 g glucose per liter. The cell pellets were resuspended in a final volume of 500 μl of PBS which contained 5 μl each per ml of PMSF (phenylmethyl sulfonyl fluoride, 0.1M stock in 95% ethanol) and aprotinin (0.3 mg/ml stock). The cells were probe sonicated on ice for 15 sec., five hundred microliters of 2X lysis buffer was added, and the preparation sonicated as before. Samples were stored at −70° C. and boiled before loading on an SDS-PAGE gel.

Preparation of EPV DNAs. CfEPV DNA was obtained from Dr. Basil M. Arif, Forest Pest Management Institute, Sault Ste. Marie, Ontario, Canada. CbEPV DNA used in the polymerase chain reaction (PCR) studies was prepared directly from occlusion bodies by the agarose in situ method (Hall and Hink, 1990) and extracted by "freeze-squeeze" (Sambrook et al., 1989). AmEPV DNA was prepared from infected LD-652 cell culture by concentrating extracellular virus which was then treated with DNase I and RNase A prior to dissolution of the occlusion bodies by SDS and proteinase K digestion (Gruidl et al., 1992).

PCR Primers and Reactions. PCR, product purification, and dideoxy sequencing were done as described previously (Hall and Moyer, 1991) except that the specific reaction conditions for 34 cycles were 1 min at 94° C. for denaturation, 1 min at 37° C. for annealing, and 2 min at 72° C. for extension. Finally, samples were incubated at 72° C. for 9 min to complete extensions. Typically, 50 to 100 ng of template DNA was used in the PCRs. Custom oligonucleotide primers RM82, RM83, RM92 and RM118 were described previously (Hall and Moyer, 1991). Sequences of these and other AmEPV spheroidin specific PCR primers (5' to 3', base pair numbers from Hall and Moyer, 1991) are summarized in Table 2.

TABLE 2

PCR reactions used in checking Choristoneura EPV DNA for a homolog of the AmEPV spheroidin gene

| AmEPV spheroidin specific primer pair[1] | Expected Product Size (bp) | Appropriate Size Product Observed | |
|---|---|---|---|
| | | CbEPV | CfEPV |
| 12 - 9 | 314 | − | − |
| 12 - 8 | 599 | + | + |
| 12 - 6 | 828 | − | − |
| 12 - 3 | 1047 | − | − |
| 12 - 4 | 1184 | − | − |
| 1 - 4 | 290 | + | + |
| 12 - 11 | 1444 | − | + |
| 1 - 11 | 549 | + | + |
| 2 - 11 | 307 | + | + |
| 12 - 15 | 1542 | − | − |
| 1 - 15 | 648 | + | + |
| 2 - 15 | 378 | + | + |
| 12 - 13 | 1944 | − | − |
| 1 - 13 | 1050 | + | + |
| 2 - 13 | 807 | + | + |
| 5 - 13 | 632 | − | + |
| 7 - 13 | 595 | + | + |
| 14 - 13 | 426 | + | + |
| 10 - 13 | 259 | − | + |

Figure 5:
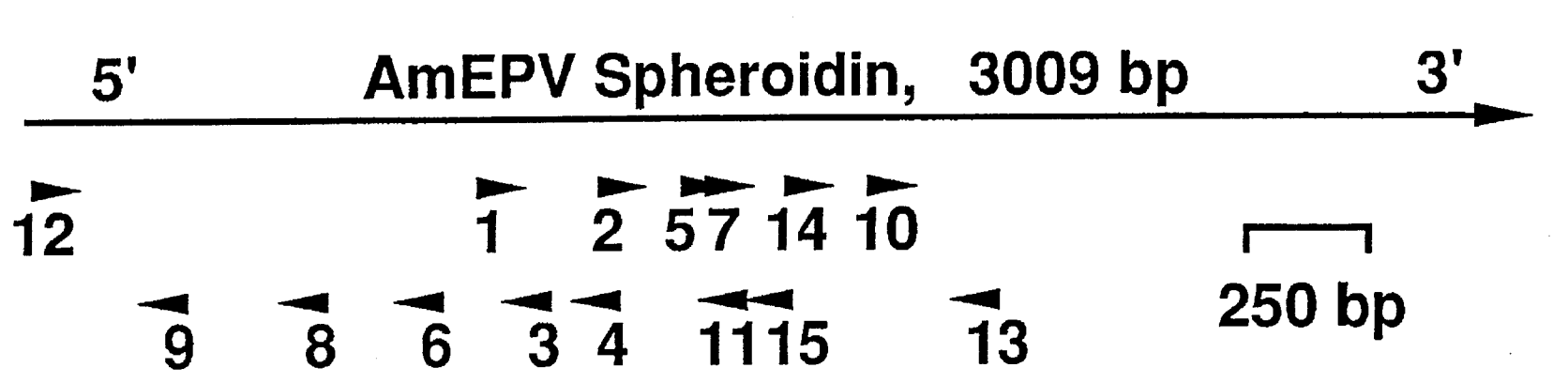

[1]Primer numbers correspond to those in FIG. 5 and the sequences (5' to 3') are shown below:
1. RM58 - GAAGTNGATCCNGAATATGT
2. RM75 - GAAAATAAAATTATATTGGA
3. RM76 - AGACAATTCCAGATATAATG
4. RM78 - CCGCATCTATATTCTGCTTC
5. RM79 - GTTTAAAACCTAAAGTACCC
6. RM82 - TTTCAAATTAACTGGCAACC
7. RM83 - GGGATGGATTTTAGATTGCG
8. RM87 - GTTGCATCTGTAGTTACATC
9. RM91 - TCTAGCAATAATCGACTTAC
10. RM92 - GCCTGGTTGGGTAACAACTC
11. RM93 - CATTTCTATTAAGCCTAACG
12. RM95 - GTACCTTTAGCAACCAAAAC
13. RM118 - CTGCTAGATTATCTACTCCG
14. RM169 - AATTGCACATTATCATTGGG
15. RM170 - ATTACCCAATGATAATGTGC Primer RM206 (AGATGATGATTAAAGTGTGG) (SEQ ID NO. 50) was from bases 2379 through 2398 and RM212 (GATAATGATACTCCGGTTGC) (SEQ ID NO. 51) from bases 2077 through 2096 of the CbEPV NPH I sequence (Yuen et al., 1991).

Cloning and double strand plasmid sequencing. BglII clones in both orientations (1.06 kb and 1.78 kb) covering the unsequenced 5' end of the AmEPV NPH I gene were selected from an AmEPV BglII fragment library (Hall and Moyer, 1991) by hybridization with an AmEPV 13 kb HindIII fragment probe. Plasmids were cloned in the *Escherichia coli* SURE strain (Stratagene, La Jolla, Calif.). Plasmids were sequenced by use of exonuclease III deletions and dideoxy sequencing as described (Hall and Moyer, 1991). Both strands were completely sequenced.

Radiolabeled probes, Southern blotting, and hybridization. Random oligolabeling of DNA for probes, Southern transfer and hybridization (at 65° C. with BLOTTO) were as described previously (Hall and Moyer, 1991).

Protein microsequencing. Lys-c endoprotease digestion of the 115 kDa protein of CbEPV OBs purified and recovered from SDS-PAGE gels was used to generate internal peptide fragments for sequencing on a gas phase sequencer.

Antibody preparation and immunoblotting. A preparation of total occlusion body antigens was prepared by solubilizing purified AmEPV occlusion bodies purified from infected cell cultures. Rabbits were then intradermally injected with 100–200 µg of antigen per rabbit in Freund's complete adjuvant. One month later, the rabbits were boosted with about 500 µg each of the same antigen in incomplete adjuvant. After an additional 3 weeks, the rabbits were boosted with 200 µg of antigen in incomplete adjuvant.

Eleven days later, the immune serum was collected. This serum is referred to as occlusion body antisera. Monospecific spheroidin antibodies were prepared from this serum based on immunoaffinity of individual antibodies for purified spheroidin (Harlow and Lane, 1988). Samples of the sera were adsorbed to a nitrocellulose blot prepared from a preparative SDS-PAGE gel of solubilized AmEPV occlusion bodies. The section of the blot containing the 115 kDa AmEPV spheroidin and bound antibodies was then excised. The monospecific AmEPV spheroidin antibodies were eluted using 100 mM glycine, pH 2.5. After neutralization and dilution, the monospecific spheroidin antibodies were used to probe Western blots.

For immunoblotting, duplicate samples run on SDS-PAGE gels were prepared. One-half of the gel was stained with Coomassie blue, and the other half (containing prestained molecular mass markers) was transferred to nitrocellulose membrane in Tris-glycine buffer (Harlow and Lane, 1988) using the BioRad Trans Blot at 250 mA for 3 hours. The blot was blocked for 2 hr using BLOTTO (0.5% nonfat dry milk in TBS: 0.01M Tris, pH8, 0.15M NaCl). Dilutions of the antibody were prepared in BLOTTO and adsorbed to the blot overnight. The blot was washed 3 times in TBS at room temperature, and the secondary antibody (goat anti-rabbit conjugated to alkaline phosphatase) at a 1:1000 dilution was adsorbed to the blot for 1½hr. The blot was washed with TBS as previously. Secondary antibody reactions and color development was as described (Harlow and Lane, 1988).

SDS-PAGE of solubilized occlusion bodies. When purified occlusion bodies of CbEPV, CfEPV and AmEPV are solubilized in Laemmli sample buffer, boiled immediately, and analyzed on SDS-PAGE gels, Coomassie blue staining shows the major protein to be about 115 kDa in each case. The Choristoneura EPVs show a second 47 kDa protein in lesser amounts. Other minor proteins were also observed.

The purported CbEPV spheroidin gene has a coding capacity of 47 kDa (Yuen et al., 1990) despite the fact that the observed size of the corresponding spheroidin appears to be 115 kDa, which is similar to that observed for the AmEPV spheroidin. This discrepancy has been explained by suggesting that the CbEPV spheroidin exists as relatively unstable dimers, which dissociate under a variety of conditions to monomers of 47 kDa (Yuen et al., 1990). The AmEPV spheroidin of 115 kDa, however, shows no such propensity for dissociation.

Prior to dissolution, occlusion bodies are stable and routinely stored at 4° C. in buffer. The only discernible difference in methods of occlusion body solubilization and preparation is the incubation time in SDS buffer before boiling. The relative instability of the various spheroidins was evaluated by incubating the occlusion bodies of all three EPVs at room temperature for up to two hours in SDS solubilizing buffer before boiling the samples. While some degradation of the 115 kDa protein was observed for the CfEPV OB preparation, little if any degradation of the CbEPV or AmEPV preparations was observed. The CfEPV 115 kDa protein was degraded to a variety of smaller proteins but not in a fashion suggesting a relationship to the 47 kDa protein. Whether the OB suspension was in 1X TE (10 mM Tris, 1 mM EDTA, pH8) or in deionized water prior to dissolution has no effect on the subsequent degradation CfEPV occlusion bodies.

Discovery of an AmEPV spheroidin gene homolog in CbEPV and CfEPV. Selected oligonucleotide primers derived from within various regions of the AmEPV spheroidin gene were selected as appropriate primer pairs for PCR to look for the spheroidin gene in CbEPV and CfEPV. The relative positions of these primers within the spheroidin gene are shown in FIG. 5. Table 2 lists the specific primer pairs and sequences, the expected size of the PCR products based on the AmEPV spheroidin sequences, and the results when these primers were used in conjunction with CbEPV or CfEPV templates. From Table 2, for CbEPV template 10 out 19 primer pairs resulted in an appropriate size product expected if the two genes were similar. For CfEPV this was 13 out of 19 primer pairs. We chose one of the products (1 kb) generated from CfEPV DNA by primer pair 1–13 (in Table 2) for further analyses.

This PCR product was radiolabeled and used as a probe for a blot containing restriction fragments of both CfEPV and AmEPV DNAs. All hybridizations to CfEPV showed predominant, specific hybridization signals. The CfEPV derived probe also shows appropriate, discrete hybridizations to AmEPV DNA; i.e., a 13 kb HindIII fragment, a 20 kb EcoRI fragment, a 4.5 kb BglII fragment, and a 4.5 kb BstBI fragment. This pattern of hybridization to AmEPV is that expected for hybridization to the AmEPV spheroidin gene.

Partial sequence of a spheroidin-like gene in CbEPV or CfEPV. Further indications of the existence for an AmEPV spheroidin gene homolog in the genome Choristoneura EPVs come from PCR product sequencing of the 1 kb Choristoneura PCR products (primer pair 1–13; Table 2). The resulting sequences derived from the CbEPV or CfEPV DNA with a comparison to the AmEPV sequence is shown in FIG. 6A. When the deduced amino acid sequence of this region is compared (FIG. 6B), a very high degree of homology is found between all three viruses.

The spheroidin-like gene in CbEPV and CfEPV is expressed. Samples of the CbEPV ≈115 kDa protein were isolated from SDS-polyacrylamide gels, and treated with lys-c endoprotease to generate peptides for microsequencing. Three of the resulting peptides were analyzed, and the amino acid sequence was compared to the spheroidin of AmEPV. The CbEPV sequences obtained were homologous to three corresponding regions of the AmEPV spheroidin (FIG. 6C). These results demonstrate that the Choristoneura viruses not only contain a spheroidin-like gene, but that gene is expressed to yield a polypeptide within occlusion bodies of similar size and sequence to the previously-identified spheroidin protein of AmEPV.

We have also addressed the question of whether the AmEPV spheroidin homolog in CbEPV and CfEPV is expressed by a Western blot analysis of the proteins of CbEPV and CfEPV using antibody derived against either AmEPV occlusion bodies or monospecific sera against AmEPV spheroidin. Sera directed against purified AmEPV occlusion bodies recognize proteins of ≈115 kDa in both CbEPV and AmEPV. Stronger signals are observed in the AmEPV samples as expected. An AmEPV protein of 38 kDa is also recognized in the samples. Weak binding is also observed to the abundantly expressed protein of the vertebrate cowpox virus which was used as a control. When immunoaffinity purified, monospecific AmEPV spheroidin sera is used, the 115 kDa protein of CbEPV also cross-reacts. Similar results were obtained with CfEPV. These results also support the conclusion that the two Choristoneura viruses and AmEPV encode a very similar major occlusion body protein of 115 kDa which in AmEPV corresponds to the spheroidin gene.

Co-linearity of AmEPV, CbEPV, and CfEPV maps in the spheroidin region. We have shown that the gene adjacent to the 3' terminus of the AmEPV spheroidin gene is NPH I (NTPase I) in polarity opposite to that of the spheroidin gene. A NPH I gene from CbEPV has been sequenced (Yuen et al., 1991).

The sequence of the NPH I (or NTPase I) gene of AmEPV is presented in FIG. 7. The 3' end sequence of this gene is provided in FIG. 1 and the nucleotide numbering system depicted in FIG. 7 results from appending the 5' end of the sequence to the sequence provided in FIG. 1.

When the complete coding sequence and deduced amino acid sequence of the AmEPV NPH I gene was compared to the already published CbEPV NPH I gene (Yuen et al., 1991), the two genes show 89% amino acid and 86% nucleotide identity. Both proteins have a deduced 648 amino acids, with the major difference being that AmEPV has deleted amino acid number 127 and has one extra amino acid at the very end of the sequence. Both genes show the typical poxvirus late gene promoter sequence motif, TAAATG, at the beginning of the open reading frame as well as the A+T rich sequence upstream of the gene. Of the 30 bases preceding the starting ATG, only a single G differentiates the AmEPV and CbEPV. The intergenic region between the spheroidin and NPH I genes begins to diverge immediately following the NPH I open reading frame (ORF) at the downstream 3' end.

Figure 8:
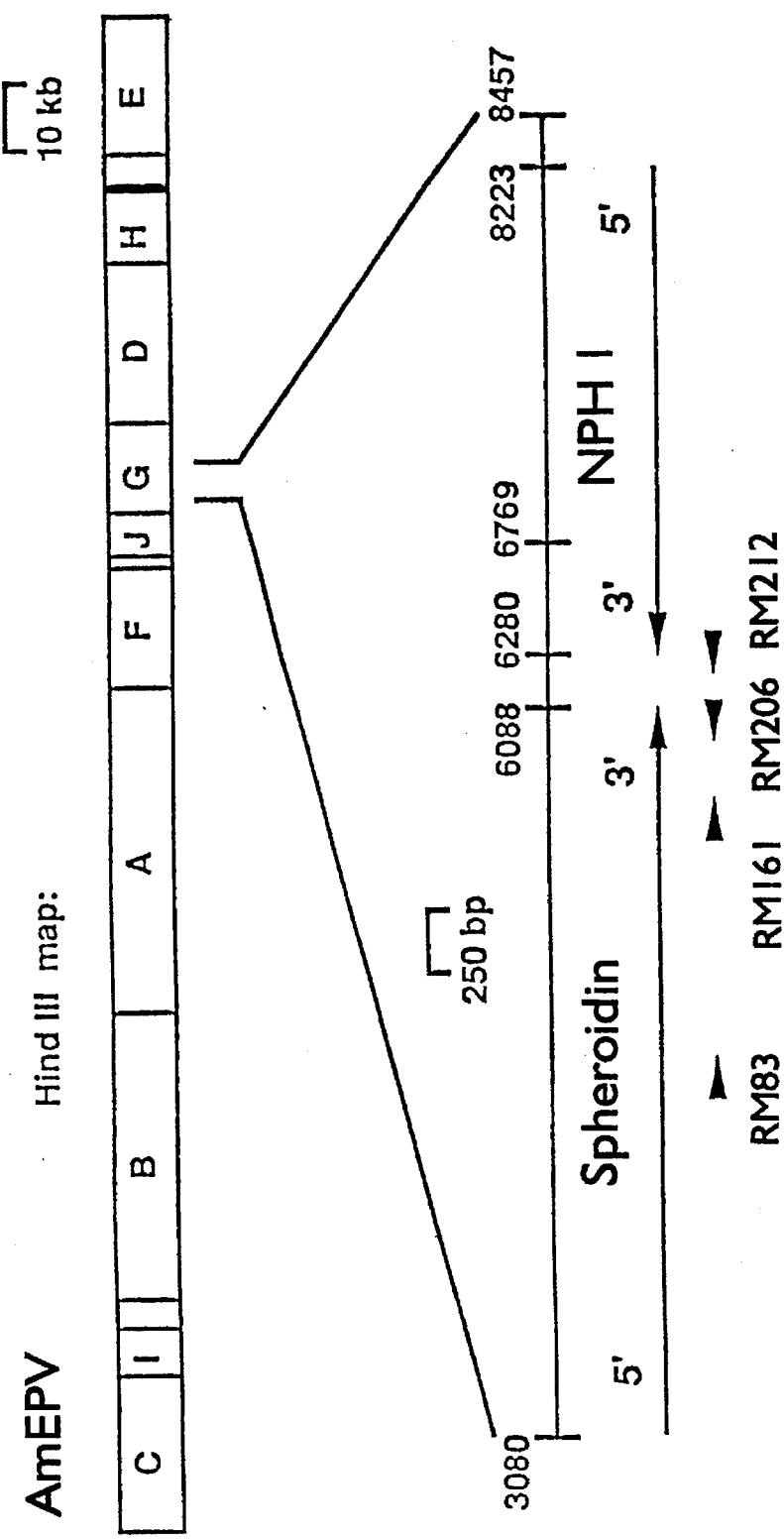
FIG. 8 shows the spheroidin and NPH I gene orientations in AmEPV, and the locations of primers used in PCR reactions. The arrowheads over the numbers in the figure represent oligonucleotide primers. The arrowhead base shows the approximate starting point of the oligo and 5' to 3' is shown by the direction of the arrowhead. RM83 and RM161 are AmEPV spheroidin specific primers. Primer RM212 is from the 3' end of the CbEPV NPH I gene and RM206 is just downstream of the CbEPV NPH I gene but within the published CbEPV sequence (Yuen et al. [1991], supra).

The proximity of the spheroidin and NPH I genes in both Choristoneura viruses was tested by performing a series of PCR reactions using the PCR primers shown in FIG. 8 which were designed based on the AmEPV gene arrangement and were used with either CfEPV or CbEPV. Primers RM206 and RM212 are described above in this example, RM83 and RM161 in Table 2. Primer pair RM161-RM212 failed to give a PCR product with CbEPV DNA indicating sequence differences between CbEPV and CfEPV in the RM161 primer binding region. However, the other three reactions generated PCR products ranging in size from ≈1–2.5 kb, indicating that the NPH I and spheroidin genes are adjacent and arranged similarly to AmEPV. Based on the PCR products, the intergenic distance between the Choristoneura spheroidin and NPH I genes appears to be at least about 450 bp longer than the same region in AmEPV. The increased size of this intergenic region is large enough to perhaps allow for a small ORF to be present between the two genes in the Choristoneura viruses. However, PCR product sequencing of the RM83 - RM212 and the RM161 - RM206 PCR products using RM206 as the primer failed to show any ORF of significant size.

Our results suggest that the published Choristoneura EPV gene identified by Yuen et al. (1990) as the spheroidin gene, is incorrect. Our evidence shows instead that the spheroidin gene of Choristoneura EPVs is virtually identical to that of AmEPV (FIG. 6), i.e., encodes a 115 kDa protein and is expressed. Hence this protein is highly conserved amongst all three viruses.

The AmEPV spheroidin gene found in the Choristoneura EPV genomes and the NPH I genes were found to be immediately adjacent to each other and in opposite polarity in all three viruses. Although the intergenic distance between the two genes is somewhat different between the two Choristoneura viruses and AmEPV, it would appear that the genes in this region of the viral DNA are co-linear.

We have shown that the linear conserved core of genes found in vertebrate poxviruses is not maintained in AmEPV. Based on the data presented here, it appears that the entomopoxviruses have evolved and maintained a common core of co-linear genes, different from their vertebrate counterparts.

It should be understood that the examples and embodiments described herein are for illustrative purposes only. Various modifications or changes in light thereof will be suggested to persons skilled in the art by this specification. The subject invention encompasses recombinant polynucleotide sequences, plasmids, vectors, and transformed hosts which are equivalent to those which are specifically exemplified herein in that the characteristic expression features are retained in said equivalent constructs even if inconsequential modifications to the DNA sequence have been made. For example, it is within the skill of a person trained in the art to use a fragment of the spheroidin gene's non-coding region which is upstream of the structural gene in order to achieve the desired level of expression. Such fragments of the regulatory sequences fall within the scope of the current invention, so long as the desired level of expression which is characteristic of this system is retained. Furthermore, inconsequential changes to the nucleotide sequences can be made without affecting the disclosed functions of these sequences. Such modifications also fall within the scope of the current invention and are to be included within the spirit and purview of this application and the scope of the appended claims.

We claim:

1. A polynucleotide molecule free from association with nucleotide sequences with which it is associated in nature which comprises an Entomopoxvirus spheroidin polynucleotide sequence.

2. The polynucleotide molecule, according to claim 1, wherein said spheroidin polynucleotide sequence is from the *Choristoneura fumiferana* Entomopoxvirus.

3. The polynucleotide molecule, according to claim 1, wherein said spheroidin polynucleotide sequence is from the *Choristoneura biennis* Entomopoxvirus.

4. The polynucleotide molecule, according to claim 1, comprising the spheroidin polynucleotide sequence SEQ ID NO. 1.

5. The polynucleotide molecule, according to claim 1 comprising a polynucleotide sequence selected from the group consisting of a spheroidin gene coding sequence, a spheroidin gene regulatory sequence, and a spheroidin gene promoter sequence.

6. The polynucleotide molecule, according to claim 1, wherein said spheroidin sequence is further characterized by the ability to direct the expression of a heterologous gene to which said sequence is operably linked in a selected host cell or virus.

7. The polynucleotide molecule, according to claim 1, comprising said spheroidin polynucleotide sequence and further comprising a second polynucleotide sequence encoding a heterologous gene.

8. A recombinant molecule comprising a polynucleotide sequence encoding an Entomopoxvirus spheroidin promoter sequence, wherein said sequence is operably linked to a selected heterologous gene sequence, said sequence being capable of directing the expression of said gene in a selected host cell.

9. A recombinant polynucleotide molecule comprising an entomopoxvirus spheroidin promoter sequence operably linked to a heterologous gent, wherein said promoter is capable of directing the expression of said gene in a selected host cell capable of expressing said recombinant polynucleotide molecule wherein said promoter is from an entomopoxvirus selected from the group consisting of *Amsacta moorei* entomopoxvirus, *Choristoneura fumiferana* entomopoxvirus, and *Choristoneura biennis* entomopoxvirus.

10. A recombinant polynucleotide molecule comprising an entomopoxvirus Spheroidin promoter sequence operably linked to a heterologous gene, wherein said promoter is capable of directing the expression of said gene in a selected host cell capable of expressing said recombinant polynucleotide molecule wherein said promoter comprises SEQ. ID NO. 22 which is capable of directing the expression of said heterologous gene.

11. A polynucleotide molecule free from association with nucleotide sequences with which it is associated in nature which comprises an Entomopoxvirus spheroidin polynucleotide sequence; provided that said Entomopoxvirus spheroidin polynucleotide sequence is homologous with an Entomopoxvirus spheroidin sequence which in nature encodes a spheroidin gene product having a molecular weight of greater than 50 kilodaltons.

12. A recombinant molecule comprising a polynucleotide sequence encoding an Entomopoxvirus spheroidin promoter sequence, wherein said sequence is operably linked to a selected heterologous gene sequence, said sequence being capable of directing the expression of said gene in a selected host cell; provided that said spheroidin promoter sequence is one which in nature regulates the expression of a spheroidin gene product having a molecular weight of greater than 50 kilodaltons.

13. A cell infected with a recombinant virus comprising an Entomopoxvirus spheroidin gene polynucleotide sequence operably linked to a selected heterologous gene sequence, provided that said Entomopoxvirus spheroidin gene polynucleotide sequence is one which is homologous to a gene which in nature encodes a spheroidin gene product having a molecular weight of greater than 50 kilodaltons.

14. A polynucleotide molecule free from association with nucleotide sequences with which it is associated in nature which comprises an Entomopoxvirus spheroidin polynucleotide sequence provided that said Entomopoxvirus spheroidin polynucleotide sequence encodes the promoter or coding sequence of an Entomopoxvirus occlusion body protein.

15. A cell infected with a recombinant virus comprising an Entomopoxvirus spheroidin gene polynucleotide sequence operably linked to a selected heterologous gene sequence, provided that said Entomopoxvirus spheroidin gene polynucleotide sequence is one which in nature encodes the major protein of an Entomopoxvirus occlusion body.

16. An isolated polynucleotide molecule comprising a nucleotide sequence selected from the group consisting of SEQ ID NO:1, SEQ ID NO:43, and SEQ ID NO:45.

17. An isolated polynucleotide molecule which encodes a gene product having the amino acid sequence of SEQ ID NO. 6.

\* \* \* \* \*

UNITED STATES PATENT AND TRADEMARK OFFICE
CERTIFICATE OF CORRECTION

PATENT NO. : 5,476,781

DATED : December 19, 1995

INVENTOR(S) : Richard W. Moyer, Richard L. Hall

It is certified that error appears in the above-indentified patent and that said Letters Patent is hereby corrected as shown below:

Column 7: Line 28: "fight" should read --right--.

Column 10: Line 4: "end Of the" should read --end of the--.

Column 13: Line 40: "techniques," should read --techniques.--

Column 14: Line 60: "fights" should read --rights--.

Column 16: Line 18: "beating" should read --bearing--.

Column 18: Line 15: "β-intefferon" should read --β-interferon--.

Columon 19: Line 2: "hybrid. spheroidin-IFN-β gene" should read --hybrid spheroidin-IFN-β gene--.

Column 23: Line 65: "pro" should read --Pro--.

Column 26: Line 18: "(SE0" should read --(SEQ--; Line 63: "(SEQ D" should read --(SEQ ID--.

Column 26: Line 65: "to 465 1" should read --to 4651--.

Column 28: Line 53: "...A)GG  (G/A)CA...TT" should read --...A)GG(G/A)CA...TT--.

UNITED STATES PATENT AND TRADEMARK OFFICE
CERTIFICATE OF CORRECTION

PATENT NO.  : 5,476,781
DATED       : December 19, 1995
INVENTOR(S) : Richard W. Moyer, Richard L. Hall It is certified that error appears in the above-indentified patent and that said Letters Patent is hereby corrected as shown below:

Column 29: Line 16: "(SEO" should read --(SEQ ID--.

Column 29: Line 16: "(SEO" should read --(SEQ ID--; "ORF O3" should read --ORF Q3--.

Column 30: Line 11: "vital" should read --viral--; Line 18: "grog" should read --grown--.

Signed and Sealed this

Tenth Day of September, 1996

Attest:

BRUCE LEHMAN

*Attesting Officer*          *Commissioner of Patents and Trademarks*

SEQUENCE LISTING ( 1 ) GENERAL INFORMATION:

( i i i ) NUMBER OF SEQUENCES: 66

( 2 ) INFORMATION FOR SEQ ID NO:1:

( i ) SEQUENCE CHARACTERISTICS:
        ( A ) LENGTH: 8457 base pairs
        ( B ) TYPE: nucleic acid
        ( C ) STRANDEDNESS: double
        ( D ) TOPOLOGY: unknown ( i i ) MOLECULE TYPE: DNA (genomic)

( v i ) ORIGINAL SOURCE:
        ( A ) ORGANISM: Amsacta moorei entomopoxvirus ( i x ) FEATURE:
        ( A ) NAME/KEY: CDS
        ( B ) LOCATION: complement (65..1459)

( i x ) FEATURE:
        ( A ) NAME/KEY: CDS
        ( B ) LOCATION: 1474..2151

( i x ) FEATURE:
        ( A ) NAME/KEY: CDS
        ( B ) LOCATION: complement (2239..2475)

( i x ) FEATURE:
        ( A ) NAME/KEY: CDS
        ( B ) LOCATION: 2502..2987

( i x ) FEATURE:
        ( A ) NAME/KEY: CDS
        ( B ) LOCATION: 3080..6091

( i x ) FEATURE:
        ( A ) NAME/KEY: CDS
        ( B ) LOCATION: complement (6277..6768)

( x i ) SEQUENCE DESCRIPTION: SEQ ID NO:1:

```
AGATCTGATG  TTCTATATAT  AGTACAAATT  TGTATGATTA  ATTGATATTT  TAAAATTCAA        60

GATATTAAAT  ATTAGATTCT  AAACTATTCT  TCTCATTATC  AATATAACTA  TCATAATCAT       120

TTTTTATTTT  ACTACATACA  TTCATAATTC  TATTACTATT  TTTTTATAC   ATATCTATTA       180

ATTCCATAAA  CTTTTTATTT  TTTATATTAA  ATATTTCTAA  TGTATTTTA   AATTCGTCAA       240
```

```
TACTATTAAT ATCATATCTA GAAATAAATA ATGCACCTCT ATAACTACTA GCCAATAAAT    300

CACCAATAAA ACTCATAGAA TAATATAATT TTTTAAATTC AAATTTAGAT TTTATGTTGA    360

AATAAACTAT ATAATATAAA AATATTATAT TAAACATACC ACAATCGGGA CTATCATATT    420

GTAATTCAAA AGTATTAAAA AAGTAATAAT TTACATTTTT AAATATATCA TTTAAATATT    480

CTGATAGTAC ATCAATGTAT AAATAAGCAT AATTAGTATT AGGAGTACTA TTGTAGTGTT    540

TATGGCTTTT TATAGTCATA TCAGATTCAA TAAACATATA TTTTTATTT TGTTTTATAA     600

GTTCTGGTAT ATAACCACTA CTATTAAAAA AGTATGCAGC TTTTTTATCT TTATCAAAGT    660

GTTTATCTAT TACGCAACAA GTAAATGAT CATTATAAAT TATAGGAAAC ATAAAAAATC     720

TTTTTTTATC ATTCATTAAA AAAAATTTTA CTCTATCTTC AAGTTTATAG CATCTCATAG    780

ATGAAGCTAC TGTAGCAATA TTTTTATCAG TTTTTTCAAA TAAAATCAAA TGAAAATAAT    840

CATAATCTGT ATTAATCATA GTTAATGGAT ATATACAATT ATATATATCT CCCGAACTTA    900

ACCATGTAGA TTTATCATGT TTTCTTGGGT AAGCTTTAGG TTTAGGATTA AATCCCAAAG    960

GCGGTATTCC TATTTGAGCA TCCAAATCAT CATAAATTGT GGCAAATGTA GAAAAATCTC   1020

TTGTTTTGGA TAATTCTGAT TTTAGAAAAG ACTTTCTCAT ATATACTAAT GGAATGCCTT   1080

TATATTTTTT AGATGTAATA AAAGTATTAA TATTTATATT TTTATCTTGT AAATATTTTT   1140

TTATAGTCCA AAATAGAAAA AATTTTCTTT TAATATTATT TTCAAAATTA ATATTATTAA   1200

TATGATTTGG ATCTAAAACT AATTCATTAT ATAATATTTC CAAGTATTTT ATAGGTATAA   1260

ATGTTACTTT ACCTCTTGTT TCATCATCAT CATCTATTTT TTCTAATATA GCTATATTTG   1320

CATTAGTATT ATATTTAATA GGATTTATAA AATATACCAT ATTATCTATT TTACTAAAAA   1380

ATAACATAGA CATAAAATTA ATACCAGATT CTGGCATTTT TAAATTTTTA TTTGGAAATC   1440

TTCTAATTTT ATTATTCATT ATTTATTTAA TAA ATG TTT CTA GTT TAT TTC AAT   1494
                                   Met Phe Leu Val Tyr Phe Asn
                                    1                   5

ACA TTT TTA ATA ATA ATT TTA TTA TTT GGT ATT ATA GGT ATT TAT ATA    1542
Thr Phe Leu Ile Ile Ile Leu Leu Phe Gly Ile Ile Gly Ile Tyr Ile
         10                  15                  20

TTA ACA TTT GTG TTT AAT ATA GAT TTT TTA ATA AAT AAT AAT AAA ATA    1590
Leu Thr Phe Val Phe Asn Ile Asp Phe Leu Ile Asn Asn Asn Lys Ile
     25                  30                  35

TAT ATA TTA TCA TAT AAC GCA ACT AAT ATA AAC AAT ATA AAT AAT TTA    1638
Tyr Ile Leu Ser Tyr Asn Ala Thr Asn Ile Asn Asn Ile Asn Asn Leu
 40                  45                  50                  55

AAT TTA TAC GAT TAT TCA GAT ATT ATA TTT TTG ACA AAT TTT AAC ATA    1686
Asn Leu Tyr Asp Tyr Ser Asp Ile Ile Phe Leu Thr Asn Phe Asn Ile
                 60                  65                  70

AAT AAT AAT CTT TTA GTA ACA CAA GCT AAT AAT TTA CAA GAT ATA CCA    1734
Asn Asn Asn Leu Leu Val Thr Gln Ala Asn Asn Leu Gln Asp Ile Pro
             75                  80                  85

ATA TTT AAT GTA AAT AAT ATT ATA TCT AAT CAA TAT AAT TTT TAT TCA    1782
Ile Phe Asn Val Asn Asn Ile Ile Ser Asn Gln Tyr Asn Phe Tyr Ser
         90                  95                 100

GCG TCT AGT AAT AAT GTA AAT ATA TTA TTA GGA TTA AGA AAA ACA TTA    1830
Ala Ser Ser Asn Asn Val Asn Ile Leu Leu Gly Leu Arg Lys Thr Leu
     105                 110                 115

AAT ATA AAT AGA AAT CCA TTT TTA TTA TTT AGA AAT ACA TCT CTA GCT    1878
Asn Ile Asn Arg Asn Pro Phe Leu Leu Phe Arg Asn Thr Ser Leu Ala
120                 125                 130                 135

ATA GTT TTC AAT AAT AAT GAA ACT TTT CAC TGT TAT ATA AGT TCA AAT    1926
Ile Val Phe Asn Asn Asn Glu Thr Phe His Cys Tyr Ile Ser Ser Asn
```

|  |  |  |  |  |  |  |  |  |  |  |  |  |  |  |  |  |
|---|---|---|---|---|---|---|---|---|---|---|---|---|---|---|---|---|
|  |  |  |  | 140 |  |  |  | 145 |  |  |  | 150 |  |  |  |  |
| CAA | AAT | AGT | GAT | GTA | TTA | GAT | ATA | GTA | TCA | CAT | ATA | GAA | TTT | ATG | AAA | 1974 |
| Gln | Asn | Ser | Asp<br>155 | Val | Leu | Asp | Ile | Val<br>160 | Ser | His | Ile | Glu | Phe<br>165 | Met | Lys |  |
| TCT | AGA | TAT | AAT | AAA | TAT | GTA | ATT | ATA | GGA | GAA | ATA | CCC | GTA | AAT | AAT | 2022 |
| Ser | Arg | Tyr<br>170 | Asn | Lys | Tyr | Val | Ile<br>175 | Ile | Gly | Glu | Ile | Pro<br>180 | Val | Asn | Asn |  |
| AAT | ATA | TCT | ATT | AAT | AAT | ATA | TTA | AAT | AAT | TTT | GCT | ATT | ATA | ACT | AAT | 2070 |
| Asn | Ile<br>185 | Ser | Ile | Asn | Asn | Ile<br>190 | Leu | Asn | Asn | Phe | Ala<br>195 | Ile | Ile | Thr | Asn |  |
| GTG | AGA | TTA | ATA | GAT | AAA | TAT | AAC | TCT | ATA | ATA | TCA | TTT | TTA | AAT | ATC | 2118 |
| Val<br>200 | Arg | Leu | Ile | Asp | Lys<br>205 | Tyr | Asn | Ser | Ile | Ile<br>210 | Ser | Phe | Leu | Asn | Ile<br>215 |  |
| AAC | GTA | GGA | ACA | CTT | TTT | GTC | ATA | AAT | CCA | TAATATTTAG | TAATAATCAC |  |  |  |  | 2168 |
| Asn | Val | Gly | Thr | Leu<br>220 | Phe | Val | Ile | Asn | Pro<br>225 |  |  |  |  |  |  |  |

| TAACATATTT | TTTATTAAAA | TGAATAAAAT | ATATATTGTT | ATTGTCAATA | TTTTATATCA | 2228 |
|---|---|---|---|---|---|---|
| TTTTACAGTC | TTATTTTTTT | TTTTGCTTT | TAGGTATAAT | TTTACCTTCT | AAACGTTTAT | 2288 |
| CTCCCCAAAC | ATCTACAGTA | GATGGTTTAT | TAGATTCTGT | GTTATACACA | TCTGCTGGAT | 2348 |
| TTGCGGCATT | TGTATCCAAA | CCATAATATC | CAGGTCTATA | ATTATCTTTA | AAAACTTGGG | 2408 |
| ATTGAGATAC | TTCTTCAGTT | TTTAAATTAT | TAAAATATCC | AAGATTATTT | TTTTTGATG | 2468 |

|  |  |  |  |  |  |  |  |  |  |  |  |  |  |  |  |  |
|---|---|---|---|---|---|---|---|---|---|---|---|---|---|---|---|---|
| AAGACATAAT | TGATATTATA | ATACTTTATA | GAT | ATG | TCA | ATA | TTT | ATC | TAC | TAT |  |  |  |  |  | 2522 |
|  |  |  |  | Met<br>1 | Ser | Ile | Phe | Ile<br>5 | Tyr | Tyr |  |  |  |  |  |  |
| ATT | TTC | AAC | AAT | AGA | TTT | TAT | ATA | TAT | AAA | AGA | ATG | AAT | ACT | GTA | CAA | 2570 |
| Ile | Phe | Asn<br>10 | Asn | Arg | Phe | Tyr | Ile<br>15 | Tyr | Lys | Arg | Met | Asn<br>20 | Thr | Val | Gln |  |
| ATT | TTA | GTT | GTC | ATA | TTA | ATA | ACA | ACA | GCA | TTA | TCT | TTT | CTA | GTT | TTT | 2618 |
| Ile | Leu<br>25 | Val | Val | Ile | Leu | Ile<br>30 | Thr | Thr | Ala | Leu | Ser<br>35 | Phe | Leu | Val | Phe |  |
| CAA | TTA | TGG | TAT | TAT | GCC | GAA | AAT | TAC | GAA | TAT | ATA | TTA | AGA | TAT | AAT | 2666 |
| Gln<br>40 | Leu | Trp | Tyr | Tyr | Ala<br>45 | Glu | Asn | Tyr | Glu | Tyr<br>50 | Ile | Leu | Arg | Tyr | Asn<br>55 |  |
| GAT | ACA | TAT | TCA | AAT | TTA | CAA | TTT | GCG | AGA | AGC | GCA | AAT | ATA | AAT | TTT | 2714 |
| Asp | Thr | Tyr | Ser | Asn<br>60 | Leu | Gln | Phe | Ala | Arg<br>65 | Ser | Ala | Asn | Ile | Asn<br>70 | Phe |  |
| GAT | GAT | TTA | ACT | GTT | TTT | GAT | CCC | AAC | GAT | AAT | GTT | TTT | AAT | GTT | GAA | 2762 |
| Asp | Asp | Leu | Thr<br>75 | Val | Phe | Asp | Pro | Asn<br>80 | Asp | Asn | Val | Phe | Asn<br>85 | Val | Glu |  |
| GAA | AAA | TGG | CGC | TGT | GCT | TCA | ACT | AAT | AAT | AAT | ATA | TTT | TAT | GCA | GTT | 2810 |
| Glu | Lys | Trp<br>90 | Arg | Cys | Ala | Ser | Thr<br>95 | Asn | Asn | Asn | Ile | Phe<br>100 | Tyr | Ala | Val |  |
| TCA | ACT | TTT | GGA | TTT | TTA | AGT | ACA | GAA | AGT | ACT | GGT | ATT | AAT | TTA | ACA | 2858 |
| Ser | Thr | Phe<br>105 | Gly | Phe | Leu | Ser | Thr<br>110 | Glu | Ser | Thr | Gly | Ile<br>115 | Asn | Leu | Thr |  |
| TAT | ACA | AAT | TCT | AGA | GAT | TGT | ATT | ATA | GAT | TTA | TTT | TCT | AGA | ATT | ATA | 2906 |
| Tyr | Thr<br>120 | Asn | Ser | Arg | Asp | Cys<br>125 | Ile | Ile | Asp | Leu | Phe<br>130 | Ser | Arg | Ile | Ile<br>135 |  |
| AAA | ATA | GTA | TAT | GAT | CCT | TGT | ACT | GTC | GAA | ACA | TCT | AAC | GAT | TGT | AGA | 2954 |
| Lys | Ile | Val | Tyr | Asp<br>140 | Pro | Cys | Thr | Val | Glu<br>145 | Thr | Ser | Asn | Asp | Cys<br>150 | Arg |  |
| TTA | TTA | AGA | TTA | TTG | ATG | GCC | AAT | ACA | TCA | TAAATACATT | ATAATATTAT |  |  |  |  | 3004 |
| Leu | Leu | Arg | Leu<br>155 | Leu | Met | Ala | Asn | Thr<br>160 | Ser |  |  |  |  |  |  |  |

| TATAATATCA | ATCATAATTT | TTATATATAT | TTTATCTAAA | AGGACTTTTT | ATTTTTTATA | 3064 |
|---|---|---|---|---|---|---|
| TATTAATAAT | AATAA | ATG AGT AAC GTA CCT TTA GCA ACC AAA ACA ATA AGA |  |  |  | 3115 |

|              |              |              |              |     Met Ser Asn Val Pro Leu Ala Thr Lys Thr Ile Arg |
|              |              |              |              |     1                   5                  10       |

| AAA | TTA | TCA | AAT | CGA | AAA | TAT | GAA | ATA | AAG | ATT | TAT | TTA | AAA | GAT | GAA | 3163 |
| Lys | Leu | Ser | Asn | Arg | Lys | Tyr | Glu | Ile | Lys | Ile | Tyr | Leu | Lys | Asp | Glu |      |
|     |     | 15  |     |     |     | 20  |     |     |     |     | 25  |     |     |     |     |      |

| AAT | ACT | TGT | TTC | GAA | CGT | GTA | GTA | GAT | ATG | GTA | GTT | CCA | TTA | TAT | GAT | 3211 |
| Asn | Thr | Cys | Phe | Glu | Arg | Val | Val | Asp | Met | Val | Val | Pro | Leu | Tyr | Asp |      |
|     | 30  |     |     |     | 35  |     |     |     |     | 40  |     |     |     |     |     |      |

| GTG | TGT | AAT | GAA | ACT | TCT | GGT | GTT | ACT | TTA | GAA | TCA | TGT | AGT | CCA | AAT | 3259 |
| Val | Cys | Asn | Glu | Thr | Ser | Gly | Val | Thr | Leu | Glu | Ser | Cys | Ser | Pro | Asn |      |
| 45  |     |     |     |     | 50  |     |     |     |     | 55  |     |     |     |     | 60  |      |

| ATA | GAA | GTA | ATT | GAA | TTA | GAC | AAT | ACT | CAT | GTT | AGA | ATC | AAA | GTT | CAC | 3307 |
| Ile | Glu | Val | Ile | Glu | Leu | Asp | Asn | Thr | His | Val | Arg | Ile | Lys | Val | His |      |
|     |     |     |     | 65  |     |     |     |     | 70  |     |     |     |     | 75  |     |      |

| GGC | GAT | ACA | TTA | AAA | GAA | ATG | TGT | TTT | GAA | TTA | TTG | TTC | CCG | TGT | AAT | 3355 |
| Gly | Asp | Thr | Leu | Lys | Glu | Met | Cys | Phe | Glu | Leu | Leu | Phe | Pro | Cys | Asn |      |
|     |     |     | 80  |     |     |     |     | 85  |     |     |     |     | 90  |     |     |      |

| GTA | AAC | GAA | GCC | CAA | GTA | TGG | AAA | TAT | GTA | AGT | CGA | TTA | TTG | CTA | GAT | 3403 |
| Val | Asn | Glu | Ala | Gln | Val | Trp | Lys | Tyr | Val | Ser | Arg | Leu | Leu | Leu | Asp |      |
|     | 95  |     |     |     |     | 100 |     |     |     |     | 105 |     |     |     |     |      |

| AAT | GTA | TCA | CAT | AAT | GAC | GTA | AAA | TAT | AAA | TTA | GCT | AAT | TTT | AGA | CTG | 3451 |
| Asn | Val | Ser | His | Asn | Asp | Val | Lys | Tyr | Lys | Leu | Ala | Asn | Phe | Arg | Leu |      |
|     | 110 |     |     |     |     | 115 |     |     |     |     | 120 |     |     |     |     |      |

| ACT | CTT | AAT | GGA | AAA | CAT | TTA | AAA | TTA | AAA | GAA | ATC | GAT | CAA | CCG | CTA | 3499 |
| Thr | Leu | Asn | Gly | Lys | His | Leu | Lys | Leu | Lys | Glu | Ile | Asp | Gln | Pro | Leu |      |
| 125 |     |     |     |     | 130 |     |     |     |     | 135 |     |     |     |     | 140 |      |

| TTT | ATT | TAT | TTT | GTC | GAT | GAT | TTG | GGA | AAT | TAT | GGA | TTA | ATT | ACT | AAG | 3547 |
| Phe | Ile | Tyr | Phe | Val | Asp | Asp | Leu | Gly | Asn | Tyr | Gly | Leu | Ile | Thr | Lys |      |
|     |     |     |     | 145 |     |     |     |     | 150 |     |     |     |     | 155 |     |      |

| GAA | AAT | ATT | CAA | AAT | AAT | AAT | TTA | CAA | GTT | AAC | AAA | GAT | GCA | TCA | TTT | 3595 |
| Glu | Asn | Ile | Gln | Asn | Asn | Asn | Leu | Gln | Val | Asn | Lys | Asp | Ala | Ser | Phe |      |
|     |     |     | 160 |     |     |     |     | 165 |     |     |     |     | 170 |     |     |      |

| ATT | ACT | ATA | TTT | CCA | CAA | TAT | GCG | TAT | ATT | TGT | TTA | GGT | AGA | AAA | GTA | 3643 |
| Ile | Thr | Ile | Phe | Pro | Gln | Tyr | Ala | Tyr | Ile | Cys | Leu | Gly | Arg | Lys | Val |      |
|     |     | 175 |     |     |     |     | 180 |     |     |     |     | 185 |     |     |     |      |

| TAT | TTA | AAT | GAA | AAA | GTA | ACT | TTT | GAT | GTA | ACT | ACA | GAT | GCA | ACT | AAT | 3691 |
| Tyr | Leu | Asn | Glu | Lys | Val | Thr | Phe | Asp | Val | Thr | Thr | Asp | Ala | Thr | Asn |      |
|     | 190 |     |     |     |     | 195 |     |     |     |     | 200 |     |     |     |     |      |

| ATT | ACT | TTA | GAT | TTT | AAT | AAA | TCT | GTT | AAT | ATC | GCA | GTA | TCA | TTC | CTT | 3739 |
| Ile | Thr | Leu | Asp | Phe | Asn | Lys | Ser | Val | Asn | Ile | Ala | Val | Ser | Phe | Leu |      |
| 205 |     |     |     |     | 210 |     |     |     |     | 215 |     |     |     |     | 220 |      |

| GAT | ATA | TAT | TAC | GAA | GTT | AAT | AAT | AAT | GAA | CAA | AAA | GAT | TTA | TTA | AAA | 3787 |
| Asp | Ile | Tyr | Tyr | Glu | Val | Asn | Asn | Asn | Glu | Gln | Lys | Asp | Leu | Leu | Lys |      |
|     |     |     |     | 225 |     |     |     |     | 230 |     |     |     |     | 235 |     |      |

| GAT | TTA | CTT | AAG | AGA | TAC | GGT | GAA | TTT | GAA | GTC | TAT | AAC | GCA | GAT | ACT | 3835 |
| Asp | Leu | Leu | Lys | Arg | Tyr | Gly | Glu | Phe | Glu | Val | Tyr | Asn | Ala | Asp | Thr |      |
|     |     |     | 240 |     |     |     |     | 245 |     |     |     |     | 250 |     |     |      |

| GGA | TTA | ATT | TAT | GCT | AAA | AAT | CTA | AGT | ATT | AAA | AAT | TAT | GAT | ACT | GTG | 3883 |
| Gly | Leu | Ile | Tyr | Ala | Lys | Asn | Leu | Ser | Ile | Lys | Asn | Tyr | Asp | Thr | Val |      |
|     |     | 255 |     |     |     |     | 260 |     |     |     |     | 265 |     |     |     |      |

| ATT | CAA | GTA | GAA | AGG | TTG | CCA | GTT | AAT | TTG | AAA | GTT | AGA | GCA | TAT | ACT | 3931 |
| Ile | Gln | Val | Glu | Arg | Leu | Pro | Val | Asn | Leu | Lys | Val | Arg | Ala | Tyr | Thr |      |
|     | 270 |     |     |     |     | 275 |     |     |     |     | 280 |     |     |     |     |      |

| AAG | GAT | GAA | AAT | GGT | CGC | AAT | CTA | TGT | TTG | ATG | AAA | ATA | ACA | TCT | AGT | 3979 |
| Lys | Asp | Glu | Asn | Gly | Arg | Asn | Leu | Cys | Leu | Met | Lys | Ile | Thr | Ser | Ser |      |
| 285 |     |     |     |     | 290 |     |     |     |     | 295 |     |     |     |     | 300 |      |

| ACA | GAA | GTA | GAC | CCC | GAG | TAT | GTA | ACT | AGT | AAT | AAT | GCT | TTA | TTG | GGT | 4027 |
| Thr | Glu | Val | Asp | Pro | Glu | Tyr | Val | Thr | Ser | Asn | Asn | Ala | Leu | Leu | Gly |      |
|     |     |     |     | 305 |     |     |     |     | 310 |     |     |     |     | 315 |     |      |

```
ACG CTC AGA GTA TAT AAA AAG TTT GAT AAA TCT CAT TTA AAA ATT GTA    4075
Thr Leu Arg Val Tyr Lys Lys Phe Asp Lys Ser His Leu Lys Ile Val
            320                 325             330

ATG CAT AAC AGA GGA AGT GGT AAT GTA TTT CCA TTA AGA TCA TTA TAT    4123
Met His Asn Arg Gly Ser Gly Asn Val Phe Pro Leu Arg Ser Leu Tyr
        335                 340             345

CTG GAA TTG TCT AAT GTA AAA GGA TAT CCA GTT AAA GCA TCT GAT ACT    4171
Leu Glu Leu Ser Asn Val Lys Gly Tyr Pro Val Lys Ala Ser Asp Thr
    350                 355             360

TCG AGA TTA GAT GTT GGT ATT TAC AAA TTA AAT AAA ATT TAT GTA GAT    4219
Ser Arg Leu Asp Val Gly Ile Tyr Lys Leu Asn Lys Ile Tyr Val Asp
365                 370             375                 380

AAC GAC GAA AAT AAA ATT ATA TTG GAA GAA ATT GAA GCA GAA TAT AGA    4267
Asn Asp Glu Asn Lys Ile Ile Leu Glu Glu Ile Glu Ala Glu Tyr Arg
                385             390             395

TGC GGA AGA CAA GTA TTC CAC GAA CGT GTA AAA CTT AAT AAA CAC CAA    4315
Cys Gly Arg Gln Val Phe His Glu Arg Val Lys Leu Asn Lys His Gln
            400             405             410

TGT AAA TAT ACT CCC AAA TGT CCA TTC CAA TTT GTT GTA AAC AGC CCA    4363
Cys Lys Tyr Thr Pro Lys Cys Pro Phe Gln Phe Val Val Asn Ser Pro
        415             420             425

GAT ACT ACG ATT CAC TTA TAT GGT ATT TCT AAT GTT TGT TTA AAA CCT    4411
Asp Thr Thr Ile His Leu Tyr Gly Ile Ser Asn Val Cys Leu Lys Pro
    430             435             440

AAA GTA CCC AAA AAT TTA AGA CTT TGG GGA TGG ATT TTA GAT TGC GAT    4459
Lys Val Pro Lys Asn Leu Arg Leu Trp Gly Trp Ile Leu Asp Cys Asp
445             450             455                 460

ACT TCT AGA TTT ATT AAA CAT ATG GCT GAT GGA TCT GAT GAT TTA GAT    4507
Thr Ser Arg Phe Ile Lys His Met Ala Asp Gly Ser Asp Asp Leu Asp
                465             470             475

CTT GAC GTT AGG CTT AAT AGA AAT GAT ATA TGT TTA AAA CAA GCC ATA    4555
Leu Asp Val Arg Leu Asn Arg Asn Asp Ile Cys Leu Lys Gln Ala Ile
            480             485             490

AAA CAA CAT TAT ACT AAT GTA ATT ATA TTA GAG TAC GCA AAT ACA TAT    4603
Lys Gln His Tyr Thr Asn Val Ile Ile Leu Glu Tyr Ala Asn Thr Tyr
        495             500             505

CCA AAT TGC ACA TTA TCA TTG GGT AAT AAT AGA TTT AAT AAT GTA TTT    4651
Pro Asn Cys Thr Leu Ser Leu Gly Asn Asn Arg Phe Asn Asn Val Phe
    510             515             520

GAT ATG AAT GAT AAC AAA ACT ATA TCT GAG TAT ACT AAC TTT ACA AAA    4699
Asp Met Asn Asp Asn Lys Thr Ile Ser Glu Tyr Thr Asn Phe Thr Lys
525             530             535                 540

AGT AGA CAA GAC CTT AAT AAC ATG TCA TGT ATA TTA GGA ATA AAC ATA    4747
Ser Arg Gln Asp Leu Asn Asn Met Ser Cys Ile Leu Gly Ile Asn Ile
                545             550             555

GGT AAT TCC GTA AAT ATT AGT AGT TTG CCT GGT TGG GTA ACA CCT CAC    4795
Gly Asn Ser Val Asn Ile Ser Ser Leu Pro Gly Trp Val Thr Pro His
            560             565             570

GAA GCT AAA ATT CTA AGA TCT GGT TGT GCT AGA GTT AGA GAA TTT TGT    4843
Glu Ala Lys Ile Leu Arg Ser Gly Cys Ala Arg Val Arg Glu Phe Cys
        575             580             585

AAA TCA TTC TGT GAT CTT TCT AAT AAG AGA TTC TAT GCT ATG GCT AGA    4891
Lys Ser Phe Cys Asp Leu Ser Asn Lys Arg Phe Tyr Ala Met Ala Arg
    590             595             600

GAT CTC GTA AGT TTA CTA TTT ATG TGT AAC TAT GTT AAT ATT GAA ATT    4939
Asp Leu Val Ser Leu Leu Phe Met Cys Asn Tyr Val Asn Ile Glu Ile
605             610             615                 620

AAC GAA GCA GTA TGC GAA TAT CCT GGA TAT GTC ATA TTA TTC GCA AGA    4987
Asn Glu Ala Val Cys Glu Tyr Pro Gly Tyr Val Ile Leu Phe Ala Arg
                625             630             635
```

```
GCT ATT AAA GTA ATT AAT GAT TTA TTA TTA ATT AAC GGA GTA GAT AAT        5035
Ala Ile Lys Val Ile Asn Asp Leu Leu Leu Ile Asn Gly Val Asp Asn
        640             645                 650

CTA GCA GGA TAT TCA ATT TCC TTA CCT ATA CAT TAT GGA TCT ACT GAA        5083
Leu Ala Gly Tyr Ser Ile Ser Leu Pro Ile His Tyr Gly Ser Thr Glu
        655             660                 665

AAG ACT CTA CCA AAT GAA AAG TAT GGT GGT GTT GAT AAG AAA TTT AAA        5131
Lys Thr Leu Pro Asn Glu Lys Tyr Gly Gly Val Asp Lys Lys Phe Lys
        670             675                 680

TAT CTA TTC TTA AAG AAT AAA CTA AAA GAT TTA ATG CGT GAT GCT GAT        5179
Tyr Leu Phe Leu Lys Asn Lys Leu Lys Asp Leu Met Arg Asp Ala Asp
685             690                 695                 700

TTT GTC CAA CCT CCA TTA TAT ATT TCT ACT TAC TTT AGA ACT TTA TTG        5227
Phe Val Gln Pro Pro Leu Tyr Ile Ser Thr Tyr Phe Arg Thr Leu Leu
                705                 710                 715

GAT GCT CCA CCA ACT GAT AAT TAT GAA AAA TAT TTG GTT GAT TCG TCC        5275
Asp Ala Pro Pro Thr Asp Asn Tyr Glu Lys Tyr Leu Val Asp Ser Ser
            720                 725                 730

GTA CAA TCA CAA GAT GTT CTA CAG GGT CTG TTG AAT ACA TGT AAT ACT        5323
Val Gln Ser Gln Asp Val Leu Gln Gly Leu Leu Asn Thr Cys Asn Thr
        735                 740                 745

ATT GAT ACT AAT GCT AGA GTT GCA TCA AGT GTT ATT GGA TAT GTT TAT        5371
Ile Asp Thr Asn Ala Arg Val Ala Ser Ser Val Ile Gly Tyr Val Tyr
750                 755                 760

GAA CCA TGC GGA ACA TCA GAA CAT AAA ATT GGT TCA GAA GCA TTG TGT        5419
Glu Pro Cys Gly Thr Ser Glu His Lys Ile Gly Ser Glu Ala Leu Cys
765                 770                 775                 780

AAA ATG GCT AAA GAA GCA TCT AGA TTA GGA AAT CTA GGT TTA GTA AAT        5467
Lys Met Ala Lys Glu Ala Ser Arg Leu Gly Asn Leu Gly Leu Val Asn
                785                 790                 795

CGT ATT AAT GAA AGT AAT TAC AAC AAA TGT AAT AAA TAT GGT TAT AGA        5515
Arg Ile Asn Glu Ser Asn Tyr Asn Lys Cys Asn Lys Tyr Gly Tyr Arg
            800                 805                 810

GGA GTA TAC GAA AAT AAC AAA CTA AAA ACA AAA TAT TAT AGA GAA ATA        5563
Gly Val Tyr Glu Asn Asn Lys Leu Lys Thr Lys Tyr Tyr Arg Glu Ile
        815                 820                 825

TTT GAT TGT AAT CCT AAT AAT AAT AAT GAA TTA ATA TCC AGA TAT GGA        5611
Phe Asp Cys Asn Pro Asn Asn Asn Asn Glu Leu Ile Ser Arg Tyr Gly
830                 835                 840

TAT AGA ATA ATG GAT TTA CAT AAA ATT GGA GAA ATT TTT GCA AAT TAC        5659
Tyr Arg Ile Met Asp Leu His Lys Ile Gly Glu Ile Phe Ala Asn Tyr
845                 850                 855                 860

GAT GAA AGT GAA TCT CCT TGC GAA CGA AGA TGT CAT TAC TTG GAA GAT        5707
Asp Glu Ser Glu Ser Pro Cys Glu Arg Arg Cys His Tyr Leu Glu Asp
                865                 870                 875

AGA GGT CTT TTA TAT GGT CCT GAA TAT GTA CAT CAC AGA TAT CAA GAA        5755
Arg Gly Leu Leu Tyr Gly Pro Glu Tyr Val His His Arg Tyr Gln Glu
            880                 885                 890

TCA TGT ACG CCT AAT ACG TTT GGA AAT AAC ACA AAT TGT GTA ACA AGA        5803
Ser Cys Thr Pro Asn Thr Phe Gly Asn Asn Thr Asn Cys Val Thr Arg
        895                 900                 905

AAT GGT GAA CAA CAC GTA TAC GAA AAT AGT TGT GGA GAT AAT GCA ACA        5851
Asn Gly Glu Gln His Val Tyr Glu Asn Ser Cys Gly Asp Asn Ala Thr
910                 915                 920

TGT GGA AGA AGA ACA GGA TAT GGA AGA AGA AGT AGG GAT GAA TGG AAT        5899
Cys Gly Arg Arg Thr Gly Tyr Gly Arg Arg Ser Arg Asp Glu Trp Asn
925                 930                 935                 940

GAC TAT AGA AAA CCC CAC GTT TAT GAC AAT TGT GCC GAT GCA AAT AGT        5947
Asp Tyr Arg Lys Pro His Val Tyr Asp Asn Cys Ala Asp Ala Asn Ser
```

```
                       945                        950                        955
TCA TCT TCA GAT AGC TGT TCA GAC AGT AGT AGT AGT AGT GAA TCT GAA           5995
Ser Ser Ser Asp Ser Cys Ser Asp Ser Ser Ser Ser Ser Glu Ser Glu
            960                     965                     970

TCT GAT TCA GAT GGA TGT TGC GAC ACA GAT GCT AGT TTA GAT TCT GAT           6043
Ser Asp Ser Asp Gly Cys Cys Asp Thr Asp Ala Ser Leu Asp Ser Asp
            975                     980                     985

ATT GAA AAT TGT TAT CAA AAT CCA TCA AAA TGT GAT GCA GGA TGC TAAATGAAAT
Ile Glu Asn Cys Tyr Gln Asn Pro Ser Lys Cys Asp Ala Gly Cys                6098
            990                     995                    1000

TTAATATTAT ATAATATTAA CTTACAAGTT ATAAAAATCA TTAAAATGAT TTTTAAAAT           6158
GATATTATCG ATAGTTGTGA TAATGTGCTC TTTTATTTTA TTAATTGCGA TGATTATAAT         6218
ATTATCTTTT AGATATATTT AATATTAATT ATAAATCGAC TGACAATAAT ATTTATTCCT         6278
ATTCATAATA ATCATCTGCT ATATATATTA ATGTATCATT CTCTATTATA AATATAGGTA         6338
TATTGTCTTT ATCAATCATT AATTTTGCTA CAGCTGTATT ATCTTATAT ACTATATTTG          6398
TGTCTTTGTT TAATAAACCT TTTAATATAG TGGCTCTATC ATAATCTTTA CAATATGATA         6458
TGGGATATAA TTTTATATTA ATAATAACAT TAGATACGTT CATTTCTTTC ATTCTAGTTT         6518
TACGTATTGT GTCAAAAATT ATTTCATTTT CTGCTGGTTC TATATATTTA TATGTGTTAT         6578
GAATAGATTC GATAGATGAT GATTTTAATA AATCAAATAT AACATTTATT TTACCTTGTT         6638
TATCTTTTAT AATATCTAAT ATTTCTTTAT CTACAGATTT TCTGTTGTTG GTATATGATA         6698
TTAAAAAATG AACGTTAACA TATCTATATT CTTGTGGTAA ATCTTATGA GAATTAATC           6758
TTATAGATCT TCCTATTATT TGTTTAATT CTGATTCATT CCACGGCATA TCTAATATAA          6818
TTATATCATT AATACATTTG AATGATATGC CTTCAGATCC AGCGTAAGAA AATATGCAAA         6878
CTTTTACTTT TTTACCATTA TTATTTTCAT AATTATTATA TTCGTTTAAT TCATTATCTC         6938
TAGTTTTTAA AGTTTTGCTA GAATATTCAA TATAAGAAAT ATTAAAACAA TTAAAATAAC         6998
ATTTTAAACT TGATATTCCT TCAAAATTAA CTAAAGGTTC AAATATTAAT ACTTTTCCTC         7058
TCGAATTTAA AATTATTTTA CAAGTTTCTA TATATTTACA CGAATATTGA TATAATATAT         7118
TATAATTATT TATATCAGTG ATTGGTAAAT TAGTTTTTAT TTTTATATTA TCATTTTTAA         7178
AACTTTCAAT AAAAGATTCA GAGAAATTAA TATTTTTTGT AAACTCGGAA AATTCAGCAA         7238
GTTTTCTTTT AATCATATCA TTATATTCTA TATTATCTAA ATCTCCTTTT ATTTAAGAT          7298
CATAAAAAGC AAATGAAGAT ATTAATCTTC TCATAGTTTT TAAACCACCT AATTCAGTTT         7358
TATAATCATA TTTTTCTGCC ATATTATATA ATTTAGATTG CTCATCTGAC ATAATTATAT         7418
TATGATAAAA TATATTTTTT TTTGCATATC CATCTATATA ATTTGTTTCT GTTAAACTAT         7478
CTGCTTCTAT TAATCTTTTA TAAGAACATA TAGCTAATAA TGTTTCTCTT AATTCCTTAA         7538
AATTAATTAA CTTTCCATTA TTTATATATT CTTCTTTTAT ATTCATAACA TTTGGTCTAA         7598
GTAAACCTAT TAAATTATTA AATTCAGAAA TATTATTAGT TACTGGAGTA GCGGACATAC         7658
ATAATATTTT ATTATTTTCG AAATTTGCTA ATTTATTAA TTTTTATAA ATAGGAGTAA          7718
AATTTCTTTC GTTATTATCT TTTTTAACAG TTCTTGATAT TAATTATGA ACTTCGTCTA          7778
TTATTATTAG TAATCTACTT TTTTTATTAA GAGAACTTTC TATAGATCTA TATATATTAT         7838
TAAATTTATC TAAACTAGAT GACGAATCAT AATATATAAA TTTTATATTA CTGGTATCTG         7898
ATATATATGA TCTTATAGTA TTTAACCAAG GATCTATGTA TAATGATTTT TAATAAATA          7958
TTAAAATTAT CCATCTTGGA AATAATTCTT TTATATATTT TATAATATAC ACAGCAGTTA         8018
ATGTTTTCC CATACCAGTA TCCCAAAATA ATAACATACT ATTCAAATTT TTTAATCCTA          8078
```

```
TGAATATTCT  ACTTACAAAA  TATTGATAAT  CTTGTAATGT  AATTTCAGTA  TTTGTAATAT    8138

TATTCATAAT  TTTATTAGGC  AAATGTTGTG  TTTTATCAAG  TGCATAATTT  ATATGTTTAC    8198

CAACAATAGA  ATCTAATGCA  AACATTTAGT  TATATAAAAA  ATAATATTTA  TATTAACTTA    8258

AGATGTTTCA  TTAATTTTAT  GTCTGTGATG  TGGAGTTAAA  ACCCAAGATA  TTGATATATC    8318

TATATCATTA  ATTCTTCTTT  TGAATCTATG  TCTATCAATC  GCAAATTTAT  CCCAGTATAA    8378

TTTTCGAGTT  TGTTTTGCAG  CATATAACCA  AACATACATA  ATGTGGAGTT  TTGGTGGTTC    8438

GGATGAAAAG  CGTACTTTT                                                    8457
```

( 2 ) INFORMATION FOR SEQ ID NO:2:

( i ) SEQUENCE CHARACTERISTICS:
        ( A ) LENGTH: 464 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Asn  Asn  Lys  Ile  Arg  Arg  Phe  Pro  Asn  Lys  Asn  Leu  Lys  Met  Pro
 1              5                        10                       15

Glu  Ser  Gly  Ile  Asn  Phe  Met  Ser  Met  Leu  Phe  Phe  Ser  Lys  Ile  Asp
              20                       25                       30

Asn  Met  Val  Tyr  Phe  Ile  Asn  Pro  Ile  Lys  Tyr  Asn  Thr  Asn  Ala  Asn
         35                       40                       45

Ile  Ala  Ile  Leu  Glu  Lys  Ile  Asp  Asp  Asp  Glu  Thr  Arg  Gly  Lys
    50                       55                       60

Val  Thr  Phe  Ile  Pro  Ile  Lys  Tyr  Leu  Glu  Ile  Leu  Tyr  Asn  Glu  Leu
65                       70                       75                       80

Val  Leu  Asp  Pro  Asn  His  Ile  Asn  Asn  Ile  Asn  Phe  Glu  Asn  Asn  Ile
                   85                       90                       95

Lys  Arg  Lys  Phe  Phe  Leu  Phe  Trp  Thr  Ile  Lys  Lys  Tyr  Leu  Gln  Asp
                  100                      105                      110

Lys  Asn  Ile  Asn  Ile  Asn  Thr  Phe  Ile  Thr  Ser  Lys  Lys  Tyr  Lys  Gly
              115                      120                      125

Ile  Pro  Leu  Val  Tyr  Met  Arg  Lys  Ser  Phe  Leu  Lys  Ser  Glu  Leu  Ser
    130                      135                      140

Lys  Thr  Arg  Asp  Phe  Ser  Thr  Phe  Ala  Thr  Ile  Tyr  Asp  Asp  Leu  Asp
145                      150                      155                      160

Ala  Gln  Ile  Gly  Ile  Pro  Pro  Leu  Gly  Phe  Asn  Pro  Lys  Pro  Lys  Ala
                   165                      170                      175

Tyr  Pro  Arg  Lys  His  Asp  Lys  Ser  Thr  Trp  Leu  Ser  Ser  Gly  Asp  Ile
                  180                      185                      190

Tyr  Asn  Cys  Ile  Tyr  Pro  Leu  Thr  Met  Ile  Asn  Thr  Asp  Tyr  Asp  Tyr
              195                      200                      205

Phe  His  Leu  Ile  Leu  Phe  Glu  Lys  Thr  Asp  Lys  Asn  Ile  Ala  Thr  Val
    210                      215                      220

Ala  Ser  Ser  Met  Arg  Cys  Tyr  Lys  Leu  Glu  Asp  Arg  Val  Lys  Phe  Phe
225                      230                      235                      240

Leu  Met  Asn  Asp  Lys  Lys  Arg  Phe  Phe  Met  Phe  Pro  Ile  Ile  Tyr  Asn
                   245                      250                      255

Asp  His  Phe  Thr  Cys  Cys  Val  Ile  Asp  Lys  His  Phe  Asp  Lys  Asp  Lys
                  260                      265                      270

Lys  Ala  Ala  Tyr  Phe  Phe  Asn  Ser  Ser  Gly  Tyr  Ile  Pro  Glu  Leu  Ile
```

|   |   |   | 275 |   |   |   |   | 280 |   |   |   |   | 285 |   |   |
|---|---|---|---|---|---|---|---|---|---|---|---|---|---|---|---|
| Lys | Gln | Asn | Lys | Lys | Tyr | Met | Phe | Ile | Glu | Ser | Asp | Met | Thr | Ile | Lys |
|   | 290 |   |   |   |   | 295 |   |   |   |   | 300 |   |   |   |   |
| Ser | His | Lys | His | Tyr | Asn | Ser | Thr | Pro | Asn | Thr | Asn | Tyr | Ala | Tyr | Leu |
| 305 |   |   |   | 310 |   |   |   |   | 315 |   |   |   |   |   | 320 |
| Tyr | Ile | Asp | Val | Leu | Ser | Glu | Tyr | Leu | Asn | Asp | Ile | Phe | Lys | Asn | Val |
|   |   |   |   | 325 |   |   |   |   | 330 |   |   |   |   | 335 |   |
| Asn | Tyr | Tyr | Phe | Phe | Asn | Thr | Phe | Glu | Leu | Gln | Tyr | Asp | Ser | Pro | Asp |
|   |   |   | 340 |   |   |   |   | 345 |   |   |   |   | 350 |   |   |
| Cys | Gly | Met | Phe | Asn | Ile | Ile | Phe | Leu | Tyr | Tyr | Ile | Val | Tyr | Phe | Asn |
|   |   | 355 |   |   |   |   | 360 |   |   |   |   | 365 |   |   |   |
| Ile | Lys | Ser | Lys | Phe | Glu | Phe | Lys | Lys | Leu | Tyr | Tyr | Ser | Met | Ser | Phe |
|   | 370 |   |   |   |   | 375 |   |   |   |   | 380 |   |   |   |   |
| Ile | Gly | Asp | Leu | Leu | Ala | Ser | Ser | Tyr | Arg | Gly | Ala | Leu | Phe | Ile | Ser |
| 385 |   |   |   |   | 390 |   |   |   |   | 395 |   |   |   |   | 400 |
| Arg | Tyr | Asp | Ile | Asn | Ser | Ile | Asp | Glu | Phe | Lys | Asn | Thr | Leu | Glu | Ile |
|   |   |   |   | 405 |   |   |   |   | 410 |   |   |   |   | 415 |   |
| Phe | Asn | Ile | Lys | Asn | Lys | Lys | Phe | Met | Glu | Leu | Ile | Asp | Met | Tyr | Lys |
|   |   |   | 420 |   |   |   |   | 425 |   |   |   |   | 430 |   |   |
| Lys | Asn | Ser | Asn | Arg | Ile | Met | Asn | Val | Cys | Ser | Lys | Ile | Lys | Asn | Asp |
|   |   | 435 |   |   |   |   | 440 |   |   |   |   | 445 |   |   |   |
| Tyr | Asp | Ser | Tyr | Ile | Asp | Asn | Glu | Lys | Asn | Ser | Leu | Glu | Ser | Asn | Ile |
|   | 450 |   |   |   |   | 455 |   |   |   |   | 460 |   |   |   |   |

(2) INFORMATION FOR SEQ ID NO:3:

(i) SEQUENCE CHARACTERISTICS:
        (A) LENGTH: 225 amino acids
        (B) TYPE: amino acid
        (D) TOPOLOGY: linear (ii) MOLECULE TYPE: protein (xi) SEQUENCE DESCRIPTION: SEQ ID NO:3:

| Met | Phe | Leu | Val | Tyr | Phe | Asn | Thr | Phe | Leu | Ile | Ile | Ile | Leu | Leu | Phe |
|---|---|---|---|---|---|---|---|---|---|---|---|---|---|---|---|
| 1 |   |   |   | 5 |   |   |   |   | 10 |   |   |   |   | 15 |   |
| Gly | Ile | Ile | Gly | Ile | Tyr | Ile | Leu | Thr | Phe | Val | Phe | Asn | Ile | Asp | Phe |
|   |   |   | 20 |   |   |   |   | 25 |   |   |   |   | 30 |   |   |
| Leu | Ile | Asn | Asn | Asn | Lys | Ile | Tyr | Ile | Leu | Ser | Tyr | Asn | Ala | Thr | Asn |
|   |   |   | 35 |   |   |   |   | 40 |   |   |   |   | 45 |   |   |
| Ile | Asn | Asn | Ile | Asn | Asn | Leu | Asn | Leu | Tyr | Asp | Tyr | Ser | Asp | Ile | Ile |
|   | 50 |   |   |   |   | 55 |   |   |   |   | 60 |   |   |   |   |
| Phe | Leu | Thr | Asn | Phe | Asn | Ile | Asn | Asn | Leu | Leu | Val | Thr | Gln | Ala |
| 65 |   |   |   |   | 70 |   |   |   |   | 75 |   |   |   |   | 80 |
| Asn | Asn | Leu | Gln | Asp | Ile | Pro | Ile | Phe | Asn | Val | Asn | Asn | Ile | Ile | Ser |
|   |   |   |   | 85 |   |   |   |   | 90 |   |   |   |   | 95 |   |
| Asn | Gln | Tyr | Asn | Phe | Tyr | Ser | Ala | Ser | Ser | Asn | Asn | Val | Asn | Ile | Leu |
|   |   |   | 100 |   |   |   |   | 105 |   |   |   |   | 110 |   |   |
| Leu | Gly | Leu | Arg | Lys | Thr | Leu | Asn | Ile | Asn | Arg | Asn | Pro | Phe | Leu | Leu |
|   |   |   | 115 |   |   |   |   | 120 |   |   |   |   | 125 |   |   |
| Phe | Arg | Asn | Thr | Ser | Leu | Ala | Ile | Val | Phe | Asn | Asn | Asn | Glu | Thr | Phe |
|   |   | 130 |   |   |   |   | 135 |   |   |   |   | 140 |   |   |   |
| His | Cys | Tyr | Ile | Ser | Ser | Asn | Gln | Asn | Ser | Asp | Val | Leu | Asp | Ile | Val |
| 145 |   |   |   |   | 150 |   |   |   |   | 155 |   |   |   |   | 160 |
| Ser | His | Ile | Glu | Phe | Met | Lys | Ser | Arg | Tyr | Asn | Lys | Tyr | Val | Ile | Ile |
|   |   |   |   | 165 |   |   |   |   | 170 |   |   |   |   | 175 |   |

```
Gly  Glu  Ile  Pro  Val  Asn  Asn  Asn  Ile  Ser  Ile  Asn  Asn  Ile  Leu  Asn
              180                      185                      190

Asn  Phe  Ala  Ile  Ile  Thr  Asn  Val  Arg  Leu  Ile  Asp  Lys  Tyr  Asn  Ser
         195                      200                      205

Ile  Ile  Ser  Phe  Leu  Asn  Ile  Asn  Val  Gly  Thr  Leu  Phe  Val  Ile  Asn
    210                      215                      220

Pro
225
```

( 2 ) INFORMATION FOR SEQ ID NO:4:

( i ) SEQUENCE CHARACTERISTICS:
        ( A ) LENGTH: 78 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Ser  Ser  Ser  Lys  Lys  Asn  Asn  Leu  Gly  Tyr  Phe  Asn  Asn  Leu  Lys
 1                   5                        10                       15

Thr  Glu  Glu  Val  Ser  Gln  Ser  Gln  Val  Phe  Lys  Asp  Asn  Tyr  Arg  Pro
              20                      25                       30

Gly  Tyr  Tyr  Gly  Leu  Asp  Thr  Asn  Ala  Ala  Asn  Pro  Ala  Asp  Val  Tyr
         35                      40                       45

Asn  Thr  Glu  Ser  Asn  Lys  Pro  Ser  Thr  Val  Asp  Val  Trp  Gly  Asp  Lys
    50                      55                       60

Arg  Leu  Glu  Gly  Lys  Ile  Ile  Pro  Lys  Ser  Lys  Lys  Lys
65                       70                       75
```

( 2 ) INFORMATION FOR SEQ ID NO:5:

( i ) SEQUENCE CHARACTERISTICS:
        ( A ) LENGTH: 161 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met  Ser  Ile  Phe  Ile  Tyr  Tyr  Ile  Phe  Asn  Asn  Arg  Phe  Tyr  Ile  Tyr
 1                   5                        10                       15

Lys  Arg  Met  Asn  Thr  Val  Gln  Ile  Leu  Val  Val  Ile  Leu  Ile  Thr  Thr
              20                      25                       30

Ala  Leu  Ser  Phe  Leu  Val  Phe  Gln  Leu  Trp  Tyr  Tyr  Ala  Glu  Asn  Tyr
         35                      40                       45

Glu  Tyr  Ile  Leu  Arg  Tyr  Asn  Asp  Thr  Tyr  Ser  Asn  Leu  Gln  Phe  Ala
    50                      55                       60

Arg  Ser  Ala  Asn  Ile  Asn  Phe  Asp  Asp  Leu  Thr  Val  Phe  Asp  Pro  Asn
65                       70                       75                       80

Asp  Asn  Val  Phe  Asn  Val  Glu  Glu  Lys  Trp  Arg  Cys  Ala  Ser  Thr  Asn
              85                       90                       95

Asn  Asn  Ile  Phe  Tyr  Ala  Val  Ser  Thr  Phe  Gly  Phe  Leu  Ser  Thr  Glu
             100                      105                      110

Ser  Thr  Gly  Ile  Asn  Leu  Thr  Tyr  Thr  Asn  Ser  Arg  Asp  Cys  Ile  Ile
         115                      120                      125

Asp  Leu  Phe  Ser  Arg  Ile  Ile  Lys  Ile  Val  Tyr  Asp  Pro  Cys  Thr  Val
    130                      135                      140
```

| | | | | | | | | | | | | | | | |
|---|---|---|---|---|---|---|---|---|---|---|---|---|---|---|---|
| Glu | Thr | Ser | Asn | Asp | Cys | Arg | Leu | Leu | Arg | Leu | Leu | Met | Ala | Asn | Thr |
| 145 | | | | | 150 | | | | 155 | | | | | | 160 |

Ser (2) INFORMATION FOR SEQ ID NO:6:

(i) SEQUENCE CHARACTERISTICS:
        (A) LENGTH: 1003 amino acids
        (B) TYPE: amino acid
        (D) TOPOLOGY: linear (ii) MOLECULE TYPE: protein (xi) SEQUENCE DESCRIPTION: SEQ ID NO:6:

| | | | | | | | | | | | | | | | |
|---|---|---|---|---|---|---|---|---|---|---|---|---|---|---|---|
| Met | Ser | Asn | Val | Pro | Leu | Ala | Thr | Lys | Thr | Ile | Arg | Lys | Leu | Ser | Asn |
| 1 | | | | 5 | | | | | 10 | | | | | 15 | |
| Arg | Lys | Tyr | Glu | Ile | Lys | Ile | Tyr | Leu | Lys | Asp | Glu | Asn | Thr | Cys | Phe |
| | | | 20 | | | | | 25 | | | | | 30 | | |
| Glu | Arg | Val | Val | Asp | Met | Val | Val | Pro | Leu | Tyr | Asp | Val | Cys | Asn | Glu |
| | | | 35 | | | | 40 | | | | | 45 | | | |
| Thr | Ser | Gly | Val | Thr | Leu | Glu | Ser | Cys | Ser | Pro | Asn | Ile | Glu | Val | Ile |
| | 50 | | | | | 55 | | | | | 60 | | | | |
| Glu | Leu | Asp | Asn | Thr | His | Val | Arg | Ile | Lys | Val | His | Gly | Asp | Thr | Leu |
| 65 | | | | | 70 | | | | | 75 | | | | | 80 |
| Lys | Glu | Met | Cys | Phe | Glu | Leu | Leu | Phe | Pro | Cys | Asn | Val | Asn | Glu | Ala |
| | | | | 85 | | | | | 90 | | | | | 95 | |
| Gln | Val | Trp | Lys | Tyr | Val | Ser | Arg | Leu | Leu | Leu | Asp | Asn | Val | Ser | His |
| | | | 100 | | | | | 105 | | | | | 110 | | |
| Asn | Asp | Val | Lys | Tyr | Lys | Leu | Ala | Asn | Phe | Arg | Leu | Thr | Leu | Asn | Gly |
| | | 115 | | | | | 120 | | | | | 125 | | | |
| Lys | His | Leu | Lys | Leu | Lys | Glu | Ile | Asp | Gln | Pro | Leu | Phe | Ile | Tyr | Phe |
| | 130 | | | | | 135 | | | | | 140 | | | | |
| Val | Asp | Asp | Leu | Gly | Asn | Tyr | Gly | Leu | Ile | Thr | Lys | Glu | Asn | Ile | Gln |
| 145 | | | | | 150 | | | | | 155 | | | | | 160 |
| Asn | Asn | Asn | Leu | Gln | Val | Asn | Lys | Asp | Ala | Ser | Phe | Ile | Thr | Ile | Phe |
| | | | | 165 | | | | | 170 | | | | | 175 | |
| Pro | Gln | Tyr | Ala | Tyr | Ile | Cys | Leu | Gly | Arg | Lys | Val | Tyr | Leu | Asn | Glu |
| | | | 180 | | | | | 185 | | | | | 190 | | |
| Lys | Val | Thr | Phe | Asp | Val | Thr | Thr | Asp | Ala | Thr | Asn | Ile | Thr | Leu | Asp |
| | | 195 | | | | | 200 | | | | | 205 | | | |
| Phe | Asn | Lys | Ser | Val | Asn | Ile | Ala | Val | Ser | Phe | Leu | Asp | Ile | Tyr | Tyr |
| | 210 | | | | | 215 | | | | | 220 | | | | |
| Glu | Val | Asn | Asn | Asn | Glu | Gln | Lys | Asp | Leu | Leu | Lys | Asp | Leu | Leu | Lys |
| 225 | | | | | 230 | | | | | 235 | | | | | 240 |
| Arg | Tyr | Gly | Glu | Phe | Glu | Val | Tyr | Asn | Ala | Asp | Thr | Gly | Leu | Ile | Tyr |
| | | | | 245 | | | | | 250 | | | | | 255 | |
| Ala | Lys | Asn | Leu | Ser | Ile | Lys | Asn | Tyr | Asp | Thr | Val | Ile | Gln | Val | Glu |
| | | | 260 | | | | | 265 | | | | | 270 | | |
| Arg | Leu | Pro | Val | Asn | Leu | Lys | Val | Arg | Ala | Tyr | Thr | Lys | Asp | Glu | Asn |
| | | 275 | | | | | 280 | | | | | 285 | | | |
| Gly | Arg | Asn | Leu | Cys | Leu | Met | Lys | Ile | Thr | Ser | Ser | Thr | Glu | Val | Asp |
| | 290 | | | | | 295 | | | | | 300 | | | | |
| Pro | Glu | Tyr | Val | Thr | Ser | Asn | Asn | Ala | Leu | Leu | Gly | Thr | Leu | Arg | Val |
| 305 | | | | | 310 | | | | | 315 | | | | | 320 |
| Tyr | Lys | Lys | Phe | Asp | Lys | Ser | His | Leu | Lys | Ile | Val | Met | His | Asn | Arg |
| | | | | 325 | | | | | 330 | | | | | 335 | |

```
Gly  Ser  Gly  Asn  Val  Phe  Pro  Leu  Arg  Ser  Leu  Tyr  Leu  Glu  Leu  Ser
               340                 345                 350

Asn  Val  Lys  Gly  Tyr  Pro  Val  Lys  Ala  Ser  Asp  Thr  Ser  Arg  Leu  Asp
          355                      360                 365

Val  Gly  Ile  Tyr  Lys  Leu  Asn  Lys  Ile  Tyr  Val  Asp  Asn  Asp  Glu  Asn
     370                      375                 380

Lys  Ile  Ile  Leu  Glu  Glu  Ile  Glu  Ala  Glu  Tyr  Arg  Cys  Gly  Arg  Gln
385                      390                 395                           400

Val  Phe  His  Glu  Arg  Val  Lys  Leu  Asn  Lys  His  Gln  Cys  Lys  Tyr  Thr
               405                      410                           415

Pro  Lys  Cys  Pro  Phe  Gln  Phe  Val  Val  Asn  Ser  Pro  Asp  Thr  Thr  Ile
               420                 425                      430

His  Leu  Tyr  Gly  Ile  Ser  Asn  Val  Cys  Leu  Lys  Pro  Lys  Val  Pro  Lys
          435                 440                      445

Asn  Leu  Arg  Leu  Trp  Gly  Trp  Ile  Leu  Asp  Cys  Asp  Thr  Ser  Arg  Phe
450                      455                 460

Ile  Lys  His  Met  Ala  Asp  Gly  Ser  Asp  Asp  Leu  Asp  Leu  Asp  Val  Arg
465                 470                 475                           480

Leu  Asn  Arg  Asn  Asp  Ile  Cys  Leu  Lys  Gln  Ala  Ile  Lys  Gln  His  Tyr
               485                 490                           495

Thr  Asn  Val  Ile  Ile  Leu  Glu  Tyr  Ala  Asn  Thr  Tyr  Pro  Asn  Cys  Thr
               500                 505                      510

Leu  Ser  Leu  Gly  Asn  Asn  Arg  Phe  Asn  Asn  Val  Phe  Asp  Met  Asn  Asp
          515                 520                 525

Asn  Lys  Thr  Ile  Ser  Glu  Tyr  Thr  Asn  Phe  Thr  Lys  Ser  Arg  Gln  Asp
     530                      535                 540

Leu  Asn  Asn  Met  Ser  Cys  Ile  Leu  Gly  Ile  Asn  Ile  Gly  Asn  Ser  Val
545                 550                 555                           560

Asn  Ile  Ser  Ser  Leu  Pro  Gly  Trp  Val  Thr  Pro  His  Glu  Ala  Lys  Ile
               565                 570                           575

Leu  Arg  Ser  Gly  Cys  Ala  Arg  Val  Arg  Glu  Phe  Cys  Lys  Ser  Phe  Cys
               580                 585                 590

Asp  Leu  Ser  Asn  Lys  Arg  Phe  Tyr  Ala  Met  Ala  Arg  Asp  Leu  Val  Ser
          595                      600                 605

Leu  Leu  Phe  Met  Cys  Asn  Tyr  Val  Asn  Ile  Glu  Ile  Asn  Glu  Ala  Val
     610                 615                 620

Cys  Glu  Tyr  Pro  Gly  Tyr  Val  Ile  Leu  Phe  Ala  Arg  Ala  Ile  Lys  Val
625                      630                 635                      640

Ile  Asn  Asp  Leu  Leu  Leu  Ile  Asn  Gly  Val  Asp  Asn  Leu  Ala  Gly  Tyr
               645                      650                      655

Ser  Ile  Ser  Leu  Pro  Ile  His  Tyr  Gly  Ser  Thr  Glu  Lys  Thr  Leu  Pro
               660                 665                      670

Asn  Glu  Lys  Tyr  Gly  Gly  Val  Asp  Lys  Lys  Phe  Lys  Tyr  Leu  Phe  Leu
          675                 680                 685

Lys  Asn  Lys  Leu  Lys  Asp  Leu  Met  Arg  Asp  Ala  Asp  Phe  Val  Gln  Pro
     690                 695                      700

Pro  Leu  Tyr  Ile  Ser  Thr  Tyr  Phe  Arg  Thr  Leu  Leu  Asp  Ala  Pro  Pro
705                      710                 715                           720

Thr  Asp  Asn  Tyr  Glu  Lys  Tyr  Leu  Val  Asp  Ser  Ser  Val  Gln  Ser  Gln
                    725                 730                      735

Asp  Val  Leu  Gln  Gly  Leu  Leu  Asn  Thr  Cys  Asn  Thr  Ile  Asp  Thr  Asn
               740                      745                      750
```

```
Ala  Arg  Val  Ala  Ser  Ser  Val  Ile  Gly  Tyr  Val  Tyr  Glu  Pro  Cys  Gly
          755                 760                 765

Thr  Ser  Glu  His  Lys  Ile  Gly  Ser  Glu  Ala  Leu  Cys  Lys  Met  Ala  Lys
     770                 775                 780

Glu  Ala  Ser  Arg  Leu  Gly  Asn  Leu  Gly  Leu  Val  Asn  Arg  Ile  Asn  Glu
785                      790                 795                           800

Ser  Asn  Tyr  Asn  Lys  Cys  Asn  Lys  Tyr  Gly  Tyr  Arg  Gly  Val  Tyr  Glu
               805                      810                           815

Asn  Asn  Lys  Leu  Lys  Thr  Lys  Tyr  Tyr  Arg  Glu  Ile  Phe  Asp  Cys  Asn
               820                      825                 830

Pro  Asn  Asn  Asn  Asn  Glu  Leu  Ile  Ser  Arg  Tyr  Gly  Tyr  Arg  Ile  Met
          835                      840                      845

Asp  Leu  His  Lys  Ile  Gly  Glu  Ile  Phe  Ala  Asn  Tyr  Asp  Glu  Ser  Glu
     850                      855                      860

Ser  Pro  Cys  Glu  Arg  Arg  Cys  His  Tyr  Leu  Glu  Asp  Arg  Gly  Leu  Leu
865                      870                      875                      880

Tyr  Gly  Pro  Glu  Tyr  Val  His  His  Arg  Tyr  Gln  Glu  Ser  Cys  Thr  Pro
                    885                      890                 895

Asn  Thr  Phe  Gly  Asn  Asn  Thr  Asn  Cys  Val  Thr  Arg  Asn  Gly  Glu  Gln
               900                      905                      910

His  Val  Tyr  Glu  Asn  Ser  Cys  Gly  Asp  Asn  Ala  Thr  Cys  Gly  Arg  Arg
          915                      920                      925

Thr  Gly  Tyr  Gly  Arg  Arg  Ser  Arg  Asp  Glu  Trp  Asn  Asp  Tyr  Arg  Lys
     930                      935                      940

Pro  His  Val  Tyr  Asp  Asn  Cys  Ala  Asp  Ala  Asn  Ser  Ser  Ser  Ser  Asp
945                      950                      955                      960

Ser  Cys  Ser  Asp  Ser  Ser  Ser  Ser  Glu  Ser  Glu  Ser  Asp  Ser  Asp
               965                      970                      975

Gly  Cys  Cys  Asp  Thr  Asp  Ala  Ser  Leu  Asp  Ser  Asp  Ile  Glu  Asn  Cys
               980                      985                 990

Tyr  Gln  Asn  Pro  Ser  Lys  Cys  Asp  Ala  Gly  Cys
          995                      1000
```

( 2 ) INFORMATION FOR SEQ ID NO:7:

( i ) SEQUENCE CHARACTERISTICS:
        ( A ) LENGTH: 163 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Arg  Ser  Ile  Arg  Leu  Asn  Ser  His  Lys  Asp  Leu  Pro  Gln  Glu  Tyr  Arg
1                   5                   10                       15

Tyr  Val  Asn  Val  His  Phe  Leu  Ile  Ser  Tyr  Thr  Asn  Asn  Arg  Lys  Ser
               20                  25                       30

Val  Asp  Lys  Glu  Ile  Leu  Asp  Ile  Ile  Lys  Asp  Lys  Gln  Gly  Lys  Ile
          35                       40                  45

Asn  Val  Ile  Phe  Asp  Leu  Leu  Lys  Ser  Ser  Ser  Ile  Glu  Ser  Ile  His
     50                  55                       60

Asn  Thr  Tyr  Lys  Tyr  Ile  Glu  Pro  Ala  Glu  Asn  Glu  Ile  Ile  Phe  Asp
65                       70                  75                            80

Thr  Ile  Arg  Lys  Thr  Arg  Met  Lys  Glu  Met  Asn  Val  Ser  Asn  Val  Ile
               85                  90                            95

Ile  Asn  Ile  Lys  Leu  Tyr  Pro  Ile  Ser  Tyr  Cys  Lys  Asp  Tyr  Asp  Arg
```

|  |  |  | 100 |  |  |  | 105 |  |  |  | 110 |  |  |
|---|---|---|---|---|---|---|---|---|---|---|---|---|---|
| Ala | Thr | Ile | Leu | Lys | Gly | Leu | Leu | Asn | Lys | Asp | Thr | Asn | Ile | Val | Tyr |
|  |  | 115 |  |  |  |  | 120 |  |  |  |  | 125 |  |  |

Lys Asp Asn Thr Ala Val Ala Lys Leu Met Ile Asp Lys Asp Asn Ile
130                         135                 140

Pro Ile Phe Ile Ile Glu Asn Asp Thr Leu Ile Tyr Ile Ala Asp Asp
145                 150                     155                 160

Tyr Tyr Glu ( 2 ) INFORMATION FOR SEQ ID NO:8:

( i ) SEQUENCE CHARACTERISTICS:
        ( A ) LENGTH: 1511 base pairs
        ( B ) TYPE: nucleic acid
        ( C ) STRANDEDNESS: double
        ( D ) TOPOLOGY: unknown ( i i ) MOLECULE TYPE: DNA (genomic)

( v i ) ORIGINAL SOURCE:
        ( A ) ORGANISM: Amsacta moorei entemopoxvirus ( i x ) FEATURE:

```
         30                         35                         40                         45
ATA  ATA  TAT  TAT  GAT  AAT  AAT  ATT  TTA  AAT  AAT  ATT  CCA  GAA  AAT  ATT          1034
Ile  Ile  Tyr  Tyr  Asp  Asn  Asn  Ile  Leu  Asn  Asn  Ile  Pro  Glu  Asn  Ile
                         50                         55                         60

AAA  AGT  TTA  TAT  ATT  TCA  AAT  TTA  AAT  ATT  ATT  AAT  TTA  AAT  TTT  ATA          1082
Lys  Ser  Leu  Tyr  Ile  Ser  Asn  Leu  Asn  Ile  Ile  Asn  Leu  Asn  Phe  Ile
               65                         70                         75

ACA  AAA  TTA  AAA  AAT  ATA  ACA  TAT  TTA  GAT  ATA  TCT  TAT  AAC  AAA  AAT          1130
Thr  Lys  Leu  Lys  Asn  Ile  Thr  Tyr  Leu  Asp  Ile  Ser  Tyr  Asn  Lys  Asn
                    80                         85                         90

AGC  AAT  ATA  AGT  AAT  ATT  ATA  CTA  CCA  CAT  TCT  ATA  GAA  TTT  TTA  AAT          1178
Ser  Asn  Ile  Ser  Asn  Ile  Ile  Leu  Pro  His  Ser  Ile  Glu  Phe  Leu  Asn
          95                        100                        105

TGT  GAA  TCA  TGT  AAT  ATA  AAT  GAC  TAT  AAT  TTT  ATT  AAT  AAT  TTA  GTA          1226
Cys  Glu  Ser  Cys  Asn  Ile  Asn  Asp  Tyr  Asn  Phe  Ile  Asn  Asn  Leu  Val
110                      115                        120                        125

AAT  TTA  AAA  AAA  TTA  ATA  ATA  TCT  AAA  AAT  AAA  TTT  GGT  AAC  TTT  AAT          1274
Asn  Leu  Lys  Lys  Leu  Ile  Ile  Ser  Lys  Asn  Lys  Phe  Gly  Asn  Phe  Asn
                    130                        135                        140

AAT  GTT  TTT  CCT  ATT  AGT  ATA  GTT  GAG  TTA  AAT  ATG  GAA  TCA  ATA  CAA          1322
Asn  Val  Phe  Pro  Ile  Ser  Ile  Val  Glu  Leu  Asn  Met  Glu  Ser  Ile  Gln
               145                        150                        155

ATA  AAA  GAT  TAT  AAA  TTT  ATA  GAA  AAA  TTA  ATT  AAT  TTA  AAA  AAA  TTA          1370
Ile  Lys  Asp  Tyr  Lys  Phe  Ile  Glu  Lys  Leu  Ile  Asn  Leu  Lys  Lys  Leu
          160                        165                        170

GAT  ATA  TCT  TTC  AAT  GTT  AAA  AAA  AAT  AAT  ATA  CAT  TTG  ATA  AAA  TTT          1418
Asp  Ile  Ser  Phe  Asn  Val  Lys  Lys  Asn  Asn  Ile  His  Leu  Ile  Lys  Phe
     175                        180                        185

CCA  AAA  AGT  ATA  ACT  CAT  TTA  TGT  GAT  TAT  CAA  TCA  TAT  AAA  GAA  AAT          1466
Pro  Lys  Ser  Ile  Thr  His  Leu  Cys  Asp  Tyr  Gln  Ser  Tyr  Lys  Glu  Asn
190                      195                        200                        205

TAT  AAT  TAT  TTA  AAA  AAT  TTA  TCA  AAT  ATA  ATT  GAA  TAT  GAA  TTC               1511
Tyr  Asn  Tyr  Leu  Lys  Asn  Leu  Ser  Asn  Ile  Ile  Glu  Tyr  Glu  Phe
                    210                        215                        220
```

( 2 ) INFORMATION FOR SEQ ID NO:9:

( i ) SEQUENCE CHARACTERISTICS:
        ( A ) LENGTH: 66 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

```
Met  Gln  Asn  Asn  Asp  Asn  Tyr  Tyr  Ser  Asp  Ile  Glu  Gly  Ala  Lys  Ser
 1                    5                        10                        15

Asp  Ile  Ser  Leu  Val  Asp  Arg  Lys  Lys  Lys  Ile  Gly  Lys  Met  Ile  Asn
                    20                        25                        30

Asn  Ile  Val  Asn  Ile  Asn  Asn  Glu  Leu  Asn  Lys  Gln  Leu  Ser  Asn  Asn
               35                        40                        45

Asn  Lys  Met  Leu  Lys  Asn  Leu  Leu  Asp  Ser  Leu  Lys  Lys  Tyr  Asp  Cys
     50                        55                        60

Cys  Leu
 65
```

( 2 ) INFORMATION FOR SEQ ID NO:10:

( i ) SEQUENCE CHARACTERISTICS:
        ( A ) LENGTH: 182 amino acids
        ( B ) TYPE: amino acid (D) TOPOLOGY: linear (ii) MOLECULE TYPE: protein (xi) SEQUENCE DESCRIPTION: SEQ ID NO:10:

| Met | Ser | Ile | Glu | Leu | Ile | Ile | Gly | Pro | Met | Phe | Ser | Gly | Lys | Thr | Thr |
|---|---|---|---|---|---|---|---|---|---|---|---|---|---|---|---|
| 1 | | | | 5 | | | | | 10 | | | | | 15 | |
| Glu | Leu | Met | Arg | Lys | Ile | Asn | Arg | Tyr | Ile | Leu | Ser | Asn | Gln | Lys | Cys |
| | | | 20 | | | | | 25 | | | | | 30 | | |
| Val | Ile | Ile | Thr | His | Asn | Ile | Asp | Asn | Arg | Phe | Ile | Asn | Lys | Asn | Ile |
| | | | 35 | | | | 40 | | | | | 45 | | | |
| Ile | Asn | His | Asp | Gly | Asn | Ile | Leu | Asn | Lys | Glu | Tyr | Leu | Tyr | Ile | Lys |
| | | | 50 | | | | 55 | | | | | 60 | | | |
| Thr | Asn | Asn | Leu | Ile | Asn | Glu | Ile | Asn | Ile | Val | Asp | Asn | Tyr | Asp | Ile |
| 65 | | | | | 70 | | | | | 75 | | | | | 80 |
| Ile | Gly | Ile | Asp | Glu | Cys | Gln | Phe | Phe | Glu | Glu | Asn | Asp | Leu | Glu | Gln |
| | | | | 85 | | | | | 90 | | | | | 95 | |
| Phe | Cys | Asp | Lys | Met | Ala | Asn | Asn | Lys | Lys | Lys | Val | Ile | Val | Ala | Gly |
| | | | | 100 | | | | | 105 | | | | | 110 | |
| Leu | Asn | Cys | Asp | Phe | Asn | Arg | Asn | Ile | Phe | Asn | Ser | Ile | Ser | Lys | Leu |
| | | | 115 | | | | | 120 | | | | | 125 | | |
| Ile | Pro | Lys | Val | Glu | Lys | Ile | Lys | Lys | Leu | Gln | Ala | Ile | Cys | Gln | Phe |
| | | 130 | | | | | 135 | | | | | 140 | | | |
| Cys | Tyr | Lys | Asp | Ala | Ser | Phe | Thr | Ile | Lys | Lys | His | Asn | Lys | Asn | Gln |
| 145 | | | | | 150 | | | | | 155 | | | | | 160 |
| Ile | Ile | Glu | Ile | Gly | Gly | Gln | Asp | Leu | Tyr | Val | Pro | Val | Cys | Arg | Leu |
| | | | | 165 | | | | | 170 | | | | | 175 | |
| Cys | Tyr | Asn | Asn | Ser | Tyr | | | | | | | | | | |
| | | | 180 | | | | | | | | | | | | |

(2) INFORMATION FOR SEQ ID NO:11:

(i) SEQUENCE CHARACTERISTICS:
(A) LENGTH: 220 amino acids
(B) TYPE: amino acid
(D) TOPOLOGY: linear (ii) MOLECULE TYPE: protein (xi) SEQUENCE DESCRIPTION: SEQ ID NO:11:

| Met | Asp | Leu | Leu | Asn | Ser | Asp | Ile | Ile | Leu | Ile | Asn | Ile | Leu | Lys | Tyr |
|---|---|---|---|---|---|---|---|---|---|---|---|---|---|---|---|
| 1 | | | | 5 | | | | | 10 | | | | | 15 | |
| Tyr | Asn | Leu | Lys | Lys | Ile | Ile | Ile | Asn | Arg | Asp | Asn | Val | Ile | Asn | Ile |
| | | | 20 | | | | | 25 | | | | | 30 | | |
| Asn | Ile | Leu | Lys | Lys | Leu | Val | Asn | Leu | Glu | Glu | Leu | His | Ile | Ile | Tyr |
| | | | 35 | | | | | 40 | | | | | 45 | | |
| Tyr | Asp | Asn | Asn | Ile | Leu | Asn | Asn | Ile | Pro | Glu | Asn | Ile | Lys | Ser | Leu |
| | | | 50 | | | | 55 | | | | | 60 | | | |
| Tyr | Ile | Ser | Asn | Leu | Asn | Ile | Ile | Asn | Leu | Asn | Phe | Ile | Thr | Lys | Leu |
| 65 | | | | | 70 | | | | | 75 | | | | | 80 |
| Lys | Asn | Ile | Thr | Tyr | Leu | Asp | Ile | Ser | Tyr | Asn | Lys | Asn | Ser | Asn | Ile |
| | | | | 85 | | | | | 90 | | | | | 95 | |
| Ser | Asn | Ile | Ile | Leu | Pro | His | Ser | Ile | Glu | Phe | Leu | Asn | Cys | Glu | Ser |
| | | | | 100 | | | | | 105 | | | | | 110 | |
| Cys | Asn | Ile | Asn | Asp | Tyr | Asn | Phe | Ile | Asn | Asn | Leu | Val | Asn | Leu | Lys |
| | | | 115 | | | | | 120 | | | | | 125 | | |
| Lys | Leu | Ile | Ile | Ser | Lys | Asn | Lys | Phe | Gly | Asn | Phe | Asn | Asn | Val | Phe |

```
                130                           135                           140
Pro  Ile  Ser  Ile  Val  Glu  Leu  Asn  Met  Glu  Ser  Ile  Gln  Ile  Lys  Asp
145                      150                      155                      160

Tyr  Lys  Phe  Ile  Glu  Lys  Leu  Ile  Asn  Leu  Lys  Lys  Leu  Asp  Ile  Ser
                    165                      170                      175

Phe  Asn  Val  Lys  Lys  Asn  Asn  Ile  His  Leu  Ile  Lys  Phe  Pro  Lys  Ser
               180                      185                      190

Ile  Thr  His  Leu  Cys  Asp  Tyr  Gln  Ser  Tyr  Lys  Glu  Asn  Tyr  Asn  Tyr
          195                      200                      205

Leu  Lys  Asn  Leu  Ser  Asn  Ile  Ile  Glu  Tyr  Glu  Phe
     210                      215                      220
```

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:12:

GAAGTNGATC CNGAATATGT                        20

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:13:

TTTCAAATTA ACTGGCAACC                        20

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:14:

GGGATGGATT TTAGATTGCG                        20

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:15:

GCCTGGTTGG GTAACACCTC                        20

( 2 ) INFORMATION FOR SEQ ID NO:16:

( i ) SEQUENCE CHARACTERISTICS:
 ( A ) LENGTH: 20 base pairs
 ( B ) TYPE: nucleic acid
 ( C ) STRANDEDNESS: single
 ( D ) TOPOLOGY: unknown ( i i ) MOLECULE TYPE: DNA (genomic)

( x i ) SEQUENCE DESCRIPTION: SEQ ID NO:16:

CTGCTAGATT ATCTACTCCG 20

( 2 ) INFORMATION FOR SEQ ID NO:17:

( i ) SEQUENCE CHARACTERISTICS:
 ( A ) LENGTH: 35 base pairs
 ( B ) TYPE: nucleic acid
 ( C ) STRANDEDNESS: single
 ( D ) TOPOLOGY: unknown ( i i ) MOLECULE TYPE: DNA (genomic)

( x i ) SEQUENCE DESCRIPTION: SEQ ID NO:17:

GTTCGAAACA AGTATTTTCA TCTTTTAAAT AAATC 35

( 2 ) INFORMATION FOR SEQ ID NO:18:

( i ) SEQUENCE CHARACTERISTICS:
 ( A ) LENGTH: 20 base pairs
 ( B ) TYPE: nucleic acid
 ( C ) STRANDEDNESS: single
 ( D ) TOPOLOGY: unknown ( i i ) MOLECULE TYPE: DNA (genomic)

( x i ) SEQUENCE DESCRIPTION: SEQ ID NO:18:

GAYGARGGRG GRCARTTYTT 20

( 2 ) INFORMATION FOR SEQ ID NO:19:

( i ) SEQUENCE CHARACTERISTICS:
 ( A ) LENGTH: 17 base pairs
 ( B ) TYPE: nucleic acid
 ( C ) STRANDEDNESS: single
 ( D ) TOPOLOGY: unknown ( i i ) MOLECULE TYPE: DNA (genomic)

( x i ) SEQUENCE DESCRIPTION: SEQ ID NO:19:

GGNCCCATGT TYTCNGG 17

( 2 ) INFORMATION FOR SEQ ID NO:20:

( i ) SEQUENCE CHARACTERISTICS:
 ( A ) LENGTH: 20 base pairs
 ( B ) TYPE: nucleic acid
 ( C ) STRANDEDNESS: single
 ( D ) TOPOLOGY: unknown ( i i ) MOLECULE TYPE: DNA (genomic)

( x i ) SEQUENCE DESCRIPTION: SEQ ID NO:20:

GGTGCAAAAT CTGATATTTC 20

( 2 ) INFORMATION FOR SEQ ID NO:21:

( i ) SEQUENCE CHARACTERISTICS:
 ( A ) LENGTH: 3012 base pairs
 ( B ) TYPE: nucleic acid ( C ) STRANDEDNESS: double
( D ) TOPOLOGY: unknown ( i i ) MOLECULE TYPE: DNA (genomic)

( x i ) SEQUENCE DESCRIPTION: SEQ ID NO:21:

| | | | | | | |
|---|---|---|---|---|---|---|
| ATGAGTAACG | TACCTTTAGC | AACCAAAACA | ATAAGAAAAT | TATCAAATCG | AAAATATGAA | 60 |
| ATAAAGATTT | ATTTAAAAGA | TGAAAATACT | TGTTTCGAAC | GTGTAGTAGA | TATGGTAGTT | 120 |
| CCATTATATG | ATGTGTGTAA | TGAAACTTCT | GGTGTTACTT | TAGAATCATG | TAGTCCAAAT | 180 |
| ATAGAAGTAA | TTGAATTAGA | CAATACTCAT | GTTAGAATCA | AAGTTCACGG | CGATACATTA | 240 |
| AAAGAAATGT | GTTTTGAATT | ATTGTTCCCG | TGTAATGTAA | ACGAAGCCCA | AGTATGGAAA | 300 |
| TATGTAAGTC | GATTATTGCT | AGATAATGTA | TCACATAATG | ACGTAAAATA | TAAATTAGCT | 360 |
| AATTTTAGAC | TGACTCTTAA | TGGAAAACAT | TTAAAATTAA | AAGAAATCGA | TCAACCGCTA | 420 |
| TTTATTTATT | TTGTCGATGA | TTTGGGAAAT | TATGGATTAA | TTACTAAGGA | AAATATTCAA | 480 |
| AATAATAATT | TACAAGTTAA | CAAAGATGCA | TCATTTATTA | CTATATTTCC | ACAATATGCG | 540 |
| TATATTTGTT | TAGGTAGAAA | AGTATATTTA | AATGAAAAAG | TAACTTTTGA | TGTAACTACA | 600 |
| GATGCAACTA | ATATTACTTT | AGATTTTAAT | AAATCTGTTA | ATATCGCAGT | ATCATTCCTT | 660 |
| GATATATATT | ACGAAGTTAA | TAATAATGAA | CAAAAGATT | TATTAAAAGA | TTTACTTAAG | 720 |
| AGATACGGTG | AATTTGAAGT | CTATAACGCA | GATACTGGAT | TAATTTATGC | TAAAAATCTA | 780 |
| AGTATTAAAA | ATTATGATAC | TGTGATTCAA | GTAGAAAGGT | TGCCAGTTAA | TTTGAAAGTT | 840 |
| AGAGCATATA | CTAAGGATGA | AAATGGTCGC | AATCTATGTT | TGATGAAAAT | AACATCTAGT | 900 |
| ACAGAAGTAG | ACCCCGAGTA | TGTAACTAGT | AATAATGCTT | TATTGGGTAC | GCTCAGAGTA | 960 |
| TATAAAAAGT | TTGATAAATC | TCATTTAAAA | ATTGTAATGC | ATAACAGAGG | AAGTGGTAAT | 1020 |
| GTATTCCAT | TAAGATCATT | ATATCTGGAA | TTGTCTAATG | TAAAAGGATA | TCCAGTTAAA | 1080 |
| GCATCTGATA | CTTCGAGATT | AGATGTTGGT | ATTTACAAAT | TAAATAAAAT | TTATGTAGAT | 1140 |
| AACGACGAAA | ATAAAATTAT | ATTGGAAGAA | ATTGAAGCAG | AATATAGATG | CGGAAGACAA | 1200 |
| GTATTCCACG | AACGTGTAAA | ACTTAATAAA | CACCAATGTA | AATATACTCC | CAAATGTCCA | 1260 |
| TTCCAATTTG | TTGTAAACAG | CCCAGATACT | ACGATTCACT | TATATGGTAT | TTCTAATGTT | 1320 |
| TGTTTAAAAC | CTAAAGTACC | CAAAAATTTA | AGACTTTGGG | GATGGATTTT | AGATTGCGAT | 1380 |
| ACTTCTAGAT | TTATTAAACA | TATGGCTGAT | GGATCTGATG | ATTTAGATCT | TGACGTTAGG | 1440 |
| CTTAATAGAA | ATGATATATG | TTTAAAACAA | GCCATAAAAC | AACATTATAC | TAATGTAATT | 1500 |
| ATATTAGAGT | ACGCAAATAC | ATATCCAAAT | TGCACATTAT | CATTGGGTAA | TAATAGATTT | 1560 |
| AATAATGTAT | TTGATATGAA | TGATAACAAA | ACTATATCTG | AGTATACTAA | CTTTACAAAA | 1620 |
| AGTAGACAAG | ACCTTAATAA | CATGTCATGT | ATATTAGGAA | TAAACATAGG | TAATTCCGTA | 1680 |
| AATATTAGTA | GTTTGCCTGG | TTGGGTAACA | CCTCACGAAG | CTAAAATTCT | AAGATCTGGT | 1740 |
| TGTGCTAGAG | TTAGAGAATT | TTGTAAATCA | TTCTGTGATC | TTTCTAATAA | GAGATTCTAT | 1800 |
| GCTATGGCTA | GAGATCTCGT | AAGTTTACTA | TTTATGTGTA | ACTATGTTAA | TATTGAAATT | 1860 |
| AACGAAGCAG | TATGCGAATA | TCCTGGATAT | GTCATATTAT | TCGCAAGAGC | TATTAAAGTA | 1920 |
| ATTAATGATT | TATTATTAAT | TAACGGAGTA | GATAATCTAG | CAGGATATTC | AATTTCCTTA | 1980 |
| CCTATACATT | ATGGATCTAC | TGAAAAGACT | CTACCAAATG | AAAAGTATGG | TGGTGTTGAT | 2040 |
| AAGAAATTTA | AATATCTATT | CTTAAAGAAT | AAACTAAAAG | ATTTAATGCG | TGATGCTGAT | 2100 |
| TTTGTCCAAC | CTCCATTATA | TATTTCTACT | TACTTTAGAA | CTTTATTGGA | TGCTCCACCA | 2160 |

| | | | | | | |
|---|---|---|---|---|---|---|
| ACTGATAATT | ATGAAAAATA | TTTGGTTGAT | TCGTCCGTAC | AATCACAAGA | TGTTCTACAG | 2220 |
| GGTCTGTTGA | ATACATGTAA | TACTATTGAT | ACTAATGCTA | GAGTTGCATC | AAGTGTTATT | 2280 |
| GGATATGTTT | ATGAACCATG | CGGAACATCA | GAACATAAAA | TTGGTTCAGA | AGCATTGTGT | 2340 |
| AAAATGGCTA | AAGAAGCATC | TAGATTAGGA | AATCTAGGTT | TAGTAAATCG | TATTAATGAA | 2400 |
| AGTAATTACA | ACAAATGTAA | TAAATATGGT | TATAGAGGAG | TATACGAAAA | TAACAAACTA | 2460 |
| AAAACAAAAT | ATTATAGAGA | AATATTTGAT | TGTAATCCTA | ATAATAATAA | TGAATTAATA | 2520 |
| TCCAGATATG | GATATAGAAT | AATGGATTTA | CATAAAATTG | GAGAAATTTT | TGCAAATTAC | 2580 |
| GATGAAAGTG | AATCTCCTTG | CGAACGAAGA | TGTCATTACT | TGGAAGATAG | AGGTCTTTTA | 2640 |
| TATGGTCCTG | AATATGTACA | TCACAGATAT | CAAGAATCAT | GTACGCCTAA | TACGTTTGGA | 2700 |
| AATAACACAA | ATTGTGTAAC | AAGAAATGGT | GAACAACACG | TATACGAAAA | TAGTTGTGGA | 2760 |
| GATAATGCAA | CATGTGGAAG | AAGAACAGGA | TATGGAAGAA | GAAGTAGGGA | TGAATGGAAT | 2820 |
| GACTATAGAA | AACCCCACGT | TTATGACAAT | TGTGCCGATG | CAAATAGTTC | ATCTTCAGAT | 2880 |
| AGCTGTTCAG | ACAGTAGTAG | TAGTAGTGAA | TCTGAATCTG | ATTCAGATGG | ATGTTGCGAC | 2940 |
| ACAGATGCTA | GTTTAGATTC | TGATATTGAA | AATTGTTATC | AAAATCCATC | AAAATGTGAT | 3000 |
| GCAGGATGCT | AA | | | | | 3012 |

( 2 ) INFORMATION FOR SEQ ID NO:22:

( i ) SEQUENCE CHARACTERISTICS:
        ( A ) LENGTH: 419 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:22:

| | | | | | | |
|---|---|---|---|---|---|---|
| TCAACTAATA | ATAATATATT | TTATGCAGTT | TCAACTTTTG | GATTTTAAG | TACAGAAAGT | 60 |
| ACTGGTATTA | ATTTAACATA | TACAAATTCT | AGAGATTGTA | TTATAGATTT | ATTTTCTAGA | 120 |
| ATTATAAAAA | TAGTATATGA | TCCTTGTACT | GTCGAAACAT | CTAACGATTG | TAGATTATTA | 180 |
| AGATTATTGA | TGGCCAATAC | ATCATAAATA | CATTATAATA | TTATTATAAT | ATCAATCATA | 240 |
| ATTTTTATAT | ATATTTTATC | TAAAAGGACT | TTTTATTTTT | TATATATTAA | TAATAATAAA | 300 |
| TGAGTAACGT | ACCTTTAGCA | ACCAAAACAA | TAAGAAAATT | ATCAAATCGA | AAATATGAAA | 360 |
| TAAAGATTTA | TTTAAAAGAT | GAAAATACTT | GTTCGAACG | TGTAGTAGAT | ATGGTAGTT | 419 |

( 2 ) INFORMATION FOR SEQ ID NO:23:

( i ) SEQUENCE CHARACTERISTICS:
        ( A ) LENGTH: 678 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:23:

| | | | | | | |
|---|---|---|---|---|---|---|
| ATGTTTCTAG | TTTATTTCAA | TACATTTTTA | ATAATAATTT | TATTATTTGG | TATTATAGGT | 60 |
| ATTTATATAT | TAACATTTGT | GTTTAATATA | GATTTTTTAA | TAAATAATAA | TAAAATATAT | 120 |
| ATATTATCAT | ATAACGCAAC | TAATATAAAC | AATATAAATA | ATTTAAATTT | ATACGATTAT | 180 |
| TCAGATATTA | TATTTTTGAC | AAATTTTAAC | ATAAATAATA | ATCTTTTAGT | AACACAAGCT | 240 |
| AATAATTTAC | AAGATATACC | AATATTTAAT | GTAAATAATA | TTATATCTAA | TCAATATAAT | 300 |

| | | | | | |
|---|---|---|---|---|---|
| TTTTATTCAG | CGTCTAGTAA | TAATGTAAAT | ATATTATTAG | GATTAAGAAA | AACATTAAAT | 360
| ATAAATAGAA | ATCCATTTTT | ATTATTTAGA | AATACATCTC | TAGCTATAGT | TTTCAATAAT | 420
| AATGAAACTT | TTCACTGTTA | TATAAGTTCA | AATCAAAATA | GTGATGTATT | AGATATAGTA | 480
| TCACATATAG | AATTTATGAA | ATCTAGATAT | AATAAATATG | TAATTATAGG | AGAAATACCC | 540
| GTAAATAATA | ATATATCTAT | TAATAATATA | TTAAATAATT | TTGCTATTAT | AACTAATGTG | 600
| AGATTAATAG | ATAAATATAA | CTCTATAATA | TCATTTTTAA | ATATCAACGT | AGGAACACTT | 660
| TTTGTCATAA | ATCCATAA | | | | | 678

(2) INFORMATION FOR SEQ ID NO:24:

(i) SEQUENCE CHARACTERISTICS:
        (A) LENGTH: 486 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:24:

| | | | | | |
|---|---|---|---|---|---|
| ATGTCAATAT | TTATCTACTA | TATTTTCAAC | AATAGATTTT | ATATATATAA | AAGAATGAAT | 60
| ACTGTACAAA | TTTTAGTTGT | CATATTAATA | ACAACAGCAT | TATCTTTCT | AGTTTTCAA | 120
| TTATGGTATT | ATGCCGAAAA | TTACGAATAT | ATATTAAGAT | ATAATGATAC | ATATTCAAAT | 180
| TTACAATTTG | CGAGAAGCGC | AAATATAAAT | TTGATGATT | TAACTGTTTT | TGATCCCAAC | 240
| GATAATGTTT | TTAATGTTGA | AGAAAAATGG | CGCTGTGCTT | CAACTAATAA | TAATATATTT | 300
| TATGCAGTTT | CAACTTTTGG | ATTTTTAAGT | ACAGAAAGTA | CTGGTATTAA | TTTAACATAT | 360
| ACAAATTCTA | GAGATTGTAT | TATAGATTTA | TTTTCTAGAA | TTATAAAAAT | AGTATATGAT | 420
| CCTTGTACTG | TCGAAACATC | TAACGATTGT | AGATTATTAA | GATTATTGAT | GGCCAATACA | 480
| TCATAA | | | | | | 486

(2) INFORMATION FOR SEQ ID NO:25:

(i) SEQUENCE CHARACTERISTICS:
        (A) LENGTH: 1395 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:25:

| | | | | | |
|---|---|---|---|---|---|
| TTAAATATTA | GATTCTAAAC | TATTCTTCTC | ATTATCAATA | TAACTATCAT | AATCATTTTT | 60
| TATTTTACTA | CATACATTCA | TAATTCTATT | ACTATTTTT | TTATACATAT | CTATTAATTC | 120
| CATAAACTTT | TTATTTTTTA | TATTAAATAT | TTCTAATGTA | TTTTTAAATT | CGTCAATACT | 180
| ATTAATATCA | TATCTAGAAA | TAAATAATGC | ACCTCTATAA | CTACTAGCCA | ATAAATCACC | 240
| AATAAAACTC | ATAGAATAAT | ATAATTTTTT | AAATTCAAAT | TTAGATTTTA | TGTTGAAATA | 300
| AACTATATAA | TATAAAAATA | TTATATTAAA | CATACCACAA | TCGGGACTAT | CATATTGTAA | 360
| TTCAAAAGTA | TTAAAAAAGT | AATAATTTAC | ATTTTTAAAT | ATATCATTTA | AATATTCTGA | 420
| TAGTACATCA | ATGTATAAAT | AAGCATAATT | AGTATTAGGA | GTACTATTGT | AGTGTTTATG | 480
| GCTTTTTATA | GTCATATCAG | ATTCAATAAA | CATATATTTT | TTATTTTGTT | TTATAAGTTC | 540
| TGGTATATAA | CCACTACTAT | TAAAAAAGTA | TGCAGCTTTT | TTATCTTTAT | CAAAGTGTTT | 600

| | | | | | |
|---|---|---|---|---|---|
| ATCTATTACG | CAACAAGTAA | AATGATCATT | ATAAATTATA | GGAAACATAA | AAAATCTTTT | 660
| TTTATCATTC | ATTAAAAAAA | ATTTTACTCT | ATCTTCAAGT | TTATAGCATC | TCATAGATGA | 720
| AGCTACTGTA | GCAATATTTT | TATCAGTTTT | TTCAAATAAA | ATCAAATGAA | AATAATCATA | 780
| ATCTGTATTA | ATCATAGTTA | ATGGATATAT | ACAATTATAT | ATATCTCCCG | AACTTAACCA | 840
| TGTAGATTTA | TCATGTTTTC | TTGGGTAAGC | TTTAGGTTTA | GGATTAAATC | CCAAAGGCGG | 900
| TATTCCTATT | TGAGCATCCA | AATCATCATA | AATTGTGGCA | AATGTAGAAA | AATCTCTTGT | 960
| TTTGGATAAT | TCTGATTTTA | GAAAAGACTT | TCTCATATAT | ACTAATGGAA | TGCCTTTATA | 1020
| TTTTTTAGAT | GTAATAAAAG | TATTAATATT | TATATTTTTA | TCTTGTAAAT | ATTTTTTTAT | 1080
| AGTCCAAAAT | AGAAAAAATT | TTCTTTTAAT | ATTATTTTCA | AAATTAATAT | TATTAATATG | 1140
| ATTTGGATCT | AAAACTAATT | CATTATATAA | TATTTCCAAG | TATTTTATAG | GTATAAATGT | 1200
| TACTTTACCT | CTTGTTTCAT | CATCATCATC | TATTTTTTCT | AATATAGCTA | TATTTGCATT | 1260
| AGTATTATAT | TTAATAGGAT | TTATAAAATA | TACCATATTA | TCTATTTTAC | TAAAAAATAA | 1320
| CATAGACATA | AAATTAATAC | CAGATTCTGG | CATTTTTAAA | TTTTTATTTG | GAAATCTTCT | 1380
| AATTTTATTA | TTCAT | | | | | 1395

( 2 ) INFORMATION FOR SEQ ID NO:26:

( i ) SEQUENCE CHARACTERISTICS:
        ( A ) LENGTH: 237 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:26:

| | | | | | |
|---|---|---|---|---|---|
| TTATTTTTTT | TTTTGCTTT | TAGGTATAAT | TTTACCTTCT | AAACGTTTAT | CTCCCCAAAC | 60
| ATCTACAGTA | GATGGTTTAT | TAGATTCTGT | GTTATACACA | TCTGCTGGAT | TGCGGCATT | 120
| TGTATCCAAA | CCATAATATC | CAGGTCTATA | ATTATCTTTA | AAAACTTGGG | ATTGAGATAC | 180
| TTCTTCAGTT | TTTAAATTAT | TAAAATATCC | AAGATTATTT | TTTTTGATG | AAGACAT | 237

( 2 ) INFORMATION FOR SEQ ID NO:27:

( i ) SEQUENCE CHARACTERISTICS:
        ( A ) LENGTH: 492 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:27:

| | | | | | |
|---|---|---|---|---|---|
| CTATTCATAA | TAATCATCTG | CTATATATAT | TAATGTATCA | TTCTCTATTA | TAAATATAGG | 60
| TATATTGTCT | TTATCAATCA | TTAATTTTGC | TACAGCTGTA | TTATCTTTAT | ATACTATATT | 120
| TGTGTCTTTG | TTTAATAAAC | CTTTTAATAT | AGTGGCTCTA | TCATAATCTT | TACAATATGA | 180
| TATGGGATAT | AATTTTATAT | TAATAATAAC | ATTAGATACG | TTCATTTCTT | TCATTCTAGT | 240
| TTTACGTATT | GTGTCAAAAA | TTATTTCATT | TTCTGCTGGT | TCTATATATT | TATATGTGTT | 300
| ATGAATAGAT | TCGATAGATG | ATGATTTTAA | TAAATCAAAT | ATAACATTTA | TTTTACCTTG | 360
| TTTATCTTTT | ATAATATCTA | ATATTTCTTT | ATCTACAGAT | TTTCTGTTGT | TGGTATATGA | 420
| TATTAAAAAA | TGAACGTTAA | CATATCTATA | TTCTTGTGGT | AAATCTTTAT | GAGAATTTAA | 480
| TCTTATAGAT | CT | | | | | 492

( 2 ) INFORMATION FOR SEQ ID NO:28:

( i ) SEQUENCE CHARACTERISTICS:
        ( A ) LENGTH: 549 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:28:

| | | | | | | |
|---|---|---|---|---|---|---|
| TTAATATGAA | TTATTATAAC | ATAATCTACA | CACAGGAACA | TATAAATCTT | GTCCACCTAT | 60 |
| TTCAATTATT | TGATTTTTAT | TATGTTTTTT | AATTGTAAAA | GAAGCATCTT | TATAACAAAA | 120 |
| TTGACATATA | GCTTGTAATT | TTTTTATTTT | TTCTACTTTA | GGAATTAATT | TTGATATAGA | 180 |
| ATTAAATATA | TTTCTGTTAA | AGTCACAATT | TAATCCAGCA | ACAATAACTT | TTTTTTATT | 240 |
| ATTAGCCATT | TTATCACAAA | ATTGTTCTAA | ATCATTTTCT | TCAAAAATT | GACACTCATC | 300 |
| TATGCCAATA | ATATCATAAT | TATCTACGAT | ATTGATTTCA | TTAATTAAAT | TATTTGTTTT | 360 |
| AATGTATAAA | TATTCTTTAT | TTAATATATT | TCCGTCATGA | TTTATTATAT | TTTATTTAT | 420 |
| AAATCTATTA | TCTATATTAT | GAGTTATAAT | TACACATTTT | TGATTAGATA | AAATATATCT | 480 |
| ATTAATTTTT | CGCATCAATT | CTGTTGTTTT | GCCAGAAAAC | ATAGGACCAA | TTATTAATTC | 540 |
| TATCGACAT | | | | | | 549 |

( 2 ) INFORMATION FOR SEQ ID NO:29:

( i ) SEQUENCE CHARACTERISTICS:
        ( A ) LENGTH: 69 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:29:

| | | | | | | |
|---|---|---|---|---|---|---|
| TTTTTTTTAT | TATTTGATAT | ATTTTTTCAA | AAAAAAATTA | ATCAATGAAA | AAAAAATAAA | 60 |
| ATTATCAAA | | | | | | 69 |

( 2 ) INFORMATION FOR SEQ ID NO:30:

( i ) SEQUENCE CHARACTERISTICS:
        ( A ) LENGTH: 141 base pairs
        ( B ) TYPE: nucleic acid
        ( C ) STRANDEDNESS: double
        ( D ) TOPOLOGY: unknown ( i i ) MOLECULE TYPE: DNA (genomic)

( x i ) SEQUENCE DESCRIPTION: SEQ ID NO:30:

| | | | | | | |
|---|---|---|---|---|---|---|
| AAACATAGGA | CCAATTATTA | ATTCTATCGA | CATTTTTTT | TATTATTTGA | TATATTTTTT | 60 |
| CAAAAAAAAA | TTAATCAATG | AAAAAAAAAT | AAAATTATCA | AAATGGATTT | ACTAAATTCT | 120 |
| GATATAATTT | TAATAAATAT | T | | | | 141 |

( 2 ) INFORMATION FOR SEQ ID NO:31:

( i ) SEQUENCE CHARACTERISTICS:
        ( A ) LENGTH: 201 base pairs
        ( B ) TYPE: nucleic acid
        ( C ) STRANDEDNESS: double
        ( D ) TOPOLOGY: unknown (ii) MOLECULE TYPE: DNA (genomic)

(xi) SEQUENCE DESCRIPTION: SEQ ID NO:31:

| | | | | | |
|---|---|---|---|---|---|
| TTATAAACAA | CAATCATATT | TTTTTAAAGA | ATCTAATAAA | TTTTTTAACA | TTTTATTATT | 60 |
| ATTTGATAAT | TGTTTATTTA | ATTCGTTATT | GATATTAACA | ATATTATTTA | TCATTTTACC | 120 |
| TATTTTTTTT | TTTCTATCTA | CTAACGAAAT | ATCAGATTTT | GCACCTTCAA | TATCAGAATA | 180 |
| ATAATTATCA | TTATTTTGCA | T | | | | 201 |

(2) INFORMATION FOR SEQ ID NO:32:

(i) SEQUENCE CHARACTERISTICS:
        (A) LENGTH: 660 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:32:

| | | | | | |
|---|---|---|---|---|---|
| ATGGATTTAC | TAAATTCTGA | TATAATTTTA | ATAAATATTT | TAAAATATTA | TAATTTAAAA | 60 |
| AAAATAATAA | TAAACAGAGA | TAATGTTATT | AATATTAATA | TATTAAAAAA | ATTAGTTAAT | 120 |
| TTAGAAGAAT | TGCATATAAT | ATATTATGAT | AATAATATTT | TAAATAATAT | TCCAGAAAAT | 180 |
| ATTAAAAGTT | TATATATTTC | AAATTTAAAT | ATTATTAATT | TAAATTTTAT | AACAAAATTA | 240 |
| AAAAATATAA | CATATTTAGA | TATATCTTAT | AACAAAATA | GCAATATAAG | TAATATTATA | 300 |
| CTACCACATT | CTATAGAATT | TTTAAATTGT | GAATCATGTA | ATATAAATGA | CTATAATTTT | 360 |
| ATTAATAATT | TAGTAAATTT | AAAAAAATTA | ATAATATCTA | AAAATAAATT | TGGTAACTTT | 420 |
| AATAATGTTT | TTCCTATTAG | TATAGTTGAG | TTAAATATGG | AATCAATACA | AATAAAAGAT | 480 |
| TATAAATTTA | TAGAAAAATT | AATTAATTTA | AAAAAATTAG | ATATATCTTT | CAATGTTAAA | 540 |
| AAAAATAATA | TACATTTGAT | AAAATTTCCA | AAAAGTATAA | CTCATTTATG | TGATTATCAA | 600 |
| TCATATAAAG | AAAATTATAA | TTATTTAAAA | AATTTATCAA | ATATAATTGA | ATATGAATTC | 660 |

(2) INFORMATION FOR SEQ ID NO:33:

(i) SEQUENCE CHARACTERISTICS:
        (A) LENGTH: 3907 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:33:

| | | | | | |
|---|---|---|---|---|---|
| TTCTAAACGT | TTATCTCCCC | AAACATCTAC | AGTAGATGGT | TTATTAGATT | CTGTGTTATA | 60 |
| CACATCTGCT | GGATTTGCGG | CATTTGTATC | CAAACCATAA | TATCCAGGTC | TATAATTATC | 120 |
| TTTAAAAACT | TGGGATTGAG | ATACTTCTTC | AGTTTTAAA | TTATTAAAAT | ATCCAAGATT | 180 |
| ATTTTTTTTT | GATGAAGACA | TAATTGATAT | TATAATACTT | TATAGATATG | TCAATATTTA | 240 |
| TCTACTATAT | TTTCAACAAT | AGATTTTATA | TATATAAAAG | AATGAATACT | GTACAAATTT | 300 |
| TAGTTGTCAT | ATTAATAACA | ACAGCATTAT | CTTTTCTAGT | TTTTCAATTA | TGGTATTATG | 360 |
| CCGAAAATTA | CGAATATATA | TTAAGATATA | ATGATACATA | TTCAAATTTA | CAATTTGCGA | 420 |
| GAAGCGCAAA | TATAAATTTT | GATGATTTAA | CTGTTTTTGA | TCCCAACGAT | AATGTTTTTA | 480 |
| ATGTTGAAGA | AAAATGGCGC | TGTGCTTCAA | CTAATAATAA | TATATTTTAT | GCAGTTTCAA | 540 |
| CTTTTGGATT | TTTAAGTACA | GAAAGTACTG | GTATTAATTT | AACATATACA | AATTCTAGAG | 600 |

-continued

| | | | | | | |
|---|---|---|---|---|---|---|
| ATTGTATTAT | AGATTTATTT | TCTAGAATTA | TAAAAATAGT | ATATGATCCT | TGTACTGTCG | 660 |
| AAACATCTAA | CGATTGTAGA | TTATTAAGAT | TATTGATGGC | CAATACATCA | TAAATACATT | 720 |
| ATAATATTAT | TATAATATCA | ATCATAATTT | TTATATATAT | TTTATCTAAA | AGGACTTTTT | 780 |
| ATTTTTTATA | TATTAATAAT | AATAAATGAG | TAACGTACCT | TTAGCAACCA | AACAATAAG | 840 |
| AAAATTATCA | AATCGAAAAT | ATGAAATAAA | GATTTATTTA | AAAGATGAAA | ATACTTGTTT | 900 |
| CGAACGTGTA | GTAGATATGG | TAGTTCCATT | ATATGATGTG | TGTAATGAAA | CTTCTGGTGT | 960 |
| TACTTTAGAA | TCATGTAGTC | CAAATATAGA | AGTAATTGAA | TTAGACAATA | CTCATGTTAG | 1020 |
| AATCAAAGTT | CACGGCGATA | CATTAAAAGA | AATGTGTTTT | GAATTATTGT | TCCCGTGTAA | 1080 |
| TGTAAACGAA | GCCCAAGTAT | GGAAATATGT | AAGTCGATTA | TTGCTAGATA | ATGTATCACA | 1140 |
| TAATGACGTA | AAATATAAAT | TAGCTAATTT | TAGACTGACT | CTTAATGGAA | AACATTTAAA | 1200 |
| ATTAAAAGAA | ATCGATCAAC | CGCTATTTAT | TTATTTTGTC | GATGATTTGG | GAAATTATGG | 1260 |
| ATTAATTACT | AAGGAAAATA | TTCAAAATAA | TAATTTACAA | GTAACAAAG | ATGCATCATT | 1320 |
| TATTACTATA | TTTCCACAAT | ATGCGTATAT | TTGTTTAGGT | AGAAAAGTAT | ATTTAAATGA | 1380 |
| AAAAGTAACT | TTTGATGTAA | CTACAGATGC | AACTAATATT | ACTTTAGATT | TTAATAAATC | 1440 |
| TGTTAATATC | GCAGTATCAT | TCCTTGATAT | ATATTACGAA | GTTAATAATA | ATGAACAAAA | 1500 |
| AGATTTATTA | AAAGATTTAC | TTAAGAGATA | CGGTGAATTT | GAAGTCTATA | ACGCAGATAC | 1560 |
| TGGATTAATT | TATGCTAAAA | ATCTAAGTAT | TAAAAATTAT | GATACTGTGA | TTCAAGTAGA | 1620 |
| AAGGTTGCCA | GTTAATTTGA | AAGTTAGAGC | ATATACTAAG | GATGAAAATG | GTCGCAATCT | 1680 |
| ATGTTTGATG | AAAATAACAT | CTAGTACAGA | AGTAGACCCC | GAGTATGTAA | CTAGTAATAA | 1740 |
| TGCTTTATTG | GGTACGCTCA | GAGTATATAA | AAAGTTTGAT | AAATCTCATT | TAAAAATTGT | 1800 |
| AATGCATAAC | AGAGGAAGTG | GTAATGTATT | TCCATTAAGA | TCATTATATC | TGGAATTGTC | 1860 |
| TAATGTAAAA | GGATATCCAG | TTAAAGCATC | TGATACTTCG | AGATTAGATG | TTGGTATTTA | 1920 |
| CAAATTAAAT | AAAATTTATG | TAGATAACGA | CGAAAATAAA | ATTATATTGG | AAGAAATTGA | 1980 |
| AGCAGAATAT | AGATGCGGAA | GACAAGTATT | CCACGAACGT | GTAAAACTTA | ATAAACACCA | 2040 |
| ATGTAAATAT | ACTCCCAAAT | GTCCATTCCA | ATTTGTTGTA | AACAGCCCAG | ATACTACGAT | 2100 |
| TCACTTATAT | GGTATTTCTA | ATGTTTGTTT | AAAACCTAAA | GTACCCAAAA | ATTTAAGACT | 2160 |
| TTGGGGATGG | ATTTTAGATT | GCGATACTTC | TAGATTTATT | AAACATATGG | CTGATGGATC | 2220 |
| TGATGATTTA | GATCTTGACG | TTAGGCTTAA | TAGAAATGAT | ATATGTTTAA | AACAAGCCAT | 2280 |
| AAAACAACAT | TATACTAATG | TAATTATATT | AGAGTACGCA | AATACATATC | CAAATTGCAC | 2340 |
| ATTATCATTG | GGTAATAATA | GATTAATAA | TGTATTTGAT | ATGAATGATA | ACAAAACTAT | 2400 |
| ATCTGAGTAT | ACTAACTTTA | CAAAAAGTAG | ACAAGACCTT | AATAACATGT | CATGTATATT | 2460 |
| AGGAATAAAC | ATAGGTAATT | CCGTAAATAT | TAGTAGTTTG | CCTGGTTGGG | TAACACCTCA | 2520 |
| CGAAGCTAAA | ATTCTAAGAT | CTGGTTGTGC | TAGAGTTAGA | GAATTTTGTA | AATCATTCTG | 2580 |
| TGATCTTTCT | AATAAGAGAT | TCTATGCTAT | GGCTAGAGAT | CTCGTAAGTT | TACTATTTAT | 2640 |
| GTGTAACTAT | GTTAATATTG | AAATTAACGA | AGCAGTATGC | GAATATCCTG | GATATGTCAT | 2700 |
| ATTATTCGCA | AGAGCTATTA | AAGTAATTAA | TGATTTATTA | TTAATTAACG | GAGTAGATAA | 2760 |
| TCTAGCAGGA | TATTCAATTT | CCTTACCTAT | ACATTATGGA | TCTACTGAAA | AGACTCTACC | 2820 |
| AAATGAAAAG | TATGGTGGTG | TTGATAAGAA | ATTTAAATAT | CTATTCTTAA | AGAATAAACT | 2880 |
| AAAAGATTTA | ATGCGTGATG | CTGATTTTGT | CCAACCTCCA | TTATATATTT | CTACTTACTT | 2940 |

|  |  |  |  |  |  |  |
|---|---|---|---|---|---|---|
| TAGAACTTTA | TTGGATGCTC | CACCAACTGA | TAATTATGAA | AAATATTTGG | TTGATTCGTC | 3000 |
| CGTACAATCA | CAAGATGTTC | TACAGGGTCT | GTTGAATACA | TGTAATACTA | TTGATACTAA | 3060 |
| TGCTAGAGTT | GCATCAAGTG | TTATTGGATA | TGTTTATGAA | CCATGCGGAA | CATCAGAACA | 3120 |
| TAAAATTGGT | TCAGAAGCAT | TGTGTAAAAT | GGCTAAAGAA | GCATCTAGAT | TAGGAAATCT | 3180 |
| AGGTTTAGTA | AATCGTATTA | ATGAAAGTAA | TTACAACAAA | TGTAATAAAT | ATGGTTATAG | 3240 |
| AGGAGTATAC | GAAAATAACA | AACTAAAAAC | AAAATATTAT | AGAGAAATAT | TTGATTGTAA | 3300 |
| TCCTAATAAT | AATAATGAAT | TAATATCCAG | ATATGGATAT | AGAATAATGG | ATTTACATAA | 3360 |
| AATTGGAGAA | ATTTTTGCAA | ATTACGATGA | AAGTGAATCT | CCTTGCGAAC | GAAGATGTCA | 3420 |
| TTACTTGGAA | GATAGAGGTC | TTTTATATGG | TCCTGAATAT | GTACATCACA | GATATCAAGA | 3480 |
| ATCATGTACG | CCTAATACGT | TTGGAAATAA | CACAAATTGT | GTAACAAGAA | ATGGTGAACA | 3540 |
| ACACGTATAC | GAAAATAGTT | GTGGAGATAA | TGCAACATGT | GGAAGAAGAA | CAGGATATGG | 3600 |
| AAGAAGAAGT | AGGGATGAAT | GGAATGACTA | TAGAAAACCC | CACGTTTATG | ACAATTGTGC | 3660 |
| CGATGCAAAT | AGTTCATCTT | CAGATAGCTG | TTCAGACAGT | AGTAGTAGTA | GTGAATCTGA | 3720 |
| ATCTGATTCA | GATGGATGTT | GCGACACAGA | TGCTAGTTTA | GATTCTGATA | TTGAAAATTG | 3780 |
| TTATCAAAAT | CCATCAAAAT | GTGATGCAGG | ATGCTAAATG | AAATTTAATA | TTATATAATA | 3840 |
| TTAACTTACA | AGTTATAAAA | ATCATTAAAA | TGATTTTTTA | AAATGATATT | ATCGATAGTT | 3900 |
| GTGATAA |  |  |  |  |  | 3907 |

( 2 ) INFORMATION FOR SEQ ID NO:34:

( i ) SEQUENCE CHARACTERISTICS:
        ( A ) LENGTH: 25 amino acids
        ( B ) TYPE: amino acid
        ( D ) TOPOLOGY: unknown ( i i ) MOLECULE TYPE: protein ( i x ) FEATURE:
        ( A ) NAME/KEY: Region
        ( B ) LOCATION: 3
        ( D ) OTHER INFORMATION: /note="This amino acid may be
            either Asn or Arg."

( i x ) FEATURE:
        ( A ) NAME/KEY: Region
        ( B ) LOCATION: 12
        ( D ) OTHER INFORMATION: /note="This amino acid may be
            either Asn or Arg."

( x i ) SEQUENCE DESCRIPTION: SEQ ID NO:34:

Met Ala Xaa Asp Leu Val Ser Leu Leu Phe Met Xaa Xaa Tyr Val Asn
1               5                   10                  15

Ile Glu Ile Asn Glu Ala Val Xaa Glu
            20                  25

( 2 ) INFORMATION FOR SEQ ID NO:35:

( i ) SEQUENCE CHARACTERISTICS:
        ( A ) LENGTH: 17 amino acids
        ( B ) TYPE: amino acid
        ( D ) TOPOLOGY: unknown ( i i ) MOLECULE TYPE: peptide ( i x ) FEATURE:
        ( A ) NAME/KEY: Region
        ( B ) LOCATION: 15
        ( D ) OTHER INFORMATION: /note="This amino acid may be
            either Thr or Ile."

( x i ) SEQUENCE DESCRIPTION: SEQ ID NO:35:

Met Lys Ile Thr Ser Ser Thr Glu Val Asp Pro Glu Tyr Val Xaa Ser
1               5                   10                  15
Asn ( 2 ) INFORMATION FOR SEQ ID NO:36:

( i ) SEQUENCE CHARACTERISTICS:
( A ) LENGTH: 8 amino acids
( B ) TYPE: amino acid
( D ) TOPOLOGY: unknown ( i i ) MOLECULE TYPE: protein ( x i ) SEQUENCE DESCRIPTION: SEQ ID NO:36:

Asn Ala Leu Phe Phe Asn Val Phe
1               5

( 2 ) INFORMATION FOR SEQ ID NO:37:

( i ) SEQUENCE CHARACTERISTICS:
( A ) LENGTH: 6 amino acids
( B ) TYPE: amino acid
( D ) TOPOLOGY: unknown ( i i ) MOLECULE TYPE: peptide ( x i ) SEQUENCE DESCRIPTION: SEQ ID NO:37:

Glu Val Asp Pro Glu Tyr
1               5

( 2 ) INFORMATION FOR SEQ ID NO:38:

( i ) SEQUENCE CHARACTERISTICS:
( A ) LENGTH: 66 base pairs
( B ) TYPE: nucleic acid
( C ) STRANDEDNESS: double
( D ) TOPOLOGY: unknown ( i i ) MOLECULE TYPE: DNA (genomic)

( x i ) SEQUENCE DESCRIPTION: SEQ ID NO:38:

ATGGCTAGAG ATCTCGTAAG TTTACTATTT ATGTGTAACT ATGTTAATAT TGAAATTAAC        60

GAAGCA        66

( 2 ) INFORMATION FOR SEQ ID NO:39:

( i ) SEQUENCE CHARACTERISTICS:
( A ) LENGTH: 51 base pairs
( B ) TYPE: nucleic acid
( C ) STRANDEDNESS: double
( D ) TOPOLOGY: unknown ( i i ) MOLECULE TYPE: DNA (genomic)

( x i ) SEQUENCE DESCRIPTION: SEQ ID NO:39:

ATGAAAATAA CATCTAGTAC AGAAGTAGAC CCCGAGTATG TAACTAGTAA T        51

( 2 ) INFORMATION FOR SEQ ID NO:40:

( i ) SEQUENCE CHARACTERISTICS:
( A ) LENGTH: 24 base pairs
( B ) TYPE: nucleic acid
( C ) STRANDEDNESS: double
( D ) TOPOLOGY: unknown (i i) MOLECULE TYPE: DNA (genomic)

(x i) SEQUENCE DESCRIPTION: SEQ ID NO:40:

| AATAATAGAT | TTAATAATGT | ATTT | | | | 24 |

(2) INFORMATION FOR SEQ ID NO:41:

(i) SEQUENCE CHARACTERISTICS:
  (A) LENGTH: 1689 base pairs
  (B) TYPE: nucleic acid
  (C) STRANDEDNESS: single
  (D) TOPOLOGY: linear (i i) MOLECULE TYPE: DNA (genomic)

(x i) SEQUENCE DESCRIPTION: SEQ ID NO:41:

| TCCTATTATT | TGTTTTAATT | CTGATTCATT | CCACGGCATA | TCTAATATAA | TTATATCATT | 60 |
|---|---|---|---|---|---|---|
| AATACATTTG | AATGATATGC | CTTCAGATCC | AGCGTAAGAA | AATATGCAAA | CTTTTACTTT | 120 |
| TTTACCATTA | TTATTTTCAT | AATTATTATA | TTCGTTTAAT | TCATTATCTC | TAGTTTTAA | 180 |
| AGTTTTGCTA | GAATATTCAA | TATAAGAAAT | ATTAAAACAA | TTAAAATAAC | ATTTTAAACT | 240 |
| TGATATTCCT | TCAAAATTAA | CTAAAGGTTC | AAATATTAAT | ACTTTCCTC | TCGAATTTAA | 300 |
| AATTATTTTA | CAAGTTTCTA | TATATTTACA | CGAATATTGA | TATAATATAT | TATAATTATT | 360 |
| TATATCAGTG | ATTGGTAAAT | TAGTTTTTAT | TTTTATATTA | TCATTTTAA | AACTTTCAAT | 420 |
| AAAAGATTCA | GAGAAATTAA | TATTTTTGT | AAACTCGGAA | AATTCAGCAA | GTTTCTTTT | 480 |
| AATCATATCA | TTATATTCTA | TATTATCTAA | ATCTCCTTTT | ATTTAAGAT | CATAAAAAGC | 540 |
| AAATGAAGAT | ATTAATCTTC | TCATAGTTTT | TAAACCACCT | AATTCAGTTT | TATAATCATA | 600 |
| TTTTCTGCC | ATATTATATA | ATTTAGATTG | CTCATCTGAC | ATAATTATAT | TATGATAAAA | 660 |
| TATATTTTT | TTTGCATATC | CATCTATATA | ATTTGTTTCT | GTTAAACTAT | CTGCTTCTAT | 720 |
| TAATCTTTTA | TAAGAACATA | TAGCTAATAA | TGTTTCTCTT | AATTCCTTAA | AATTAATTAA | 780 |
| CTTTCCATTA | TTTATATATT | CTTCTTTTAT | ATTCATAACA | TTTGGTCTAA | GTAAACCTAT | 840 |
| TAAATTATTA | AATTCAGAAA | TATTATTAGT | TACTGGAGTA | GCGGACATAC | ATAATATTT | 900 |
| ATTATTTTCG | AAATTTGCTA | ATTTTATTAA | TTTTTTATAA | ATAGGAGTAA | AATTTCTTTC | 960 |
| GTTATTATCT | TTTTTAACAG | TTCTTGATAT | TAATTTATGA | ACTTCGTCTA | TTATTATTAG | 1020 |
| TAATCTACTT | TTTTTATTAA | GAGAACTTTC | TATAGATCTA | TATATATTAT | TAAATTTATC | 1080 |
| TAAACTAGAT | GACGAATCAT | AATATATAAA | TTTTATATTA | CTGGTATCTG | ATATATATGA | 1140 |
| TCTTATAGTA | TTTAACCAAG | GATCTATGTA | TAATGATTTT | TTAATAAATA | TTAAAATTAT | 1200 |
| CCATCTTGGA | AATAATTCTT | TTATATATTT | TATAATATAC | ACAGCAGTTA | ATGTTTTCC | 1260 |
| CATACCAGTA | TCCCAAAATA | ATAACATACT | ATTCAAATTT | TTTAATCCTA | TGAATATTCT | 1320 |
| ACTTACAAAA | TATTGATAAT | CTTGTAATGT | AATTTCAGTA | TTTGTAATAT | TATTCATAAT | 1380 |
| TTTATTAGGC | AAATGTTGTG | TTTTATCAAG | TGCATAATTT | ATATGTTTAC | CAACAATAGA | 1440 |
| ATCTAATGCA | AACATTTAGT | TATATAAAAA | ATAATATTTA | TATTAACTTA | AGATGTTTCA | 1500 |
| TTAATTTTAT | GTCTGTGATG | TGGAGTTAAA | ACCCAAGATA | TTGATATATC | TATATCATTA | 1560 |
| ATTCTTCTTT | TGAATCTATG | TCTATCAATC | GCAAATTTAT | CCCAGTATAA | TTTTCGAGTT | 1620 |
| TGTTTTGCAG | CATATAACCA | AACATACATA | ATGTGGAGTT | TTGGTGGTTC | GGATGAAAAG | 1680 |
| CGTACTTTT | | | | | | 1689 |

(2) INFORMATION FOR SEQ ID NO:42:

( i ) SEQUENCE CHARACTERISTICS:
    ( A ) LENGTH: 485 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:42:

```
Met Phe Ala Leu Asp Ser Ile Val Gly Lys His Ile Asn Tyr Ala Leu
 1               5                  10                  15

Asp Lys Thr Gln His Leu Pro Asn Lys Ile Met Asn Asn Ile Thr Asn
            20                  25                  30

Thr Glu Ile Thr Leu Gln Asp Tyr Gln Tyr Phe Val Ser Arg Ile Phe
            35                  40                  45

Ile Gly Leu Lys Asn Leu Asn Ser Met Leu Leu Phe Trp Asp Thr Gly
     50                  55                  60

Met Gly Lys Thr Leu Thr Ala Val Tyr Ile Ile Lys Tyr Ile Lys Glu
 65                  70                  75                  80

Leu Phe Pro Arg Trp Ile Ile Leu Ile Phe Ile Lys Lys Ser Leu Tyr
                 85                  90                  95

Ile Asp Pro Trp Leu Asn Thr Ile Arg Ser Tyr Ile Ser Asp Thr Ser
                100                 105                 110

Asn Ile Lys Phe Ile Tyr Tyr Asp Ser Ser Ser Leu Asp Lys Phe
            115                 120                 125

Asn Asn Ile Tyr Arg Ser Ile Glu Ser Ser Leu Asn Lys Lys Ser Arg
    130                 135                 140

Leu Leu Ile Ile Ile Asp Glu Val His Lys Leu Ile Ser Arg Thr Val
145                 150                 155                 160

Lys Lys Asp Asn Asn Glu Arg Asn Phe Thr Pro Ile Tyr Lys Lys Leu
                165                 170                 175

Ile Lys Leu Ala Asn Phe Glu Asn Asn Lys Ile Leu Cys Met Ser Ala
            180                 185                 190

Thr Pro Val Thr Asn Asn Ile Ser Glu Phe Asn Asn Leu Ile Gly Leu
        195                 200                 205

Leu Arg Pro Asn Val Met Asn Ile Lys Glu Glu Tyr Ile Asn Asn Gly
210                 215                 220

Lys Leu Ile Asn Phe Lys Glu Leu Arg Glu Thr Leu Leu Ala Ile Cys
225                 230                 235                 240

Ser Tyr Lys Arg Leu Ile Glu Ala Asp Ser Leu Thr Glu Thr Asn Tyr
                245                 250                 255

Ile Asp Gly Tyr Ala Lys Lys Asn Ile Phe Tyr His Asn Ile Ile Met
            260                 265                 270

Ser Asp Glu Gln Ser Lys Leu Tyr Asn Met Ala Glu Lys Tyr Asp Tyr
        275                 280                 285

Lys Thr Glu Leu Gly Gly Leu Lys Thr Met Arg Arg Leu Ile Ser Ser
    290                 295                 300

Phe Ala Phe Tyr Asp Leu Lys Ile Lys Gly Asp Leu Asp Asn Ile Glu
305                 310                 315                 320

Tyr Asn Asp Met Ile Lys Arg Lys Leu Ala Glu Phe Ser Glu Phe Thr
                325                 330                 335

Lys Asn Ile Asn Phe Ser Glu Ser Phe Ile Glu Ser Phe Lys Asn Asp
            340                 345                 350

Asn Ile Lys Ile Lys Thr Asn Leu Pro Ile Thr Asp Ile Asn Asn Tyr
        355                 360                 365
```

| | | | | | | | | | | | | | | |
|---|---|---|---|---|---|---|---|---|---|---|---|---|---|---|
| Asn | Ile | Leu | Tyr | Gln | Tyr | Ser | Cys | Lys | Tyr | Ile | Glu | Thr | Cys | Lys | Ile |
| | | 370 | | | | 375 | | | | | 380 | | | | |
| Ile | Leu | Asn | Ser | Arg | Gly | Lys | Val | Leu | Ile | Phe | Glu | Pro | Leu | Val | Asn |
| 385 | | | | | 390 | | | | | 395 | | | | | 400 |
| Phe | Glu | Gly | Ile | Ser | Ser | Leu | Lys | Cys | Tyr | Phe | Asn | Cys | Phe | Asn | Ile |
| | | | | 405 | | | | | 410 | | | | | 415 | |
| Ser | Tyr | Ile | Glu | Tyr | Ser | Ser | Lys | Thr | Leu | Lys | Thr | Arg | Asp | Asn | Glu |
| | | | 420 | | | | | 425 | | | | | 430 | | |
| Leu | Asn | Glu | Tyr | Asn | Asn | Tyr | Glu | Asn | Asn | Asn | Gly | Lys | Lys | Val | Lys |
| | | 435 | | | | | 440 | | | | | 445 | | | |
| Val | Cys | Ile | Phe | Ser | Tyr | Ala | Gly | Ser | Glu | Gly | Ile | Ser | Phe | Lys | Cys |
| | 450 | | | | | 455 | | | | | 460 | | | | |
| Ile | Asn | Asp | Ile | Ile | Ile | Leu | Asp | Met | Pro | Trp | Asn | Glu | Ser | Glu | Leu |
| 465 | | | | | 470 | | | | | 475 | | | | | 480 |
| Lys | Gln | Ile | Ile | Gly | | | | | | | | | | | |
| | | | | 485 | | | | | | | | | | | |

( 2 ) INFORMATION FOR SEQ ID NO:43:

( i ) SEQUENCE CHARACTERISTICS:
        ( A ) LENGTH: 235 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:43:

| | | | | | |
|---|---|---|---|---|---|
| AAAAGTTTGA | TAAATCACAT | TTAAAAATTG | TTATGCATAA | TAGAGGAAGT | GGTAATGTAT | 60 |
| TCCCTATTAG | ATCACTATAT | TTGGAATTAT | TGAACGTCAA | AGGTTATCCT | GTAAAAGCAT | 120 |
| CCGATACGTC | TAGGTTAGAT | GTTGGTGTTT | ATAAACTAAA | TAAAATATAT | ATTGATAATG | 180 |
| ATGAAAATAA | AATAATTTTA | GAAGAAATTG | AAACCGATTA | TAGATGTGGA | AGAGA | 235 |

( 2 ) INFORMATION FOR SEQ ID NO:44:

( i ) SEQUENCE CHARACTERISTICS:
        ( A ) LENGTH: 77 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:44:

| | | | | | | | | | | | | | | |
|---|---|---|---|---|---|---|---|---|---|---|---|---|---|---|
| Lys | Phe | Asp | Lys | Ser | His | Leu | Lys | Ile | Val | Met | His | Asn | Arg | Gly | Ser |
| 1 | | | | 5 | | | | | 10 | | | | | 15 | |
| Gly | Asn | Val | Phe | Pro | Ile | Arg | Ser | Leu | Tyr | Leu | Glu | Leu | Leu | Asn | Val |
| | | | 20 | | | | | 25 | | | | | 30 | | |
| Lys | Gly | Tyr | Pro | Val | Lys | Ala | Ser | Asp | Thr | Ser | Arg | Leu | Asp | Val | Gly |
| | | 35 | | | | | 40 | | | | | 45 | | | |
| Val | Tyr | Lys | Leu | Asn | Lys | Ile | Tyr | Ile | Asp | Asn | Asp | Glu | Asn | Lys | Ile |
| | 50 | | | | | 55 | | | | | 60 | | | | |
| Ile | Leu | Glu | Glu | Ile | Glu | Thr | Asp | Tyr | Arg | Cys | Gly | Arg | | | |
| 65 | | | | | 70 | | | | | 75 | | | | | |

( 2 ) INFORMATION FOR SEQ ID NO:45:

( i ) SEQUENCE CHARACTERISTICS:
        ( A ) LENGTH: 235 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:45:

| | | | | |
|---|---|---|---|---|
| AAAAGTTTGA | TAAATCACAT | TTAAAAATCG | TTATGCACAA | TAGAGGAAGC | GGTAATGTAT | 60 |
| TCCCTATTAG | ATCACTATAT | TTGGAATTAT | TGAACGTCAA | AGGTTATCCT | GTTAAAGCAT | 120 |
| CCGATACGTC | TAGGTTAGAC | GTTGGTGTTT | ATAAACTAAA | TAAATATAT | ATTGATAATG | 180 |
| ATGAAAATAA | AATAATTTTA | GAAGAAATCG | AAACCGATTA | TAGATGTGGA | AGAGA | 235 |

(2) INFORMATION FOR SEQ ID NO:46:

(i) SEQUENCE CHARACTERISTICS:
(A) LENGTH: 77 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:46:

Lys Phe Asp Lys Ser His Leu Lys Ile Val Met His Asn Arg Gly Ser
1               5                   10                  15
Gly Asn Val Phe Pro Ile Arg Ser Leu Tyr Leu Glu Leu Leu Asn Val
            20                  25                  30
Lys Gly Tyr Pro Val Lys Ala Ser Asp Thr Ser Arg Leu Asp Val Gly
        35                  40                  45
Val Tyr Lys Leu Asn Lys Ile Tyr Ile Asp Asn Asp Glu Asn Lys Ile
    50                  55                  60
Ile Leu Glu Glu Ile Glu Thr Asp Tyr Arg Cys Gly Arg
65                  70                  75

(2) INFORMATION FOR SEQ ID NO:47:

(i) SEQUENCE CHARACTERISTICS:
(A) LENGTH: 10 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:47:

Lys Phe Lys Tyr Leu Phe Leu Lys Asn Lys
1               5                   10

(2) INFORMATION FOR SEQ ID NO:48:

(i) SEQUENCE CHARACTERISTICS:
(A) LENGTH: 11 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:48:

Lys Ser Val Asn Ile Ala Val Ser Phe Leu Asp
1               5                   10

(2) INFORMATION FOR SEQ ID NO:49:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:49:

Lys Tyr Leu Val Asp Ser Ser Val Gln Ser Gln
1               5                   10

( 2 ) INFORMATION FOR SEQ ID NO:50:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:50:

AGATGATGAT TAAAGTGTGG                                              20

( 2 ) INFORMATION FOR SEQ ID NO:51:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:51:

GATAATGATA CTCCGGTTGC                                              20

( 2 ) INFORMATION FOR SEQ ID NO:52:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:52:

GAAGTNGATC CNGAATATGT                                              20

( 2 ) INFORMATION FOR SEQ ID NO:53:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:53:

GAAAATAAAA TTATATTGGA                                              20

( 2 ) INFORMATION FOR SEQ ID NO:54:

( i ) SEQUENCE CHARACTERISTICS:
( A ) LENGTH: 20 base pairs
( B ) TYPE: nucleic acid ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:54:

AGACAATTCC AGATATAATG 20

( 2 ) INFORMATION FOR SEQ ID NO:55:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:55:

CCGCATCTAT ATTCTGCTTC 20

( 2 ) INFORMATION FOR SEQ ID NO:56:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:56:

GTTTAAAACC TAAAGTACCC 20

( 2 ) INFORMATION FOR SEQ ID NO:57:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:57:

TTTCAAATTA ACTGGCAACC 20

( 2 ) INFORMATION FOR SEQ ID NO:58:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:58:

GGGATGGATT TTAGATTGCG 20

( 2 ) INFORMATION FOR SEQ ID NO:59:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:59:

GTTGCATCTG TAGTTACATC 20

( 2 ) INFORMATION FOR SEQ ID NO:60:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:60:

TCTAGCAATA ATCGACTTAC 20

( 2 ) INFORMATION FOR SEQ ID NO:61:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:61:

GCCTGGTTGG GTAACAACTC 20

( 2 ) INFORMATION FOR SEQ ID NO:62:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:62:

CATTTCTATT AAGCCTAACG 20

( 2 ) INFORMATION FOR SEQ ID NO:63:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:63:

GTACCTTTAG CAACCAAAAC 20

( 2 ) INFORMATION FOR SEQ ID NO:64:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:64:

CTGCTAGATT ATCTACTCCG 20

(2) INFORMATION FOR SEQ ID NO:65:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:65:

AATTGCACAT TATCATTGGG 20

(2) INFORMATION FOR SEQ ID NO:66:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:66:

ATTACCCAAT GATAATGTGC 20